United States Patent
Mahmood et al.

(10) Patent No.: US 12,246,075 B2
(45) Date of Patent: *Mar. 11, 2025

(54) GRANZYME B DIRECTED IMAGING AND THERAPY

(71) Applicant: The General Hospital Corporation, Boston, MA (US)

(72) Inventors: Umar Mahmood, Winchester, MA (US); Benjamin Larimer, Woburn, MA (US); Eric Wehrenberg-Klee, Boston, MA (US)

(73) Assignee: The General Hospital Corporation, Boston, MA (US)

(*) Notice: Subject to any disclaimer, the term of this patent is extended or adjusted under 35 U.S.C. 154(b) by 247 days.

This patent is subject to a terminal disclaimer.

(21) Appl. No.: 18/150,542

(22) Filed: Jan. 5, 2023

(65) Prior Publication Data

US 2023/0338588 A1 Oct. 26, 2023

Related U.S. Application Data

(63) Continuation of application No. 16/314,134, filed as application No. PCT/US2017/040212 on Jun. 30, 2017, now Pat. No. 11,559,590.

(60) Provisional application No. 62/435,541, filed on Dec. 16, 2016, provisional application No. 62/357,845, filed on Jul. 1, 2016.

(51) Int. Cl.
| | | |
|---|---|---|
| A61K 51/08 | (2006.01) | |
| A61B 5/00 | (2006.01) | |
| A61K 51/04 | (2006.01) | |
| A61K 51/10 | (2006.01) | |
| A61P 35/00 | (2006.01) | |
| C12Q 1/02 | (2006.01) | |
| C12Q 1/34 | (2006.01) | |
| C12Q 1/37 | (2006.01) | |
| A61B 6/03 | (2006.01) | |

(52) U.S. Cl.
CPC ............ A61K 51/08 (2013.01); A61B 5/00 (2013.01); A61K 51/0468 (2013.01); A61K 51/1075 (2013.01); A61P 35/00 (2018.01); C12Q 1/02 (2013.01); C12Q 1/34 (2013.01); C12Q 1/37 (2013.01); A61B 5/0033 (2013.01); A61B 5/41 (2013.01); A61B 5/444 (2013.01); A61B 6/037 (2013.01); A61B 2503/40 (2013.01)

(58) Field of Classification Search
CPC .......... A61K 51/04; A61K 51/08; C12Q 1/02; C12Q 1/37; A61P 35/00; A61B 5/00
See application file for complete search history.

(56) References Cited

U.S. PATENT DOCUMENTS

| | | |
|---|---|---|
| 4,472,509 A | 9/1984 | Gansow et al. |
| 4,938,948 A | 7/1990 | Ring et al. |
| 5,021,236 A | 6/1991 | Gries et al. |
| 5,889,155 A | 3/1999 | Ashkenazi et al. |
| 7,927,871 B2 | 4/2011 | Packard et al. |
| 8,715,948 B2 | 5/2014 | Granville et al. |
| 2003/0176784 A1 | 9/2003 | Griffiths et al. |
| 2006/0014712 A1 | 1/2006 | Neuman |
| 2006/0019945 A1 | 1/2006 | Chapman et al. |
| 2006/0111285 A1 | 5/2006 | Multhoff |
| 2007/0184493 A1 | 8/2007 | Packard et al. |
| 2008/0311036 A1 | 12/2008 | Wang et al. |
| 2010/0068151 A1 | 3/2010 | Rosenblum et al. |
| 2010/0160171 A1 | 6/2010 | Freishtat |
| 2011/0083201 A1 | 4/2011 | Rajotte et al. |
| 2014/0030725 A1 | 1/2014 | Binkowski et al. |
| 2014/0056964 A1 | 2/2014 | Hiebert et al. |
| 2017/0260517 A1* | 9/2017 | Lin .......................... C12N 9/52 |

FOREIGN PATENT DOCUMENTS

| | | |
|---|---|---|
| JP | 2014-500271 | 1/2014 |
| KR | 2014/0119633 | 10/2014 |
| WO | WO 2012/076985 | 6/2012 |
| WO | WO 2014/153667 | 10/2014 |

OTHER PUBLICATIONS

U.S. Appl. No. 10/503,155, filed Jul. 28, 2004, Chapman et al.
Ascierto et al., "Biomarkers for immunostimulatory monoclonal antibodies in combination strategies for melanoma and other tumor types," Clinical Cancer Research, 2013, 19(5):1009-1020.
Borghaei et al., "Nivolumab versus Docetaxel in Advanced Nonsquamous Non-Small-Cell Lung Cancer," N Engl J Med, 2015, 373(17):1627-1639.
Brahmer et al., "Safety and Activity of Anti-PD-L1 Antibody in Patients with Advanced Cancer," New England Journal of Medicine, 2012, 366(26):2455-2465.
Burbage, "Ricin fusion toxin targeted to the human granulocyte-macrophage colony stimulating factor receptor is selectively toxic to acute myeloid leukemia cells," Leukemia Research, 1997, 21: 681-690.
Callahan et al., "Checkpoint Blockade for the Treatment of Advanced Melanoma," Cancer Treat Res, 2016, 167:231-250.
Catalán et al., "Mouse cytotoxic T cell-derived granzyme B activates the mitochondrial cell death pathway in a Bim dependent fashion," Journal of Biological Chemistry, 2015, 290: 6868-6877.
Chen et al., "Pegylated Arg-Gly-Asp peptide: 64Cu labeling and PET imaging of brain tumor $\alpha v\beta 3$-integrin expression," Journal of Nuclear Medicine, 2004, 45(10):1776-1783.

(Continued)

*Primary Examiner* — Michael G. Hartley
*Assistant Examiner* — Jagadishwar R Samala
(74) *Attorney, Agent, or Firm* — Fish & Richardson P.C.

(57) ABSTRACT

Provided herein are compounds useful for imaging granzyme B. An exemplary compound provided herein is useful as a radiotracer for position emission tomography (PET) and/or single photon emission tomography (SPECT) imaging. Methods of imaging granzyme B, combination therapies, and kits comprising the granzyme B imaging agents are also provided.

20 Claims, 21 Drawing Sheets

Specification includes a Sequence Listing.

(56) References Cited

OTHER PUBLICATIONS

Dankort et al, "BRafV600E cooperates with Pten silencing to elicit metastatic melanoma," Nature Genetics, 2009, 41: 544-552.
Duraiswamy et al., "Dual blockade of PD-1 and CTLA-4 combined with tumor vaccine effectively restores T-cell rejection function in tumors," Cancer Res, 2013, 73(12):3591-3603.
EP Supplementary Partial European Search Report in EP Appln. No. 17821330, dated Mar. 27, 2020, 15 pages.
Gardner et al, "Interaction Of Peptides Related to Secretin With Hormone Receptors on Pancreatic Acinar Cells," Gastroenterology, 1976, 71: 965-970.
Hahnel et al., "Targeting AKT signaling sensitizes cancer to cellular immunotherapy," Cancer Res, 2008, 68(10):3899-3906.
Herbst et al., "Predictive correlates of response to the anti-PD-L1 antibody MPDL3280A in cancer patients," Nature, 2014, 515(7528):563-567.
Heskamp et al., "Noninvasive Imaging of Tumor PD-L1 Expression Using Radiolabeled Anti-PD-L1 Antibodies," Cancer Research, 2015, 75(14):2928-2936.
Houghten, "General method for the rapid solid-phase synthesis of large numbers of peptides: Specificity of antigen-antibody interaction at the level of individual amino acids," PNAS, 1985, 82: 5131-5135.
International Preliminary Report on Patentability in International Application No. PCT/US2017/040212, mailed on Jan. 1, 2019, 10 pages.
International Search Report and Written Opinion in International Application No. PCT/US2017/040212, mailed on Nov. 6, 2017, 23 pages.
Konishi et al., "Imaging Granzyme B Activity Assesses Immune-Mediated Myocarditis," Circulation Research, Aug. 2015, 117(6):502-512.
Larimer et al., "Quantitative CD3 PET Imaging Predicts Tumor Growth Response to Anti-CTLA-4 Therapy, " Journal of Nuclear Medicine, 2016, 57(10):1607-1611.
Larkin et al., "Combined Nivolumab and Ipilimumab or Monotherapy in Untreated Melanoma," N Engl J Med, 2015, 373(1):23-34.
Li et al., "Real-Time Detection of CTL Function Reveals Distinct Patterns of Caspase Activation Mediated by Fas versus Granzyme B", Journal of Immunology, Jun. 2014, 193(2):519-528.
Lidor et al., "In vitro expression of the diphtheria toxin A-chain gene under the control of human chorionic gonadotropin gene promoters as a means of directing toxicity to ovarian cancer cell lines," American Journal of Obstetrics and Gynecology, 1997, 177: 579-585.
Llosa et al., "The Vigorous Immune Microenvironment of Microsatellite Instable Colon Cancer Is Balanced by Multiple Counter-Inhibitory Checkpoints," Cancer Discovery, 2015, 5(1):43-51.
Longley et al., "5-fluorouracil: mechanisms of action and clinical strategies," Nat Rev Cancer, May 2003, 3(5):330-338.
Mahoney et al., "Combination cancer immunotherapy and new immunomodulatory targets," Nature Reviews, 2015, 14(8):561-584.
Massuda et al., "Regulated expression of the diphtheria toxin A chain by a tumor-specific chimeric transcription factor results in selective toxicity for alveolar rhabdomyosarcoma cells," PNAS, 1997, 94: 14701-14706.
Merrifield et al, "Solid Phase Peptide Synthesis. I. The Synthesis of a Tetrapeptide," Journal of the American Chemical Society, 1963, 85: 2149-2154.

Motzer et al., "Nivolumab versus Everolimus in Advanced Renal-Cell Carcinoma," N Engl J Med, 2015, 373(19):1803-1813.
Naidoo et al., "Toxicities of the anti-PD-1 and anti-PD-L1 immune checkpoint antibodies," Ann Oncol, 2015, 26(12):2375-2391.
Natarajan et al., "Novel Radiotracer for ImmunoPET Imaging of PD-1 Checkpoint Expression on Tumor Infiltrating Lymphocytes," Bioconjugate Chemistry, 2015, 26(10):2062-2069.
Office Action in Japanese Appln. No. 2018-568685, dated May 10, 2022, 8 pages (with English translation).
Pages et al., "Immune infiltration in human tumors: a prognostic factor that should not be ignored," Oncogene, 2010, 29(8):1093-1102.
Peng et al., "Loss of PTEN Promotes Resistance to T Cell-Mediated Immunotherapy," Cancer Discov, 2016, 6(2):202-216.
Postow et al., "Nivolumab and ipilimumab versus ipilimumab in untreated melanoma," N Engl J Med, 2015, 372(21):2006-2017.
PUBCHEM. Substance Record for SID 75808961, Available Date: Jun. 11, 2009 [retrieved on 1-8. 21-24. 63. 108 Aug. 8, 2017). Retrieved from the Internet: <URL: https://pubchem.ncbi.nlm.nih.gov/substance/75808961>. 5 pages.
Ravindranath & Morton, "Role of Gangliosides in Active Immunotherapy with Melanoma Vaccine," International Reviews of Immunology, 1991, 7: 303-329.
Rizvi et al., "Mutational landscape determines sensitivity to PD-1 blockade in non-small cell lung cancer," Science, 2015, 348(6230):124-128.
Rosenberg et al, "Experience with the Use of High-Dose Interleukin-2 in the Treatment of 652 Cancer Patients," Annals of Surgery, 1989, 210: 474.
Rosenberg et al, "Use of tumor-infiltrating lymphocytes and interleukin-2 in the immunotherapy of patients with metastatic melanoma. A preliminary report," New England Journal of Medicine, 1988, 319: 1676-1680.
Rotonda et al., "The three-dimensional structure of human granzyme B compared to caspase-3, key mediators of cell death with cleavage specificity for aspartic acid in P1," Chem Biol, 2001, 8(4):357-368.
Royal et al., "Phase 2 trial of single agent Ipilimumab (anti-CTLA-4) for locally advanced or metastatic pancreatic adenocarcinoma," Journal of Immunotherapy, 2010, 33(8):828-833.
Tavaré et al., "An Effective Immuno-PET Imaging Method to Monitor CD8-Dependent Responses to Immunotherapy," Cancer Research, 2016, 76(1):73-82.
Thornberry et al., "A combinatorial approach defines specificities of members of the caspase family and granzyme B. Functional relationships established for key mediators of Apoptosis," J Biol Chem, 1997, 272(29):17907-17911.
Wherry and Kurachi, "Molecular and cellular insights into T cell exhaustion," Nat Rev Immunol, 2015, 15(8):486-499.
Willoughby et al., "Discovery of potent, selective human granzyme B inhibitors that inhibit CTL mediated apoptosis," Bioorg Med Chem Lett, 2002, 12(16):2197-2200.
Wolchok et al., "Guidelines for the evaluation of immune therapy activity in solid tumors: immune-related response criteria," Clinical Cancer Research, 2009, 15(23):7412-7420.
Yuan et al., Novel technologies and emerging biomarkers for personalized cancer immunotherapy, J Immunother Cancer, 2016, 4:3, 25 pages.
Office Action in Japanese Appln. No. 2022-143354, dated Apr. 2, 2024, 8 pages (with English translation).

* cited by examiner

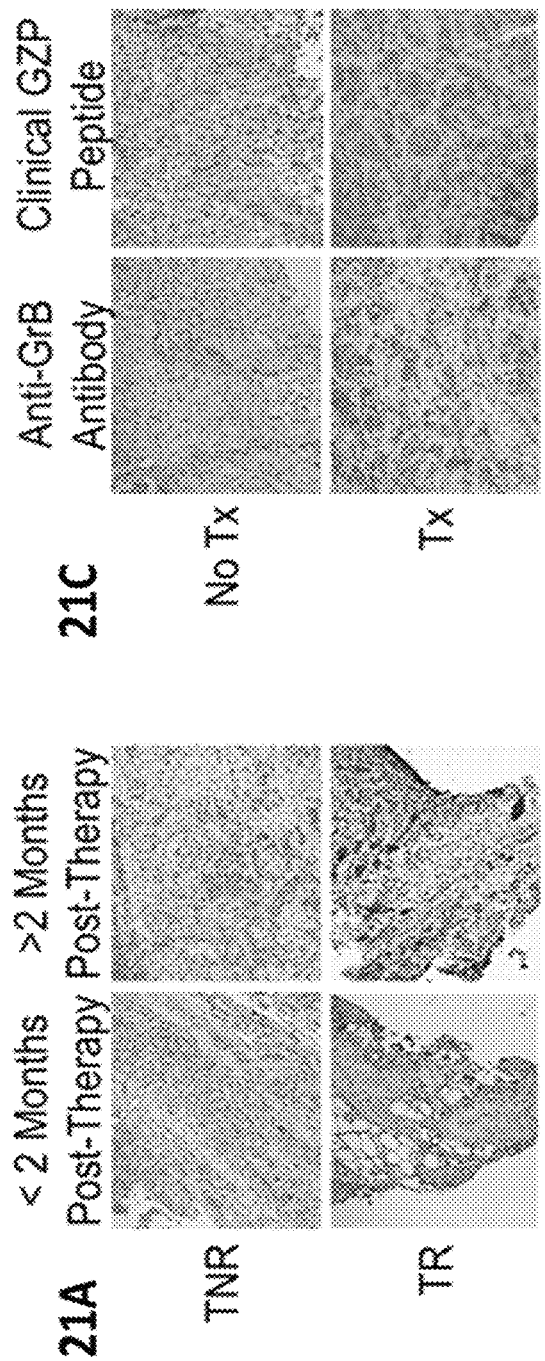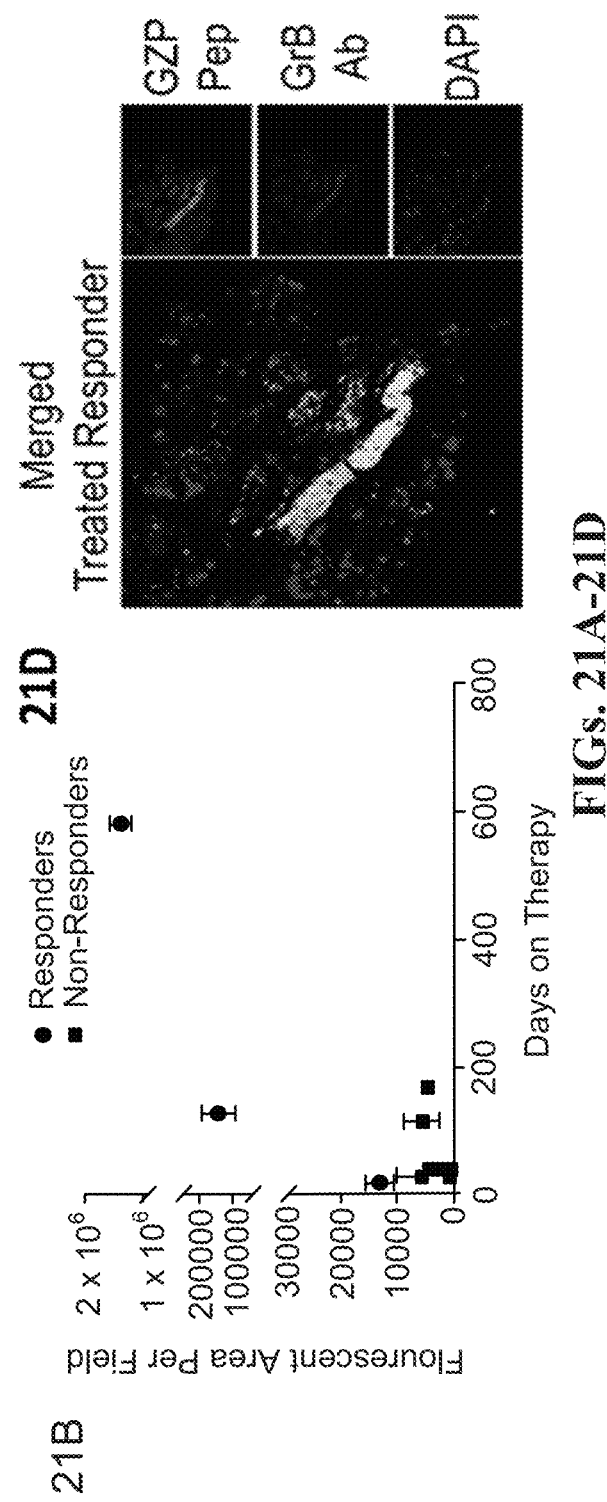
FIGs. 21A-21D

GRANZYME B DIRECTED IMAGING AND THERAPY

CROSS-REFERENCE TO RELATED APPLICATIONS

This application is a continuation of U.S. patent application Ser. No. 16/314,134, filed Dec. 28, 2018, which is a § 371 national stage application of International Application No. PCT/US2017/040212, filed on Jun. 30, 2017, which claims the benefit of U.S. Provisional Application Ser. No. 62/357,845, filed Jul. 1, 2016, and 62/435,541, filed Dec. 16, 2016, the disclosure of each of which is incorporated herein by reference in its entirety.

FEDERALLY SPONSORED RESEARCH OR DEVELOPMENT

This invention was made with Government support under Grant No. P50-CA127003 and 5R01CA166582-03, awarded by the National Institutes of Health. The Government has certain rights in the invention.

SEQUENCE LISTING

This application contains a Sequence Listing that has been submitted electronically as an XML file named "40978-0020003_SL_ST26.XML." The XML file, created on Jun. 6, 2023, is 42,419 bytes in size. The material in the XML file is hereby incorporated by reference in its entirety.

TECHNICAL FIELD

This invention relates to compounds useful for imaging techniques, and more particularly to compounds that are useful for imaging granzyme B using medical imaging, including positron emission tomography.

BACKGROUND

Granzyme B is a serine-protease released through exocytosis by cytotoxic lymphocytes (CTL) during the cellular immune response, and represents one of the two dominant mechanisms, along with the FAS/FASL pathway, by which T-cells mediate cancer-cell death. Granzyme B is released along with the pore-forming protein perforin at the immunological-synapse formed between T-cells and their targets. A portion of the released granzyme B then enters cancer cells, primarily through perforin-pores, where it activates multiple substrates leading to activation of the caspase cascade.

SUMMARY

The present application provides, inter alia, a method of imaging granzyme B in a cell or tissue, comprising:
i) contacting the cell or tissue sample with a compound of Formula I:

$$A\text{-}B\text{—}C \qquad \qquad I$$

or a pharmaceutically acceptable salt thereof, and
ii) imaging the cell or tissue with a suitable imaging technique, thereby imaging granzyme B in the cell or tissue, wherein:
A comprises one or more imaging agents;
B is an optional linking group; and
C is a group that binds granzyme B.

The present application further provides a method of imaging granzyme B in a subject, comprising:
i) administering to the subject a compound of Formula I:

$$A\text{-}B\text{—}C \qquad \qquad I$$

or a pharmaceutically acceptable salt thereof, and
ii) imaging the subject with a suitable imaging technique, thereby imaging granzyme B in the subject, wherein:
A comprises one or more imaging agents;
B is an optional linking group; and
C is a group that binds granzyme B.

The present application further provides a method of imaging an immune response in a cell or tissue sample, comprising:
i) contacting the cell or tissue sample with a compound of Formula I:

$$A\text{-}B\text{—}C \qquad \qquad I$$

or a pharmaceutically acceptable salt thereof, and
ii) imaging the cell or tissue sample with a suitable imaging technique, thereby imaging the immune response in the cell or tissue sample, wherein:
A comprises one or more imaging agents;
B is an optional linking group; and
C is a group that binds granzyme B.

The present application further provides a method of imaging an immune response in a subject, comprising:
i) administering to the subject a compound of Formula I:

$$A\text{-}B\text{—}C \qquad \qquad I$$

or a pharmaceutically acceptable salt thereof, and
ii) imaging the subject with a suitable imaging technique, thereby imaging the immune response in the subject, wherein:
A comprises one or more imaging agents;
B is an optional linking group; and
C is a group that binds granzyme B.

The present application further provides a method of monitoring treatment of a disease in a subject, comprising:
i) administering to the subject a compound of Formula I:

$$A\text{-}B\text{—}C \qquad \qquad I$$

or a pharmaceutically acceptable salt thereof, and
ii) imaging the subject with a suitable imaging technique, wherein:
A comprises one or more imaging agents;
B is an optional linking group; and
C is a group that binds granzyme B.

The present application further provides a method of monitoring an immune response in the treatment of a disease in a subject, comprising:
i) administering to the subject a compound of Formula I:

$$A\text{-}B\text{—}C \qquad \qquad I$$

or a pharmaceutically acceptable salt thereof, and
ii) imaging the subject with a suitable imaging technique, wherein:
A comprises one or more imaging agents;
B is an optional linking group; and
C is a group that binds granzyme B.

In some embodiments, A comprises one or mom imaging agents selected from the group consisting of a paramagnetic ion, an x-ray imaging agent, a fluorophore, and a radioisotope.

In some embodiments, the paramagnetic ion is selected from the group consisting of chromium (III), manganese (II), iron (III), iron (II), cobalt (II), nickel (II), copper (II), neodymium (I), samarium (III), ytterbium (III), gadolinium (III), vanadium (H), terbium (I), dysprosium (I), holmium (I) and erbium (III).

In some embodiments, the x-ray imaging agent is selected from the group consisting of lanthanum (Ill), gold (Ill), lead (I), bismuth (III), and an iodinated x-ray imaging agent.

In some embodiments, the radioisotope is selected from the group consisting of $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{225}Bi$, and 225Ac.

In some embodiments, A is an imaging agent selected from the group consisting of a PET imaging agent, a SPECT imaging agent, and a computed tomography imaging agent. In some embodiments, A is a PET or SPECT imaging agent. In some embodiments, A is a PET or SPECT imaging agent comprising a radioisotope selected from the group consisting of $^{3}H$, $^{11}C$, $^{14}C$, $^{18}F$, $^{35}S$, $^{52}Fe$, $^{58}Co$, $^{64}Cu$, $^{68}Ga$, $^{76}Br$, $^{77}Br$, $^{89}Zr$, $^{111}In$, $^{123}I$, $^{124}I$, $^{125}I$, $^{131}I$, $^{186}Re$, $^{188}Re$, $^{201}Tl$. In some embodiments, A is a PET imaging agent comprising $^{68}Ga$.

In some embodiments, A further comprises a chelating agent. In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TnHA), hydroxyethyidiamine triacetic acid (HEDTA), and 1,4,8,11-tetraazacyclotetadecane-N,N',N'',N'-tetracetic acid (TETA), 1,4,7,10-tetraaza-1,4,7,10-tetra-(2-carbamoyl methyl)-cyclododecane (TCMC), and Desferrioxamine B (DFO). In some embodiments, the chelating agent is selected from the group consisting of 1,4,7-triazacyclononanetriacetic acid (NOTA), 1,4,7,10-tetraazacyclododecane-1,4,7,10-tetrancetic acid (DOTA), and 1,4,7-triazacyclononane-1-glutaric acid-4,7-diacetic acid (NODAGA). In some embodiments, the chelating agent is 1,4,7-triazacyclononanetriacetic acid (NOTA).

In some embodiments, A is a fluorophore. In some embodiments, A is a fluorophore selected from the group consisting of Alexa 350, Alexa 430, AMCA, BODIPY 630/650, BODIPY 650/665, BODIPY-FL, BODPY-R6G, 13BODLPY-TMR, BODLPY-TRX, cascade blue, Cy3, Cy5, 6-FAM, fluorescein isothiocyanate, HEX, 6-JOE, oregon green 488, oregon green 500, oregon green 514, a quantum dot, pacific blue, REG, rhodamine green, rhodamine red, renographin, ROX, TAMRA, TET, tetramethylrhodamine, Texas Red, AF 350, 405, AF532, AF488, AF647, AF680, AF750, Cy5, Cy5.5, Cy7, indocyanine green (ICG), green fluorescent protein (GFP), red fluorescent protein (RFP), and dsRED.

The present application further provides a method of treating a disease in a subject, comprising:
  i) administering to the subject a first compound of Formula I:
or a pharmaceutically acceptable salt thereof, wherein:
  A comprises a non-toxic radioisotope;
  B is an optional linking group; and
  C is a group that binds granzyme B;
  ii) imaging the subject with a suitable imaging technique; and
  iii) administering to the subject a second compound of Formula I:

A-B—C            I or a pharmaceutically acceptable salt thereof, wherein:
  A comprises a toxic radioisotope;
  B is an optional linking group; and
  C is a group that binds granzyme B;
thereby treating the disease in the subject.

In some embodiments, the method further comprises determining if the first compound of Formula I, or a pharmaceutically acceptable salt thereof, binds to a cell or tissue of the subject to be treated prior to the administration of step iii).

In some embodiments, the method further comprises determining if the first compound of Formula I, or a pharmaceutically acceptable salt thereof, binds to granzyme B, prior to the administration of step iii).

In some embodiments, group A of the first compound of Formula I, or a pharmaceutically acceptable salt thereof, comprises a non-toxic radioisotope selected from the group consisting of $^{3}H$, $^{11}C$, $^{14}C$, $^{18}F$, $^{35}S$, $^{52}Fe$, $^{58}Co$, $^{64}Cu$, $^{68}Ga$, $^{76}Br$, $^{77}Br$, $^{89}Zr$. $^{111}In$, $^{123}I$, $^{124}I$, $^{125}I$, $^{131}I$, $^{186}Re$, $^{188}Re$, $^{201}Tl$.

In some embodiments, group A of the first compound of Formula I, or a pharmaceutically acceptable salt thereof, further comprises a chelating agent. In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), and 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC), and Desferrioxamine B (DFO).

In some embodiments, group A of the second compound of Formula I, or a pharmaceutically acceptable salt thereof, comprises a toxic radioisotope selected from the group consisting of an alpha emitter and a beta emitter. In some embodiments, group A of the second compound of Formula I, or a pharmaceutically acceptable salt thereof, comprises a toxic radioisotope selected from the group consisting of $^{211}At$, $^{212}Pb$, $^{212}Bi$, $^{213}Bi$, $^{225}Ac$, $^{227}Th$, $^{177}Lu$, and $^{131}I$.

In some embodiments, B is an optional linking group comprising one or more amino acid residues, one or more carbohydrates, one or more alkylene groups, one or more amine groups, one or more amide groups, one or more alkyleneoxy groups, one or more thiol groups, or any combination thereof. In some embodiments, B is an optional linking group comprising one or more $C_{1-30}$ alkylene groups, one or more amine groups, one or more amide groups, one or more $C_{1-30}$ alkyleneoxy groups, one or more $C_{1-30}$ thiol groups, or any combination thereof. In some embodiments. B is an optional linking group comprising one or more —(OCH$_2$CH$_2$)— groups. In some embodiments, B is an optional linking group of the formula —(OCH$_2$CH$_2$)$_p$—, wherein p is an integer from 1 to 40. In some embodiments, p is an integer from 10 to 40. In some embodiments, p is an integer from to 40. In some embodiments, p is an integer from 25 to 35.

In some embodiments, C is selected from the group consisting of a polypeptide that binds granzyme B, an antibody that binds granzyme B, an antibody fragment that binds granzyme B, and a small organic molecule that binds granzyme B.

In some embodiments, C is an antibody that binds granzyme B. In some embodiments, C is an antibody that binds granzyme B and is selected from the group consisting of, Clone GB11, Clone GrB-7, and NCL-L-Gran-B. In some embodiments, C is an antibody fragment that binds granzyme B.

In some embodiments, C is a polypeptide that binds granzyme B. In some embodiments, the polypeptide that binds granzyme B is from about 4 to about 100 amino acid residues in length. In some embodiments, the polypeptide that binds granzyme B is from about 4 to about 50 amino acid residues in length. In some embodiments, the polypeptide that binds granzyme B is from about 4 to about 25 amino acid residues in length. In some embodiments, the polypeptide that binds granzyme B is from about 4 to about 15 amino acid residues in length.

In some embodiments, C is a polypeptide that binds granzyme B, wherein the polypeptide comprises an amino acid sequence having at least 90V sequence identity to:

(SEQ ID NO: 1)
$X^1$-$X^2$-$X^3$-$X^4$-$X^5$-$X^6$-D wherein:
- $X^1$, $X^2$, and $X^3$ are each independently selected from the group consisting of beta A, G, Q, N, S, T, Y, C, R, D, and E;
- $X^4$ is selected from the group consisting of I and V;
- $X^5$ is selected from the group consisting of E, G, D and S; and
- $X^6$ is selected from the group consisting of E, X, P, S. T. Q, N, A, H, V, F and D.

In some embodiments, $X^4$ is I. In some embodiments, $X^5$ is E. In some embodiments, $X^6$ is F or P.

In some embodiments, the polypeptide comprises an amino acid sequence having at least 90% sequence identity to a sequence selected from the group consisting of:

```
                                    (SEQ ID NO: 2)
beta A-G-G-I-E-F-D;
                                    (SEQ ID NO: 3)
G-G-G-I-E-F-D;
and
                                    (SEQ ID NO: 4)
beta A-G-G-I-E-P-D.
```

In some embodiments, C is a polypeptide comprising an amino acid sequence of SEQ ID NO: 2. In some embodiments, C is a polypeptide comprising an amino acid sequence of SEQ ID NO: 3. In some embodiments, C is a polypeptide comprising an amino acid sequence of SEQ ID NO: 4.

In some embodiments, C is a polypeptide that binds granzyme B, wherein the polypeptide comprises an amino acid sequence having at least 90% sequence identity to:

(SEQ ID NO: 8)
$X^1$-$X^2$-$X^3$-$X^4$-$X^5$-$X^6$-D-$X^7$ wherein:
- $X^1$, $X^2$, and $X^1$ are each independently selected from the group consisting of beta A, G, Q, N, S, T, Y, C, R, D, and E;
- $X^4$ is selected from the group consisting of I and V;
- $X^5$ is selected from the group consisting of E, G, D and S; and
- $X^6$ is selected from the group consisting of E, X, P, S, T, Q, N, A, H, V, F and D; and
- $X^6$ is an electrophilic group comprising the C-terminus of the amino acid sequence of SEQ ID NO: 8.

In some embodiments, $X^4$ is I. In some embodiments, $X^5$ is E. In some embodiments, $X^6$ is F or P.

In some embodiments, $X^7$ is an electrophilic group selected from the group consisting of —C(O)H, —C(O)$C_{1-6}$ alkyl, —C(O)$C_{1-6}$ haloalkyl, —C(O)$C_{1-6}$ alkoxy, —C(O)$C_{1-6}$ haloalkoxy, —C(O)—($C_{1-6}$ alkyl)-(5-10 membered heteroaryl), —C(O)—($C_{1-6}$ haloalkyl))-(5-10 membered heteroaryl), —C(O)—($C_{1-6}$ alkoxy)(5-10 membered heteroaryl), and —C(O)—($C_{1-6}$ haloalkoxy)-(5-10 membered heteroaryl). In some embodiments, $X^7$ is —C(O)H.

In some embodiments, C is a small organic molecule that binds granzyme B. In some embodiments, the small organic molecule is a small molecule peptidomimetic.

In some embodiments, C is a small organic molecule of Formula III:

III 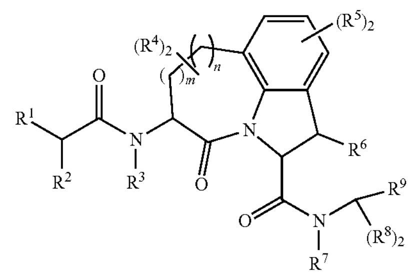 or a pharmaceutically acceptable salt thereof, wherein:
- n is 0, 1, or 2;
- m is 0, 1, or 2;
- $R^1$ and $R^2$ are each independently selected from the group consisting of: hydrogen, $C_{1-6}$ alkyl, $C_{1-6}$ alkoxy, $C_{3-6}$ cycloalky, $C_{6-10}$ aryl, HET, and —N($R^{10}$)$_2$, wherein each $C_{1-6}$ alkyl, $C_{1-6}$ alkoxy, $C_{3-6}$ cycloalkyl, are optionally substituted with 1, 2, or 3 substituents independently selected from the group consisting of halo and hydroxy, and each $C_{6-10}$ aryl and HET are optionally substituted with 1, 2, or 3 substituents independently selected from the group consisting of oxo, halo, hydroxy, $C_{1-4}$ alkyl, and $C_{1-4}$haloalkyl;
- or $R^1$ and $R^2$ may come together, with the carbon atom to which they are attached, to form a 5-6 membered cycloalkyl or 5-6 heterocycloalkyl group, each of which may be optionally substituted with 1, 2, or 3 $R^{10}$groups;
- each $R^3$ and $R^7$ is independently selected from the group consisting of hydrogen, $C_{1-4}$ alkyl, and $C_{1-4}$haloalkyl;
- each $R^4$, $R^5$, $R^6$ and $R^8$ is independently selected from the group consisting of hydrogen, halo, hydroxy, $C_{1-4}$ alkyl, and $C_{1-4}$haloalkyl;
- $R^9$ is HET, which may be optionally substituted with 1, 2, or 3 substituents independently selected from the group consisting of oxo, halo, hydroxy, $C_{1-6}$ alkyl, and $C_{1-4}$ haloalkyl;

R[10] is selected from the group consisting of hydrogen, C$_{1-6}$ alkyl, and —C(O)C$_{1-4}$ alkyl, wherein the —C(O)C$_{1-4}$ alkyl is optionally substituted with —N(R[11])$_2$, HET, and C$_{6-10}$ aryl, wherein the C$_{6-10}$ aryl may be optionally substituted with 1, 2, or 3 halo groups;

each HET is an independently selected mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 oxo groups; and R[11] is selected from hydrogen, C$_{1-4}$ alkyl, and C$_{1-4}$ haloalkyl;

with the proviso that when m is 0, then n is 0 and when n is 0, then m is 0.

In some embodiments, C is selected from the group consisting of:

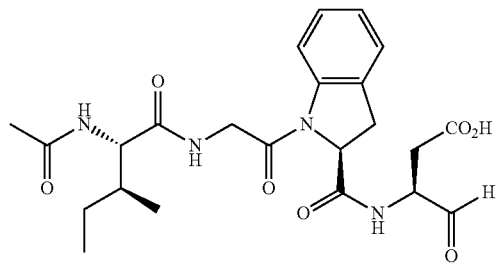 [SMILES: CC[C@H](C)[C@H](NC(C)=O)C(=O)NCC(=O)N1c2ccccc2C[C@H]1C(=O)N[C@H](C=O)CC(=O)O]

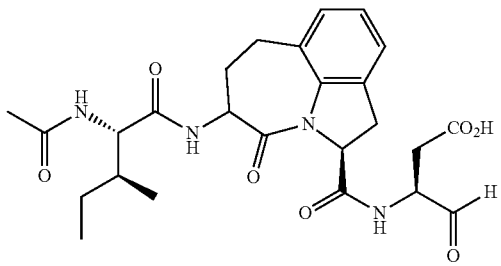 [SMILES: CC[C@H](C)[C@H](NC(C)=O)C(=O)NC1CCc2cccc3c2N(C1=O)[C@H](C(=O)N[C@H](C=O)CC(=O)O)C3]

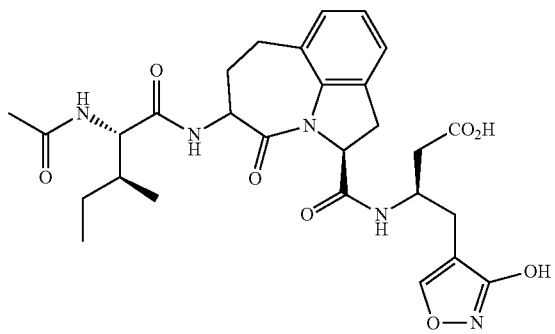 [SMILES: CC[C@H](C)[C@H](NC(C)=O)C(=O)NC1CCc2cccc3c2N(C1=O)[C@H](C(=O)N[C@@H](CC(=O)O)Cc1conc1O)C3]

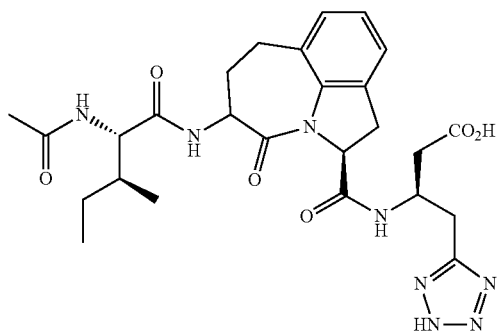 [SMILES: CC[C@H](C)[C@H](NC(C)=O)C(=O)NC1CCc2cccc3c2N(C1=O)[C@H](C(=O)N[C@@H](CC(=O)O)Cc1nn[nH]n1)C3]

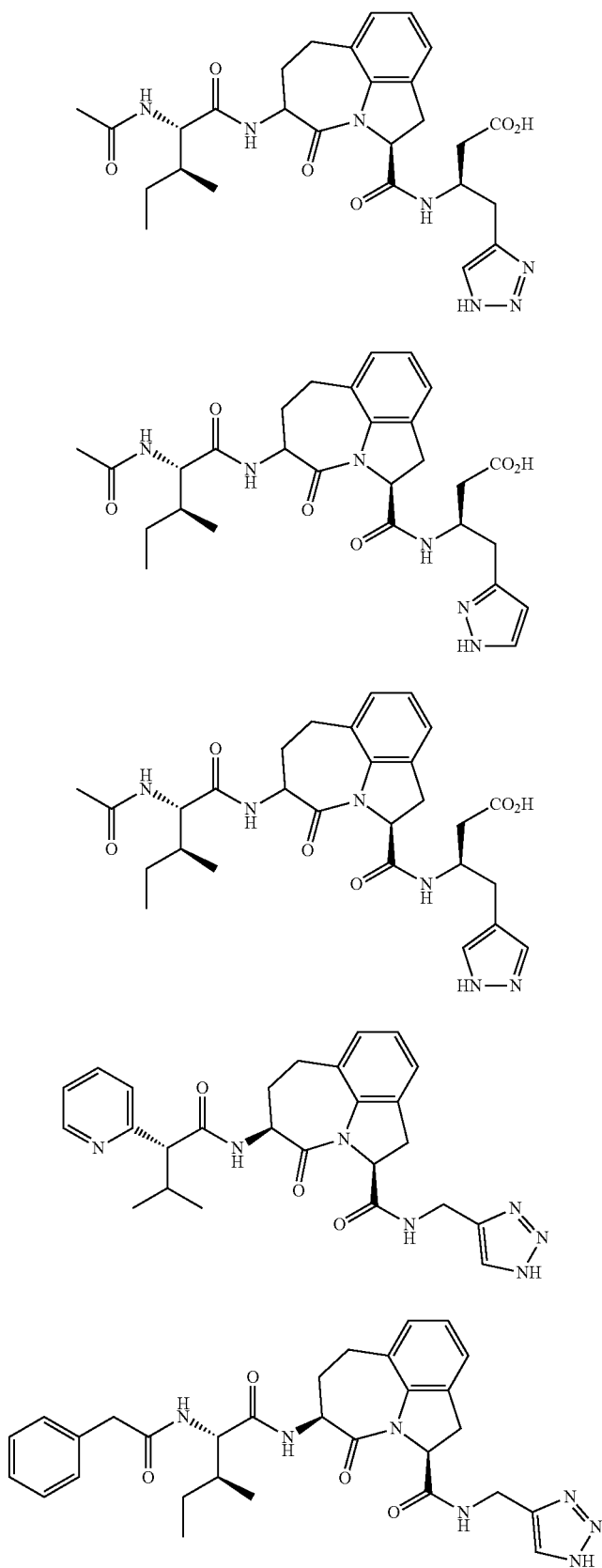

or a pharmaceutically acceptable, salt thereof.

In some embodiments:
A is an imaging agent comprising one or more of a paramagnetic ion, an x-ray imaging agent, a fluorophore, and a radioisotope;
B is an optional linking group comprising one or more alkylene groups, one or more amine groups, one or more amide groups, one or more alkyleneoxy groups, one or more thiol groups, or any combination thereof; and
C is selected from the group consisting of a polypeptide that binds granzyme B, an antibody that binds granzyme B, an antibody fragment that binds granzyme B, and a small organic molecule that binds granzyme B.

In some embodiments:
A comprises a radioisotope;
B is an optional linking group comprising one or more $C_{1-30}$ alkylene groups, one or more amine groups, one or more amide groups, one or more $C_{1-30}$ alkyleneoxy groups, one or more $C_{1-30}$ thiol groups, or any combination thereof; and
C is selected from the group consisting of a polypeptide that binds granzyme B and a small organic molecule that binds granzyme B.

In some embodiments:
A comprises a radioisotope selected from the group consisting of $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{225}Bi$, and 225Ac;
B is an optional linking group comprising one or more $C_{0-30}$ alkylene groups, one or more amide groups, one or more $C_{1-30}$ alkyleneoxy groups, or any combination thereof; and
C is selected from the group consisting of a polypeptide that binds granzyme B and a small organic molecule that binds granzyme B.

In some embodiments:
A comprises a radioisotope selected from the group consisting of $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{225}Bi$, and 225Ac;
B is an optional linking group comprising one or more —(—OCH$_2$CH$_2$)— groups; and
C is selected from the group consisting of a polypeptide that binds granzyme B and a small organic molecule that binds granzyme B.

In some embodiments, A further comprises a chelating agent. In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N', N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), and 1,4,8,11-tetraazacyclotetradecane-N,N',N'',N'''-tetraacetic acid (TETA) 1,4,7,10-tetraaza-1,4,7,10-tetra-(2-carbamoyl methyl)-cyclododecane (TCMC), and Desferioxamine B (DFO). In some embodiments, the chelating agent is selected from the group consisting of 1,4,7-triazacyclononanetriacetic acid (NOTA), 1,4,7,10-tetraazacyclododecane-1,4,7,10-tetramcetic acid (DOTA), and 1,4,7-triazacyclononane-1-glutaric acid-4,7-diacetic acid (NODAGA). In some embodiments, the chelating agent is 1,4,7-triazacyclononanetriacetic acid (NOTA).

In some embodiments, C is a polypeptide that binds granzyme B. In some embodiments, the polypeptide that binds granzyme B is from about 4 to about 100 amino acid residues in length. In some embodiments, the polypeptide that binds granzyme B is from about 4 to about 50 amino acid residues in length. In some embodiments, n the polypeptide that binds granzyme B is from about 4 to about 25 amino acid residues in length. In some embodiments, the polypeptide that binds granzyme B is from about 4 to about 15 amino acid residues in length.

In some embodiments, C is a polypeptide that binds granzyme B, wherein the polypeptide comprises an amino acid sequence having at least 90% sequence identity to:

(SEQ ID NO: 1)
$X^1-X^2-X^3-X^4-X^5-X^6-D$ wherein:
$X^1$, $X^2$, and $X^7$ are each independently selected from the group consisting of beta A, G. Q, N, S, T, Y, C, R, D, and E;
$X^4$ is selected from the group consisting of I and V;
$X^5$ is selected from the group consisting of E, G, D and S; and
$X^6$ is selected from the group consisting of E, X, P, S, T, Q, N, A, H, V, F and D.

In some embodiments, $X^4$ is I. In some embodiments, $X^5$ is E. In some embodiments, $X^6$ is F or P.

In some embodiments, the polypeptide comprises an amino acid sequence having at least 90% sequence identity to a sequence selected from the group consisting of:

```
                                                    (SEQ ID NO: 2)
        beta A-G-G-I-E-F-D;

(SEQ ID NO: 3)
        G-G-G-I-E-F-D;
        and (SEQ ID NO: 4)
        beta A-G-G-I-E-P-D.
```

In some embodiments, C is a polypeptide comprising an amino acid sequence of SEQ ID NO: 2. In some embodiments, C is a polypeptide comprising an amino acid sequence of SEQ ID NO: 3. In some embodiments, C is a polypeptide comprising an amino acid sequence of SEQ ID NO: 4.

In some embodiments, C is a polypeptide that binds granzyme B, wherein the polypeptide comprises an amino acid sequence having at least 90% sequence identity to:

```
                                                    (SEQ ID NO: 8)
        X¹-X²-X³-X⁴-X⁵-X⁶-D-X⁷
``` wherein:
- $X^1$, $X^2$, and $X^7$ are each independently selected from the group consisting of beta A, G, Q, N, S, T, Y. C, R, D, and E;
- $X^4$ is selected from the group consisting of I and V;
- $X^5$ is selected from the group consisting of E, G, D and S; and
- $X^6$ is selected from the group consisting of E, X, P, S, T, Q, N, A, H, V, F and D; and
- $X^7$ is an electrophilic group comprising the C-terminus of the amino acid sequence of SEQ ID NO: 8.

In some embodiments, $X^4$ is I. In some embodiments, $X^5$ is E. In some embodiments, $X^6$ is F or P.

In some embodiments, $X^7$ is an electrophilic group selected from the group consisting of —C(O)H, —C(O)$C_{1-6}$ alkyl, —C(O)$C_{1-6}$ haloalkyl, —C(O)$C_{1-6}$ alkoxy, —C(O)$C_{1-6}$ haloalkoxy, —C(O)—($C_{1-6}$ alkyl)-(5-10 membered heteroaryl), —C(O)—($C_{1-6}$ haloalkyl)-(5-10 membered heteroaryl), —C(O)—($C_{1-6}$ alkoxy)(5-10 membered heteroaryl), and —C(O)—$C_{1-6}$ haloalkoxy)-(5-10 membered heteroaryl). In some embodiments $X^7$ is —C(O)H.

In some embodiments, C is a small organic molecule that binds granzyme B. In some embodiments, the small organic molecule is a small molecule peptidomimetic. In some embodiments, C is a small organic molecule of Formula III:

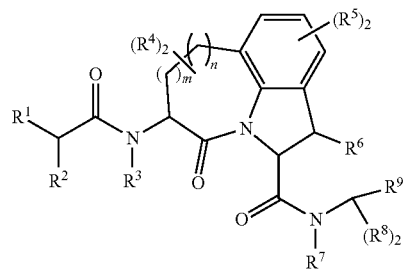

or a pharmaceutically acceptable salt thereof, wherein:
- n is 0, 1, or 2;
- m is 0, 1, or 2;
- $R^1$ and $R^2$ are each independently selected from the group consisting of: hydrogen, $C_{1-6}$ alkyl, $C_{1-6}$ alkoxy, $C_{3-6}$ cycloalkyl, $C_{6-10}$ aryl, HET, and —N($R^{10}$)$_2$, wherein each $C_{1-6}$ alkyl, $C_{1-6}$ alkoxy, $C_{3-6}$ cycloalkyl, are optionally substituted with 1, 2, or 3 substituents independently selected from the group consisting of halo and hydroxy, and each $C_{6-10}$ aryl and HET are optionally substituted with 1, 2, or 3 substituents independently selected from the group consisting of oxo, halo, hydroxy, $C_{1-4}$ alkyl, and $C_{1-4}$ haloalkyl;
- or $R^1$ and $R^2$ may come together, with the carbon atom to which they are attached, to form a 5-6 membered cycloalkyl or 5-6 heterocycloalkyl group, each of which may be optionally substituted with 1, 2, or 3 $R^{10}$ groups;
- each $R^1$ and $R^7$ is independently selected from the group consisting of hydrogen, $C_{1-4}$ alkyl, and $C_{1-4}$ haloalkyl;
- each $R^4$, $R^5$, $R^6$ and $R^8$ is independently selected from the group consisting of hydrogen, halo, hydroxy, $C_{1-4}$ alkyl, and $C_{1-4}$ haloalkyl;
- $R^9$ is HET, which may be optionally substituted with 1, 2, or 3 substituents independently selected from the group consisting of oxo, halo, hydroxy. $C_{1-4}$ alkyl, and $C_{1-4}$ haloalkyl;
- $R^{10}$ is selected from the group consisting of hydrogen, $C_{1-6}$ alkyl, and —C(O)$C_{1-4}$ alkyl, wherein the —C(O)$C_{1-4}$ alkyl is optionally substituted with —N($R^{11}$)$_2$, HET, and $C_{6-10}$ aryl, wherein the $C_{6-10}$ aryl may be optionally substituted with 1, 2, or 3 halo groups; each HET is an independently selected mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 oxo groups; and
- $R^{11}$ is selected from hydrogen, $C_{1-4}$ alkyl, and $C_{1-4}$ haloalkyl;
- with the proviso that when m is 0, then n is 0 and when n is 0, then m is 0.

In some embodiments, C is selected from the group consisting of:

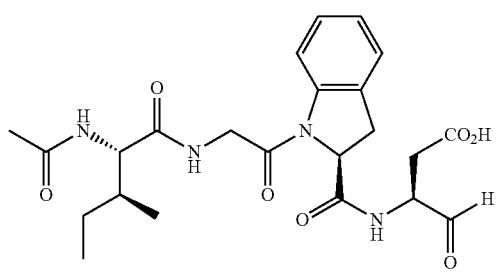 [SMILES: CC[C@H](C)[C@H](NC(C)=O)C(=O)NCC(=O)N1c2ccccc2C[C@H]1C(=O)N[C@H](C=O)CC(=O)O]

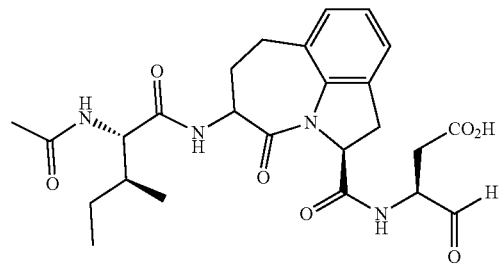 [SMILES: CC[C@H](C)[C@H](NC(C)=O)C(=O)NC1CCc2cccc3c2N(C1=O)[C@H](C(=O)N[C@H](C=O)CC(=O)O)C3]
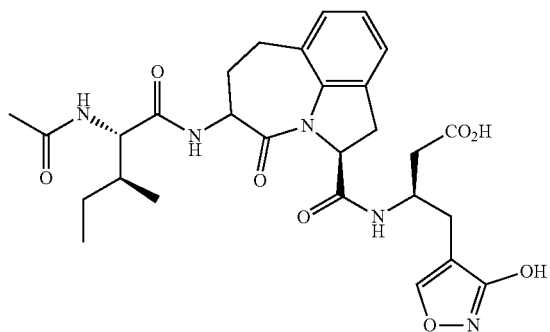 [SMILES: CC[C@H](C)[C@H](NC(C)=O)C(=O)NC1CCc2cccc3c2N(C1=O)[C@H](C(=O)N[C@@H](CC(=O)O)Cc1conc1O)C3]
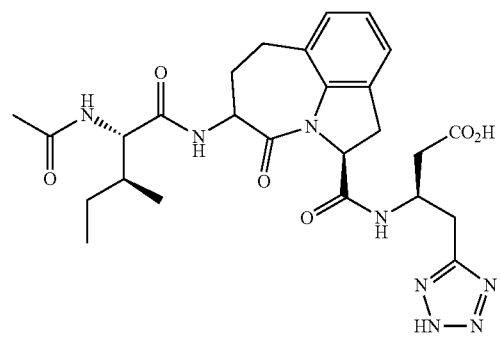 [SMILES: CC[C@H](C)[C@H](NC(C)=O)C(=O)NC1CCc2cccc3c2N(C1=O)[C@H](C(=O)N[C@@H](CC(=O)O)Cc1nn[nH]n1)C3]
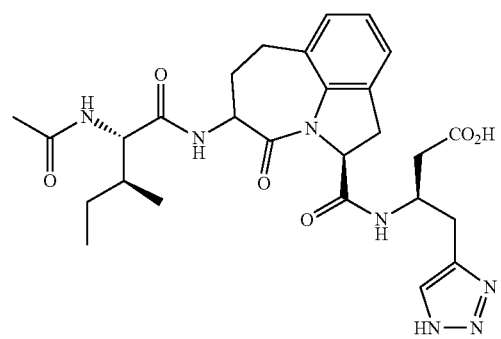 [SMILES: CC[C@H](C)[C@H](NC(C)=O)C(=O)NC1CCc2cccc3c2N(C1=O)[C@H](C(=O)N[C@@H](CC(=O)O)Cc1c[nH]nn1)C3]
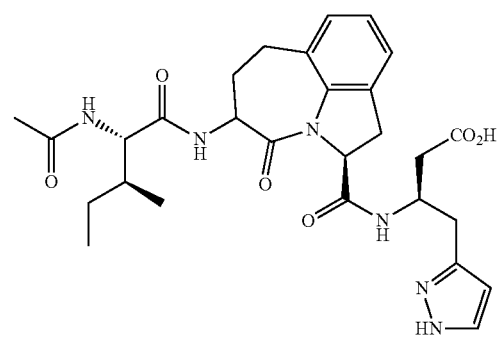 [SMILES: CC[C@H](C)[C@H](NC(C)=O)C(=O)NC1CCc2cccc3c2N(C1=O)[C@H](C(=O)N[C@@H](CC(=O)O)Cc1cc[nH]n1)C3]

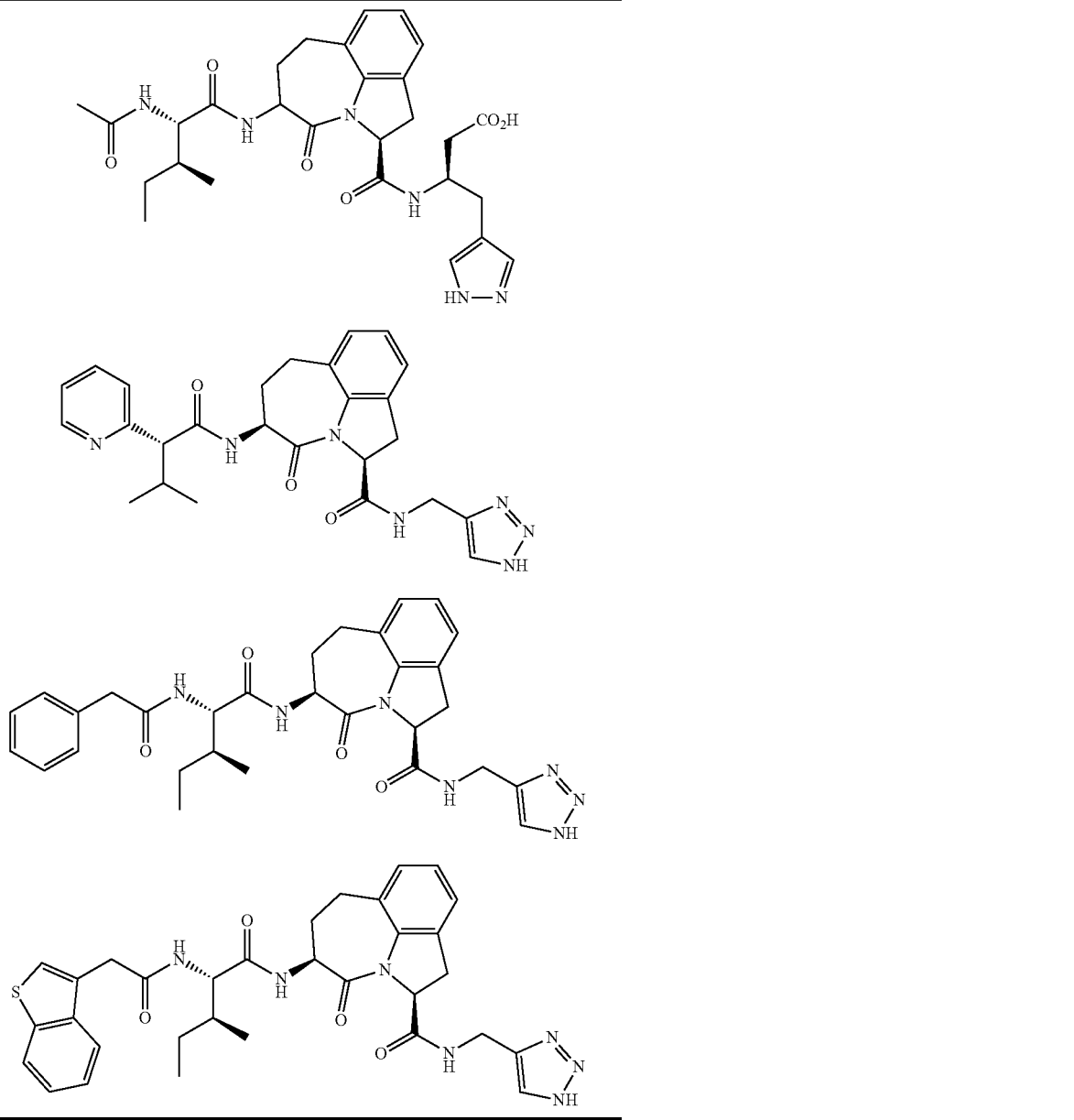

or a pharmaceutically acceptable salt thereof.

In some embodiments, C is an irreversible binder of granzyme B. In some embodiments, C is an inhibitor of granzyme B.

In some embodiments, the method further comprises administering a therapeutic agent prior to the administration of step i). In some embodiments, administration of the therapeutic agent induces an immune response cell or tissue sample or subject.

In some embodiments, the therapeutic agent is selected from the group consisting of an anti-inflammatory agent, a steroid, an immunotherapy agent, a chemotherapeutic agent, and a therapeutic antibody. In some embodiments, the therapeutic agent is a chemotherapeutic agent.

In some embodiments, the disease is selected from the group consisting of an autoimmune disorder, an inflammatory disorder, a skin disorder, cancer, and a cardiovascular disorder. In some embodiments, the disease is a cancer. In some embodiments, the cancer is selected from the group consisting of brain cancer, breast cancer, cervical cancer, colorectal cancer, lung cancer, lymphoma, melanoma, bladder cancer, renal cell carcinoma, multiple myeloma, pancreatic cancer, and prostate cancer. In some embodiments, the cancer is colon cancer. In some embodiments, the cancer is melanoma.

In some embodiments, the disease is selected from the group consisting of graft-versus-host disease, rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, rheumatic fever, post-infectious glomerulonephritis, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegene's granuloma, Sjogren's syndrome, adiposis, eosinophilic fascitis, lesions of gingiva, periodontium, alveolar bone, substantia ossea dentis, glomerulonephritis, male pattern alopecia, alopecia *senilis* by preventing epilation, alopecia *senilis* by providing hair germination and/or promoting hair generation and hair growth, muscular dystrophy, pyoderma, Sezary's syndrome, Addison's disease, ischemia-reperfusion injury of organs, transplantation disease, ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, aging, carcinogenesis, metastasis of carcinoma and hypobaropathy, histamine or leukotriene-C4 release associated diseases, Behcet's disease, autoimmune hepatitis, primary biliary cirrhosis, sclerosing cholangitis, partial liver resection, acute liver necrosis, necrosis caused by toxin, viral hepatitis, shock, anoxia, B-virus hepatitis, non-A/non-B hepatitis, cirrhosis, alcoholic cirrhosis, hepatic failure, fulminant hepatic failure, late-onset hepatic failure, acute-on-chronic liver failure, cytomegalovirus infection, HCMV infection, AIDS, senile dementia, trauma, chronic bacterial infection, malignancy of lymphoid origin, acute lymphocytic leukemia, chronic lymphocytic leukemia, acute lymphocytic lymphoma, and chronic lymphocytic lymphoma. In some embodiments, the disease is selected from the group consisting of systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegene's granulomatosis, ichthyosis, Graves ophthalmopathy, asthma, schleroderma and Sjogren's syndrome. In some embodiments, the disease is selected from the group consisting of bone marrow rejection, organ transplant rejection, and graft-versus-host disease.

In some embodiments, the compound of Formula I is selected from the group consisting of:

$^{68}$Ga-NOTA-beta A-G-G-I-E-F-D; (Compound 1; SEQ ID NO: 9)

$^{68}$Ga-NOTA-(OCH$_2$CH$_2$)$_{27}$-G-G-G-I-E-F-D; (Compound 2; SEQ ID NO: 10)
and $^{68}$Ga-NOTA-beta A-G-G-I-E-P-D. (Compound 3; SEQ ID NO: 11)

The present application further provides a compound of Formula I:

A-B—C          I or a pharmaceutically acceptable salt thereof, wherein:
A comprises one or more imaging agents;
B is an optional linking group; and
C is a group that binds granzyme B selected from the group consisting of:
a) an amino acid sequence having at least 90% sequence identity to:

$X^1-X^2-X^3-X^4-X^5-X^6-D$ (SEQ ID NO: 1)

wherein:
$X^1$, $X^2$, and $X^3$ are each independently selected from the group consisting of beta A, G, Q, N, S, T, Y, C, R, D, and E;
$X^4$ is selected from the group consisting of I and V;
$X^5$ is selected from the group consisting of E, G, D and S; and
$X^6$ is selected from the group consisting of E, X, P, S, T, Q, N, A, H, V, F and D; and
b) a compound of Formula III:

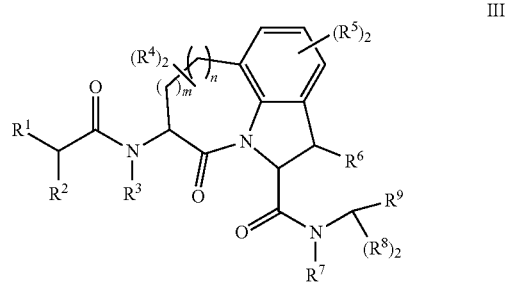

or a pharmaceutically acceptable salt thereof, wherein:
n is 0, 1, or 2;
m is 0, 1, or 2;
$R^1$ and $R^2$ are each independently selected from the group consisting of: hydrogen, $C_{1-6}$ alkyl, $C_{1-6}$ alkoxy, $C_{3-6}$ cycloalkyl, $C_{6-10}$ aryl, HET, and —N($R^{10}$)$_2$, wherein each $C_{1-6}$ alkyl, $C_{1-6}$ alkoxy, $C_{3-6}$ cycloalkyl, are optionally substituted with 1, 2, or 3 substituents independently selected from the group consisting of halo and hydroxy, and each $C_{6-10}$ aryl and HET are optionally substituted with 1, 2, or 3 substituents independently selected from the group consisting of oxo, halo, hydroxy, $C_{1-4}$ alkyl, and $C_{1-4}$ haloalkyl;

or R$^1$ and R$^2$ may come together, with the carbon atom to which they are attached, to form a 5-6 membered cycloalkyl or 5-6 heterocycloalkyl group, each of which may be optionally substituted with 1, 2, or 3 R$^{10}$ groups;

each R$^3$ and R$^7$ is independently selected from the group consisting of hydrogen, C$_{1-4}$ alkyl, and C$_{1-4}$ haloalkyl;

each R$^4$, R$^5$, R$^6$ and R$^8$ is independently selected from the group consisting of hydrogen, halo, hydroxy, C$_{1-4}$ alkyl, and C$_{1-4}$ haloalkyl;

R$^8$ is HET, which may be optionally substituted with 1, 2, or 3 substituents independently selected from the group consisting of oxo, halo, hydroxy, C$_{1-4}$ alkyl, and C$_{1-4}$ haloalkyl;

R$^{10}$ is selected from the group consisting of hydrogen, C$_{1-4}$ alkyl, and —C(O)C$_{1-4}$ alkyl, wherein the —C(O)C$_{1-4}$ alkyl is optionally substituted with —N(R$^{11}$)$_2$, HET, and C$_{6-10}$ aryl, wherein the C$_{6-10}$ aryl may be optionally substituted with 1, 2, or 3 halo groups;

each HET is an independently selected mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 oxo groups; and R$^{11}$ is selected from hydrogen, C$_{1-4}$ alkyl, and C$_{1-4}$ haloalkyl;

with the proviso that when m is 0, then n is 0 and when n is 0, then m is 0.

In some embodiments, the compound of Formula I is selected from the group consisting of:

$^{68}$Ga-NOTA-beta A-G-G-I-E-F-D; (Compound 1; SEQ ID NO: 9)

$^{68}$Ga-NOTA-(OCH$_2$CH$_2$)$_{27}$-G-G-I-E-F-D; (Compound 2; SEQ ID NO: 10)
and $^{68}$Ga-NOTA-beta A-G-G-I-E-P-D. (Compound 3; SEQ ID NO: 11)

Unless otherwise defined, all technical and scientific terms used herein have the same meaning as commonly understood by one of ordinary skill in the art to which this invention belongs. Methods and materials are described herein for use in the present invention, other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 14A shows a western blot analysis of untreated CT26 and MC38 tumors on day 12 post-tumor innoculation. FIG. 14B shows quantification of protein expression day 12, bars representing the mean of 4 replicates ±SEM. FIG. 14C shows quantification of day 12 granzyme expression for MC38 and CT26 tumors. ** P<0.005 by unpaired t test.

FIG. 17A shows a box and whiskers plot representing the mean TBRs determined by GZP PET imaging for all tumor and treatment types measured. FIG. 17B shows a bar graph comparison of granzyme B levels in saline-treated CT26 and MC38 tumors (*p<0.005). Mean TBRs were also compared across four treatment arms in CT26-bearing (FIG. 17C) and MC38-bearing mice (FIG. 17I), *p<0.05, **p<0.005 when compared to vehicle-treated mice by Welch's unpaired t test.

FIG. 19A shows a Kaplan Meier plot associating overall survival for each treatment group with average TBR for that regimen. FIG. 19B shows a plot of TBR versus percent response from each treatment regimen, $r^2$=0.91, p<0.0005 by Pearson's correlation. Each data point represents the mean TBR t SEM for each treatment arm, and dotted lines signify 95% confidence bands of the best fit line.

FIGS. 21A-21D show results of human melanoma granzyme B analysis and peptide binding described in Example 14. FIG. 21A shows human melanoma samples from patients treated with an anti-PD-1 checkpoint inhibitor, grouped as treated responders (TR) or treated nonresponders (TNR) based on modified RECIST criteria. FIG. 21B shows immunofluorescent microscopy quantification of granzyme B in 9 patients at incremental time intervals, revealing significant differences in granzyme B expression as early as 16 days post-therapy between responding and nonresponding patients. FIG. 21C shows a comparison of matched samples using either an anti-granzyme B antibody (Anti-GrB) or humanized GZP peptide (clinical GZP), revealing similar patterns of staining between the antibody and peptide that are much stronger in treated patients than untreated patients. FIG. 21D shows co-localization of human GZP (GZP Pep) and anti-GrB (GrB Ab) demonstrated in a treated responder melanoma patient, with nuclear staining (4',6-diamidino-2-phenylindole).

DETAILED DESCRIPTION

Figure 1:
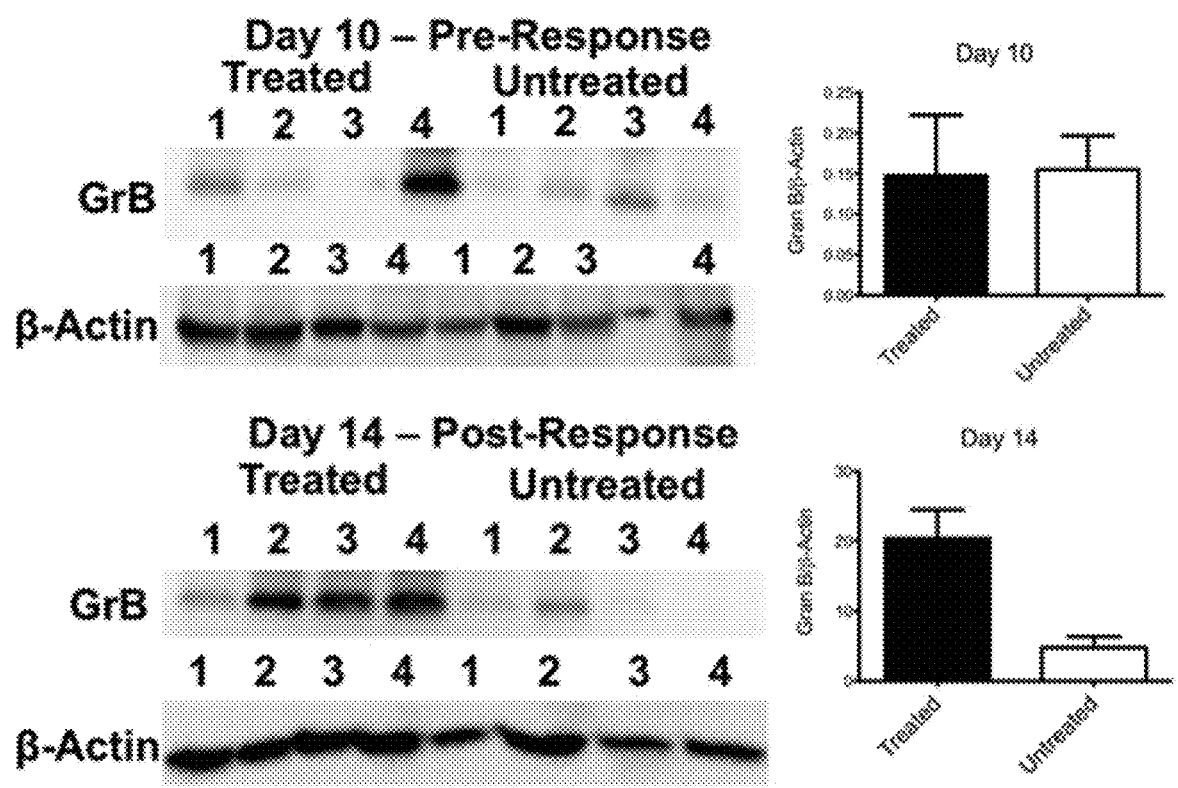
FIG. 1 shows Western blot analysis of mice treated with immunotherapy and untreated mice.

Cancer immunotherapies have represented a significant advance in cancer therapy over recent years. Antibodies directed against immune checkpoints such as programmed cell death protein 1 (PD-1) and cytotoxic t lymphocyte-associated protein 4 (CTLA-4) have been approved with positive outcomes for some patients. Research into the field of immune-oncology continues, with strategies including CAR-T cells, vaccines, small molecules, and antibodies under development. Despite the promise of these therapies, they are not a panacea. These immunotherapies can be associated with significant adverse events, which are costly, and the response rates are typically 20-50%, meaning the majority of patients do not respond to therapy. Furthermore, determining an individual patient's response to therapy can be challenging using conventional methods, as response is frequently associated with an immune-cell infiltrate that can make responding tumors appear to grow on anatomic imaging (e.g., CT, MRI), and demonstrate increased avidity with FDG-PET imaging due to the influx of metabolically active immune cells. Given the constraints of current imaging technologies, clinical studies for cancer immunotherapies typically employ overall survival as their study endpoint as opposed to progression-free survival.

Granzyme B, a downstream marker of cytotoxic T-cell activity, could serve as a novel biomarker to assess cancer immunotherapy efficacy. Granzyme B expression within a tumor can be assessed not only for CTL presence or absence, but as an effector protein released by active T-cells that also integrates a measure of CTL activity, thus accounting for issues of T-cell exhaustion that make assessment of CTL presence difficult to accomplish. Accordingly, the present application provides novels granzyme-B specific imaging agents. A representative granzyme B imaging agent has been tested in models of cancer immunotherapy. The present application describes that granzyme B imaging can also be used to predict response to cancer immunotherapy.

Compounds

The present application provides, inter alia, a compound of Formula I:

$$\text{A-B—C} \qquad \qquad \text{I}$$

or a pharmaceutically acceptable salt thereof, wherein:
A comprises one or more imaging agents;
B is an optional linking group; and
C is a group that binds granzyme B.

In some embodiments, C is an irreversible binder of granzyme B. In some embodiments, C is an inhibitor of granzyme B.

In some embodiments, the compound of Formula I is a compound of Formula I-a:

$$\text{A-C} \qquad \qquad \text{I-a}$$

or a pharmaceutically acceptable salt thereof, wherein:
A comprises one or more imaging agents; and
C is a group that binds granzyme B.

In some embodiments, C is selected from the group consisting of a polypeptide that binds granzyme B, an antibody that binds granzyme B, an antibody fragment that binds granzyme B, and a small organic molecule that binds granzyme B.

In some embodiments, C is selected from the group consisting of:
a) a polypeptide that binds granzyme B; and
b) a small organic molecule that binds granzyme B.

In some embodiments, C is selected from the group consisting of:
a) a polypeptide that binds granzyme B, wherein the polypeptide comprises an amino acid sequence having at least 90% sequence identity to:

$$X^1\text{-}X^2\text{-}X^3\text{-}X^4\text{-}X^5\text{-}X^6\text{-}D$$

(SEQ ID NO: 1)

$X^1$, $X^2$, and $X^3$ are each an independently selected amino acid (e.g., a natural or non-natural amino acid).
$X^4$ is selected from the group consisting of I and V;

$X^5$ is selected from the group consisting of E, G, D and S; and
$X^6$ is selected from the group consisting of P, S. T, Q, N, A, H, V, and D;
and
b) a compound of Formula III:

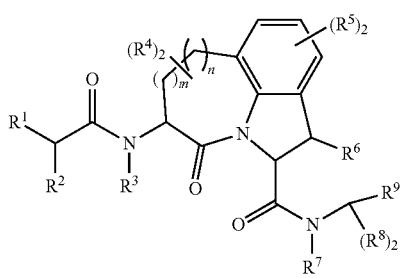

III or a pharmaceutically acceptable salt thereof, wherein:
n is 0, 1, or 2;
m is 0, 1, or 2;
$R^1$ and $R^2$ are each independently selected from the group consisting of: hydrogen, $C_{1-6}$ alkyl, $C_{1-6}$ alkoxy, CM cycloalkyl, $C_{6-10}$ aryl, HET, and —$N(R^{10})_2$, wherein each $C_{1-6}$ alkyl, $C_{1-6}$ alkoxy, $C_{3-6}$ cycloalkyl, are optionally substituted with 1, 2, or 3 substituents independently selected from the group consisting of halo and hydroxy, and each $C_{6-10}$ aryl and HET are optionally substituted with 1, 2, or 3 substituents independently selected from the group consisting of oxo, halo, hydroxy, $C_{1-4}$ alkyl, and $C_{1-4}$haloalkyl;
or $R^1$ and $R^2$ may come together, with the carbon atom to which they are attached, to form a 5-6 membered cycloalkyl or 5-6 heterocycloalkyl group, each of which may be optionally substituted with 1, 2, or 3 $R^{10}$ groups;
each $R^3$ and $R^7$ is independently selected from the group consisting of hydrogen, $C_{1-4}$ alkyl, and $C_{1-4}$ haloalkyl;
each $R^4$, $R^5$, $R^6$ and $R^8$ is independently selected from the group consisting of hydrogen, halo, hydroxy, $C_{1-4}$ alkyl, and $C_{1-4}$haloalkyl;
$R^9$ is HET, which may be optionally substituted with 1, 2, or 3 substituents independently selected from the group consisting of oxo, halo, hydroxy, $C_{1-4}$ alkyl, and $C_{1-4}$ haloalkyl;
$R^{10}$ is selected from the group consisting of hydrogen, $C_{1-4}$ alkyl, and —$C(O)C_{1-4}$ alkyl, wherein the —$C(O)C_{1-4}$ alkyl is optionally substituted with —$N(R^{11})_2$, HET, and $C_{6-10}$ aryl, wherein the $C_{6-10}$ aryl may be optionally substituted with 1, 2, or 3 halo groups;
each HET is an independently selected mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 oxo groups; and
$R^{11}$ is selected from hydrogen, $C_{1-4}$ alkyl, and $C_{1-6}$ haloalkyl;
with the proviso that when m is 0, then n is 0 and when n is 0, then m is 0.

In some embodiments, A comprises one or more imaging agents selected from the group consisting of a paramagnetic ion, an x-ray imaging agent, a fluorophore, and a radioisotope. In some embodiments, A comprises 1, 2, or 3 imaging agents selected from the group consisting of a paramagnetic ion, an x-ray imaging agent, a fluorophore, and a radioisotope. In some embodiments, A comprises one imaging agent. In some embodiments, A comprises two imaging agents. In some embodiments, A comprises three imaging agents.

In some embodiments, A comprises one or mom imaging agents which can include one or more independently selected paramagnetic ions. In some embodiments, each of the paramagnetic ions are independently selected from the group consisting of chromium (I), manganese (II), iron (I), iron (II), cobalt (II), nickel (II), copper (II), neodymium (III), samarium (III), ytterbium (III), gadolinium (III), vanadium (II), terbium (III), dysprosium (I), holmium (III), and erbium (I). In some embodiments, A comprises 1, 2, or 3 independently selected paramagnetic ions. In some embodiments, the one or more independently paramagnetic ions are independently directly or indirectly (e.g., through a chelator) bound to the compounds provided herein.

In some embodiments, A comprises one or more imaging agents which are independently selected x-ray imaging agents. In some embodiments, each of the x-ray imaging agents are independently selected from the group consisting of lanthanum (1l), gold (I), lead (U), bismuth (Ill), and iodinated x-ray imaging agents (e.g, diatrizoate, ioxaglate, metrizoate, iopamidol, iohexol, ioxilan, iopromide, iodixanol, and ioversol). In some embodiments, A comprises 1, 2, or 3 independently selected x-ray imaging agents.

In some embodiments, A comprises one or more imaging agents which include one or more independently selected radioisotopes. In some embodiments, the radioisotopes provided herein are useful as imaging agents in one or more of the methods provided herein. In addition, one or more of the radioistopes provided herein may also be useful in one or more therapeutic applications, for example, when administered to a subject in a therapeutically effective amount. For example, $^{131}$I and $^{64}$Cu may be useful as imaging agents (e.g., as non-toxic and/or non-therapeutic radioisotopes) when administered to the subject at low concentrations (e.g., 5 mCi) and may also be useful as therapeutic agents (i.e., as toxic radioisotopes and/or therapeutic radioisotopes) when administered to the subject at a higher concentration. In some embodiments, each of the radioisotopes are independently selected from the group consisting of $^{3}$H, $^{11}$C, $^{14}$C, $^{18}$F, $^{32}$P, $^{35}$S, $^{36}$Cl, $^{51}$Cr, $^{52}$Fe, $^{57}$Co, $^{58}$Co, $^{59}$Fe, $^{64}$Cu, $^{67}$Cu, $^{67}$Ga, $^{68}$Ga, $^{75}$Se, $^{76}$Br, $^{77}$Br, $^{89}$Zr, $^{90}$Y, $^{99m}$Tc, $^{111}$In, $^{123}$I, $^{124}$I, $^{125}$I, $^{131}$I, $^{152}$Eu, $^{153}$Sm, $^{166}$Ho, $^{177}$Lu, $^{186}$Re, $^{188}$Re, $^{201}$Tl, $^{203}$Pb, $^{210}$At, $^{211}$At, $^{212}$Bi, $^{225}$Bi, and 225Ac. In some embodiments, the one or more independently radioisotopes are independently directly or indirectly (e.g., through a chelator) bound to the compounds provided herein.

In some embodiments, A is an imaging agent selected from the group consisting of a positron emission tomography (PET) imaging agent, a single-photon emission computed tomography (SPECT) imaging agent, and a computed tomography imaging agent. In some embodiments, A is a PET or SPECT imaging agent. In some embodiments, A is a PET imaging agent. In some embodiments, A is a SPECT imaging agent. In some embodiments, A is a computed tomography imaging agent. In some embodiments, A is a radioisotopic computed tomography imaging agent.

In some embodiments, A is a PET or SPECT imaging agent comprising one or more radioisotopes selected from the group consisting of $^{3}$H, $^{11}$C, $^{14}$C, $^{18}$F, $^{35}$S, $^{52}$Fe, $^{58}$Co, $^{64}$Cu, $^{68}$Ga, $^{76}$Br, $^{77}$Br, $^{89}$Zr, $^{111}$In, $^{123}$I, $^{124}$I, $^{125}$I, $^{131}$I, $^{186}$Re, $^{188}$Re, $^{201}$Tl. In some embodiments, A is a PET or SPECT imaging agent comprising 1, 2, or 3 radioisotopes selected from the group consisting of $^{3}$H, $^{11}$C, $^{14}$C, $^{18}$F, $^{35}$S, $^{52}$Fe, $^{58}$Co, $^{64}$Cu, $^{68}$Ga, $^{76}$Br, $^{77}$Br, $^{89}$Zr, $^{111}$In, $^{123}$I, $^{124}$I, $^{125}$I, $^{131}$I, $^{186}$Re, $^{188}$Re, $^{201}$Tl. In some embodiments, A is a PET or SPECT imaging agent comprising one radioisotope selected from the group consisting of $^{3}$H, $^{11}$C, $^{14}$C, $^{18}$F, $^{35}$S, $^{52}$Fe, $^{58}$Co, $^{64}$Cu, $^{68}$Ga, $^{76}$Br, $^{77}$Br, $^{89}$Zr, $^{111}$In, $^{123}$I, $^{124}$I, $^{125}$I, $^{131}$I, $^{186}$Re, $^{188}$Re, $^{201}$Tl. In some embodiments, A is a PET or SPECT imaging agent comprising $^{68}$Ga.

In some embodiments, A further comprises a chelating agent. Example chelating agents include, but are not limited to, 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), and 1,4,8,11-tetraazacyclotetradecane-N,N',N'',N'-tetraacetic acid (TETA), 1,4,7,10-tetraaza-1,4,7,10-tetra-(2-carbamoyl methyl)-cyclododecane (TCMC), and Desferrioxamine B (DFO). In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), and 1,4,8,11-tetraazacyclotetradecane-N,N',N'',N'''-tetraaceic acid (TETA), 1,4,7,10-tetruaza-1,4,7,10-tetra-(2-carbamoyl methyl)-cyclododecane (TCMC), and Desferrioxamine B (DFO). In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), and 1,4,7-triazacyclononane-1-glutaric acid-4,7-diacetic acid (NODAGA). In some embodiments, the chelating agent is 1,4,7-triazacyclononanetriacetic acid (NOTA). In some embodiments, A further comprises one or more chelating agents. In some embodiments, A further comprises 1, 2, or 3 chelating agents. In some embodiments, A further comprises one chelating agent. In some embodiments, A further comprises two chelating agents. In some embodiments, A further comprises three chelating agents.

In some embodiments, A comprises one or more imaging agents which are independently selected fluorophores. Example fluorophores include, but are not limited to Alexa 350, Alexa 430, AMCA, BODIPY 630/650, BODIPY 650/665, BODIPY-FL, BODPY-R$^{6G}$, 13BODLPY-TMR, BODLPY-TRX, cascade blue. Cy3, Cy5, 6-FAM, fluorescein isothiocyanate, HEX, 6-JOE, oregon green 488, oregon green 500, oregon green 514, quantum dots, pacific blue, REG, rhodamine green, rhodamine red, renographin, ROX, TAMRA, TET, tetramethylrhodamine, Texas Red, the Alexafluor family, Cy5, Cy5.5, Cy7, indocyanine green (ICG), and fluorescent proteins (e.g., green fluorescent protein (GFP), red fluorescent protein (RFP), and dsRED).

In some embodiments, A is a fluorophore selected from the group consisting of Alea 350, Alea 430, AMCA, BODIPY 630/650. BODIPY 650/665, BODIPY-FL, BODPY-R$^{6G}$, 13BODLPY-TMR, BODLPY-TRX, cascade blue, Cy3, Cy5, 6-FAM, fluorescein isothiocyanate, HEX, 6-JOE, oregon green 488, oregon green 500, oregon green 514, quantum dots, pacific blue. REG, rhodamine green, rhodamine red, renographin, ROX, TAMRA, TET, tetramethylrhodamine, Texas Red, AF 350, 405, AF532, AF488, AF647, AF680, AF750, Cy5, Cy5.5, Cy7, indocyanine green (ICG), green fluorescent protein (GFP), red fluorescent protein (RFP), and dsRED. In some embodiments, A comprises 1, 2, or 3 independently selected fluorophores.

In some embodiments, Bis an optional linking group comprising one or more amino acid residues. In some embodiments, Bis an optional linking group comprising about 1 to about 100 amino acid residues, for example about 1 to about 100, about 1 to about 80, about 1 to about 60, about 1 to about 40, about 1 to about 20, about 1 to about 10, about 1 to about 5, about 5 to about 100, about 5 to about 80, about 5 to about 60, about 5 to about 40, about 5 to about 20, about 5 to about 10, about 10 to about 100, about 10 to about 80, about 10 to about 60, about 10 to about 40, about 10 to about 20, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 amino acid residues.

In some embodiments, B is an optional linking group comprising one or more alkylene groups, one or more amine groups, one or more amide groups, one or more alkyleneoxy groups, one or more thiol groups, one or more carbohydrate groups, or any combination thereof. In some embodiments, B is an optional linking group comprising one or more alkylene groups, one or more amine groups, one or more amide groups, one or more alkyleneoxy groups, one or more thiol groups, or any combination thereof. In some embodiments, B is an optional linking group comprising one or more $C_{1-50}$ alkylene groups, one or more amine groups, one or more amide groups, one or more $C_{1-50}$ alkyleneoxy groups, one or more $C_{1-50}$ thiol groups, or any combination thereof. In some embodiments, B is an optional linking group comprising one or more $C_{1-30}$ alkylene groups, one or more amine groups, one or more amide groups, one or more $C_{1-30}$ alkyleneoxy groups, one or more $C_{1-30}$ thiol groups, or any combination thereof.

In some embodiments, Bis an optional linking group comprising one or more —(OCH$_2$CH$_2$)— groups. In some embodiments, B is an optional linking group of the formula —(OCH$_2$CH)$_p$—, wherein p is an integer from about 1 to about 100, for example, from about 1 to about 100, about 1 to about 80, about 1 to about 60, about 1 to about 40, about 1 to about 20, about 1 to about 10, about 1 to about 5, about 5 to about 100, about 5 to about 80, about 5 to about 60, about 5 to about 40, about 5 to about 20, about 5 to about 10, about 10 to about 100, about 10 to about 80, about 10 to about 60, about 10 to about 40, about 10 to about 20, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 amino acid residues. In some embodiments, p is an integer from about 10 to about 40. In some embodiments, p is an integer from about 20 to about 40. In some embodiments, p is an integer from about 25 to about 35.

In some embodiments, C is an antibody that bindsgranzyme B. In some embodiments. C is an antibody that binds granzyme B selected from the group consisting of Clone GB11, Clone GrB-7, and NCL-L-Gran-B. In some embodiments, the antibody that binds granzyme B is Clone GrB-7.

In some embodiments, C is an antibody fragment that binds granzyme B. In some embodiments, C is an antibody fragment selected Clone GB11, Clone GrB-7, or NCL-L-Gran-B. In some embodiments, C is an antibody fragment of Clone GrB-7.

In some embodiments, C is an antibody fragment that binds granzyme B, wherein the antibody fragment comprises an amino acid sequence that has at least 90% sequence identity (e.g., at least 95%, at least 98%, at least 99%, at least 99.5% sequence identity) to a sequence selected from the group consisting of:

GTEAAAASSCFVVAE; (SEQ ID NO: 13)

GTEAAAASACFVVAE; (SEQ ID NO: 14)

GTEAAAASSAFVVAE; (SEQ ID NO: 15)

GTEAAAASSCAVVAE; (SEQ ID NO: 16)

GTEAAAASSCFAVAE; (SEQ ID NO: 17)

GTEAAAASSCFVAAE; (SEQ ID NO: 18)

GTEAAAASSCFVVGE; (SEQ ID NO: 19)
and

GTEAAAASSCFVVAD. (SEQ ID NO: 20)

In some embodiments, C is an antibody fragment that binds granzyme B, wherein the antibody fragment is selected from the group consisting of:

GTEAAAASSCFVVAE; (SEQ ID NO: 13)

GTEAAAASACFVVAE; (SEQ ID NO: 14)

GTEAAAASSAFVVAE; (SEQ ID NO: 15)

GTEAAAASSCAVVAE; (SEQ ID NO: 16)

GTEAAAASSCFAVAE; (SEQ ID NO: 17)

GTEAAAASSCFVAAE; (SEQ ID NO: 18)

GTEAAAASSCFVVGE; (SEQ ID NO: 19)
and

GTEAAAASSCFVVAD. (SEQ ID NO: 20)

In some embodiments, C is a polypeptide that binds granzyme B (e.g., Proteinase inhibitor 9 (PI-9)). In some embodiments, C is a polypeptide that binds granzyme B and one or more proteins (e.g., two, three, four, or five proteins). In some embodiments. C is a polypeptide that binds granzyme B and one protein. In some embodiments, C is a polypeptide that binds granzyme B and SerpinP9.

In some embodiments, C is a polypeptide that binds granzyme B, wherein the polypeptide comprises an amino acid sequence having at least 90% sequence identity to:

$X^1$-$X^2$-$X^3$-$X^4$-$X^5$-$X^6$-D (SEQ ID NO: 1)

wherein:
$X^1$, $X^2$, and $X^3$ are each an independently selected amino acid (e.g., a natural or non-natural amino acid).
$X^4$ is selected from the group consisting of I and V;
$X^5$ is selected from the group consisting of E, G, D and S; and
$X^6$ is selected from the group consisting of E, X, P, S, T, Q, N, A, H, V, F and D.

In some embodiments, $X^1$, $X^2$, and $X^3$ are each independently selected from the group consisting of beta A (i.e., beta-alanine), G, Q, N, S, T, Y, C, R, D, and E. In some embodiments. $X^1$, $X^2$, and $X^3$ are each independently selected from the group consisting of beta A (i.e., beta-alanine) and G. In some embodiments, $X^1$ is beta A. In some embodiments, $X^2$ is G. In some embodiments, $X^3$ is G. In some embodiments, $X^2$ and $X^3$ are each G. In some embodiments, $X^1$ is beta A, and $X^2$ and $X^3$ are each G. In some embodiments, $X^1$, $X^2$, and $X^3$ are each G.

In some embodiments, $X^1$, $X^2$, and $X^3$ are each an independently selected uncharged hydrophilic amino acid. In some embodiments, $X^1$. $X^2$, and $X^3$ are each an independently selected uncharged hydrophilic amino acid selected from the group consisting of G, Q, N, S, and T.

In some embodiments, $X^4$ is I. In some embodiments, $X^4$ is V.

In some embodiments, $X^5$ is E. In some embodiments, $X^5$ is G. In some embodiments, $X^5$ is D. In some embodiments, $X^5$ is S.

In some embodiments, $X^6$ is P. In some embodiments, $X^6$ is S. In some embodiments, $X^6$ is T. In some embodiments, $X^6$ is Q. In some embodiments, $X^6$ is N. In some embodiments, $X^6$ is A. In some embodiments, $X^6$ is H. In some embodiments, $X^6$ is V. In some embodiments, $X^6$ is D.

In some embodiments, C is a polypeptide that bindsgranzyme B, wherein the polypeptide comprises an amino acid sequence having at least 95% sequence identity to SEQ ID NO: 1. In some embodiments, C is a polypeptide that binds granzyme B, wherein the polypeptide comprises an amino acid sequence having at least 98 sequence identity to SEQ ID NO: 1. In some embodiments, C is a polypeptide that binds granzyme B, wherein the polypeptide comprises an amino acid sequence having at least 99% sequence identity to SEQ ID NO: 1. In some embodiments, C is a polypeptide that binds granzyme B, wherein the polypeptide comprises an amino acid sequence having at least 99.5% sequence identity to SEQ ID NO: 1.

In some embodiments, the polypeptide comprises an amino acid sequence having at least 90% sequence identity to a sequence selected from the group consisting of:

beta A-G-G-I-E-F-D; (SEQ ID NO: 2)

G-G-G-I-E-F-D; (SEQ ID NO: 3)
and beta A-G-G-I-E-P-D. (SEQ ID NO: 4)

In some embodiments, the polypeptide comprises an amino acid sequence having at least 90V % sequence identity to a sequence selected from the group consisting of:

```
beta A-G-G-I-E-F-D;                              (SEQ ID NO: 2)

G-G-G-I-E-F-D;                                   (SEQ ID NO: 3)

beta A-G-G-I-E-P-D;                              (SEQ ID NO: 4)

beta A-G-G-G-I-E-P-D;                            (SEQ ID NO: 22)

beta A-G-G-T-E-A-A-A-S-S-C-F-I-E-F-D.            (SEQ ID NO: 23)
```

In some embodiments, the polypeptide comprises an amino acid sequence having at least 90% sequence identity to a sequence selected from the group consisting of:

```
beta A-G-G-G-I-E-P-D;                            (SEQ ID NO: 22)
and beta A-G-G-T-E-A-A-A-S-S-C-F-I-E-F-D.            (SEQ ID NO: 23)
```

In some embodiments, C is a polypeptide comprising an amino acid sequence having at least 90% sequence identity to SEQ ID NO. 2. In some embodiments, C is a polypeptide comprising an amino acid sequence having at least 95% sequence identity to SEQ ID NO. 2. In some embodiments, C is a polypeptide comprising an amino acid sequence having at least 98% sequence identity to SEQ ID NO. 2. In some embodiments. C is a polypeptide comprising an amino acid sequence having at least 99 sequence identity to SEQ ID NO. 2. In some embodiments, C is a polypeptide comprising an amino acid sequence having at least 99.5% sequence identity to SEQ ID NO. 2. In some embodiments, C is a polypeptide comprising an amino acid sequence of SEQ ID NO: 2.

In some embodiments, C is a polypeptide comprising an amino acid sequence having at least 90% sequence identity to SEQ ID NO. 3. In some embodiments, C is a polypeptide comprising an amino acid sequence having at least 95% sequence identity to SEQ ID NO. 3. In some embodiments, C is a polypeptide comprising an amino acid sequence having at least 98% sequence identity to SEQ ID NO. 3. In some embodiments. C is a polypeptide comprising an amino acid sequence having at least 99 sequence identity to SEQ ID NO. 3. In some embodiments, C is a polypeptide comprising an amino acid sequence having at least 99.5% sequence identity to SEQ ID NO. 3. In some embodiments, C is a polypeptide comprising an amino acid sequence of SEQ ID NO: 3.

In some embodiments, C is a polypeptide comprising an amino acid sequence having at least 90% sequence identity to SEQ ID NO. 4. In some embodiments, C is a polypeptide comprising an amino acid sequence having at least 95% sequence identity to SEQ ID NO. 4. In some embodiments, C is a polypeptide comprising an amino acid sequence having at least 98 sequence identity to SEQ ID NO. 4. In some embodiments, C is a polypeptide comprising an amino acid sequence having at least 99% sequence identity to SEQ ID NO. 4. In some embodiments, C is a polypeptide comprising an amino acid sequence having at least 99.5% sequence identity to SEQ ID NO. 4. In some embodiments, C is a polypeptide comprising an amino acid sequence of SEQ ID NO: 4.

In some embodiments, C is a polypeptide comprising an amino acid sequence having at least 90% sequence identity to SEQ ID NO. 22. In some embodiments, C is a polypeptide comprising an amino acid sequence having at least 95% sequence identity to SEQ ID NO. 22. In some embodiments, C is a polypeptide comprising an amino acid sequence having at least 9/e sequence identity to SEQ ID NO. 22. In some embodiments, C is a polypeptide comprising an amino acid sequence having at least 99% sequence identity to SEQ ID NO. 22. In some embodiments, C is a polypeptide comprising an amino acid sequence having at least 99.5% sequence identity to SEQ ID NO. 22. In some embodiments, C is a polypeptide comprising an amino acid sequence of SEQ ID NO: 22.

In some embodiments, C is a polypeptide comprising an amino acid sequence having at least 90/sequence identity to SEQ ID NO. 23. In some embodiments, C is a polypeptide comprising an amino acid sequence having at least 95% sequence identity to SEQ ID NO. 23. In some embodiments, C is a polypeptide comprising an amino acid sequence having at least 98 sequence identity to SEQ ID NO. 23. In some embodiments, C is a polypeptide comprising an amino acid sequence having at least 99% sequence identity to SEQ ID NO. 23. In some embodiments. C is a polypeptide comprising an amino acid sequence having at least 99.5% sequence identity to SEQ ID NO. 23. In some embodiments, C is a polypeptide comprising an amino acid sequence of SEQ ID NO: 23.

In some embodiments, C is a polypeptide that binds granzyme B, wherein the polypeptide comprises an amino acid sequence having at least 90% sequence identity to:

```
                                                 (SEQ ID NO: 5)
X⁴-X⁵-X⁶-D
``` wherein:
$X^4$ is selected from the group consisting of I and V;
$X^5$ is selected from the group consisting of E, G, D and S; and
$X^6$ is selected from the group consisting of E, X, P. S, T, Q. N, A, K V, F and D.

In some embodiments, $X^4$ is I. In some embodiments, $X^9$ is E. In some embodiments, $X^6$ is P or F. In some embodiments, $X^6$ is P.

In some embodiments, C is a polypeptide that binds granzyme B, wherein the polypeptide comprises an amino acid sequence having at least 95% sequence identity to SEQ ID NO: 5. In some embodiments, C is a polypeptide that binds granzyme B, wherein the polypeptide comprises an amino acid sequence having at least 98 sequence identity to SEQ ID NO: 5. In some embodiments, C is a polypeptide that binds granzyme B, wherein the polypeptide comprises an amino acid sequence having at least 99% sequence identity to SEQ ID NO: 5. In some embodiments, C is a polypeptide that binds granzyme B, wherein the polypeptide comprises an amino acid sequence having at least 99.5% sequence identity to SEQ ID NO: 5.

In some embodiments, the polypeptide comprises an amino acid sequence having at least 90% sequence identity to a sequence selected from the group consisting of:

```
                                                 (SEQ ID NO: 6)
I-E-F-D;
and
                                                 (SEQ ID NO: 7)
I-E-P-D.
```

In some embodiments, C is a polypeptide comprising an amino acid sequence having at least 90% sequence identity to SEQ ID NO. 6. In some embodiments, C is a polypeptide comprising an amino acid sequence having at least 95% sequence identity to SEQ ID NO. 6. In some embodiments, C is a polypeptide comprising an amino acid sequence having at least 98 sequence identity to SEQ ID NO. 6. In some embodiments. C is a polypeptide comprising an amino acid sequence having at least 99% sequence identity to SEQ ID NO. 6. In some embodiments, C is a polypeptide comprising an amino acid sequence having at least 99.5% sequence identity to SEQ ID NO. 6. In some embodiments, C is a polypeptide comprising an amino acid sequence of SEQ ID NO: 6.

In some embodiments, C is a polypeptide comprising an amino acid sequence having at least 90% sequence identity to SEQ ID NO. 7. In some embodiments, C is a polypeptide comprising an amino acid sequence having at least 95% sequence identity to SEQ ID NO. 7. In some embodiments, C is a polypeptide comprising an amino acid sequence having at least 98 sequence identity to SEQ ID NO. 7. In some embodiments, C is a polypeptide comprising an amino acid sequence having at least 99% sequence identity to SEQ ID NO. 7. In some embodiments, C is a polypeptide comprising an amino acid sequence having at least 99.5% sequence identity to SEQ ID NO. 7. In some embodiments, C is a polypeptide comprising an amino acid sequence of SEQ ID NO: 7.

In some embodiments, C is a polypeptide that binds granzyme B, wherein the polypeptide comprises an amino acid sequence having at least 90% sequence identity to:

$$X^1-X^2-X^3-X^4-X^5-X^6-D-X^7 \quad \text{(SEQ ID NO: 8)}$$

wherein:
$X^1$, $X^2$, and $X^7$ are each an independently selected amino acid (e.g., a natural or non-natural amino acid).
$X^4$ is selected from the group consisting of I and V;
$X^5$ is selected from the group consisting of E, G, D and S; and
$X^6$ is selected from the group consisting of E, X, P, S, T, Q, N, A, H, V, F and D; and
$X^7$ is an electrophilic group.

In some embodiments, $X^1$, $X^2$, and $X^3$ are each independently selected from the group consisting of beta A (i.e., beta-alanine), G, Q, N, S, T. Y, C, R, D, and E. In some embodiments, $X^1$, $X^2$, and $X^6$ are each independently selected from the group consisting of beta A (i.e., beta-alanine) and G. In some embodiments, $X^1$ is beta A. In some embodiments, $X^2$ is G. In some embodiments, $X^3$ is G. In some embodiments, $X^2$ and $X^3$ are each G. In some embodiments, $X^1$ is beta A, and $X^2$ and $X^6$ are each G. In some embodiments, $X^1$, $X^2$, and $X^3$ are each G.

In some embodiments, $X^1$, $X^2$, and $X^3$ are each an independently selected uncharged hydrophilic amino acid. In some embodiments, $X^1$, $X^2$, and $X^3$ are each an independently selected uncharged hydrophilic amino acid selected from the group consisting of G, Q, N, S, and T.

In some embodiments, $X^6$ is I. In some embodiments, $X^6$ is V.

In some embodiments, $X^5$ is E. In some embodiments, $X^5$ is G. In some embodiments, $X^5$ is D. In some embodiments, $X^5$ is S.

In some embodiments, $X^6$ is P. In some embodiments, $X^6$ is S. In some embodiments, $X^6$ is T. In some embodiments, $X^6$ is Q. In some embodiments, $X^6$ is N. In some embodiments, $X^6$ is A. In some embodiments, $X^6$ is H. In some embodiments, $X^6$ is V. In some embodiments, $X^6$ is D.

In some embodiments, $X^7$ comprises the C-terminus of the amino acid sequence of SEQ ID NO: 8. In some embodiments, $X^7$ is an electrophilic group selected from the group consisting of —C(O)H, —C(O)C$_{1-6}$ alkyl, —C(O)C$_{1-6}$ haloalkyl, —C(O)C$_{1-6}$ alkoxy, —C(O)C$_{1-4}$ haloalkoxy, —C(O)C$_{1-6}$alkyl)-(5-10 membered heteroaryl), —C(O)—(C$_{1-4}$ haloalkyl)-5-10 membered heteroaryl), —C(O)—(C$_{1-6}$ alkoxy-(5-10 membered heteroaryl), and —C(O)—(C$_{1-6}$ haloalkoxy)-(5-10 membered heteroaryl). In some embodiments, $X^7$ is —C(O)H. In some embodiments, $X^7$ is selected from the group of substituents provided in Column A of Table 1.

In some embodiments, C is a polypeptide comprising an amino acid sequence having at least 95% sequence identity to SEQ ID NO. S. In some embodiments, C is a polypeptide comprising an amino acid sequence having at least 98% sequence identity to SEQ ID NO. 8. In some embodiments, C is a polypeptide comprising an amino acid sequence having at least 99% sequence identity to SEQ ID NO. 8. In some embodiments, C is a polypeptide comprising an amino acid sequence having at least 99.5% sequence identity to SEQ ID NO. S. In some embodiments, C is a polypeptide comprising an amino acid sequence of SEQ ID NO: 8.

In some embodiments, C is a polypeptide that binds granzyme B, wherein the polypeptide comprises an amino acid sequence having at least 90% sequence identity to:

$$X^4-X^5-X^6-D-X^7 \quad \text{(SEQ ID NO: 21)}$$

wherein:
$X^1$, $X^2$, and $X^6$ are each an independently selected amino acid (e.g., a natural or non-natural amino acid).
$X^4$ is selected from the group consisting of I and V;
$X^5$ is selected from the group consisting of E, G, D and S; and
$X^6$ is selected from the group consisting of E, X, P. S, T, Q, N, A, H, V, F and D; and
$X^6$ is an electrophilic group.

In some embodiments, $X^1$, $X^2$, and $X^3$ are each independently selected from the group consisting of beta A (i.e., beta-alanine), G, Q, N, S, T, Y, C, R, D, and E. In some embodiments. $X^1$, $X^2$, and $X^3$ are each independently selected from the group consisting of beta A (i.e., beta-alanine) and G. In some embodiments, $X^1$ is beta A. In some embodiments, $X^2$ is G. In some embodiments, $X^3$ is G. In some embodiments, $X^2$ and $X^3$ are each G. In some embodiments, $X^6$ is beta A, and $X^2$ and $X^3$ are each G. In some embodiments, $X^1$, $X^2$, and $X^7$ are each G.

In some embodiments, $X^1$, $X^2$, and $X^3$ are each an independently selected uncharged hydrophilic amino acid. In some embodiments, $X^1$, $X^2$, and $X^7$ are each an independently selected uncharged hydrophilic amino acid selected from the group consisting of G, Q, N, S, and T.

In some embodiments, $X^7$ is I. In some embodiments, $X^6$ is V.

In some embodiments, $X^9$ is E. In some embodiments, $X^6$ is G. In some embodiments, $X^5$ is D. In some embodiments, $X^5$ is S.

In some embodiments, $X^6$ is P. In some embodiments, $X^6$ is S. In some embodiments, $X^6$ is T. In some embodiments, $X^6$ is Q. In some embodiments, $X^6$ is N. In some embodiments, $X^6$ is A. In some embodiments, $X^6$ is H. In some embodiments, $X^6$ is V. In some embodiments, $X^6$ is D.

In some embodiments, $X^6$ comprises the C-terminus of the amino acid sequence of SEQ ID NO: 9. In some embodiments, $X^6$ is an electrophilic group selected from the group consisting of —C(O)H, —C(O)C$_{1-6}$ alkyl, —C(O)C$_{1-6}$ haloalkyl, —C(O)C$_{1-6}$ alkoxy, —C(O)C$_{1-6}$ haloalkoxy, —C(O)—(C$_{1-6}$alkyl)-(5-10 membered heteroaryl), —C(O)—(C$_{1-6}$ haloalkyl)-(5-10 membered heteroaryl), —C(O)—(C$_{1-6}$ alkoxy)-(5-10 membered heteroaryl), and —C(O)—(C$_{1-6}$ haloalkoxy)(5-10 membered heteroaryl). In some embodiments, $X^7$ is —C(O)H. In some embodiments, $X^7$ is selected from the group of substituents provided in Column A of Table 1.

In some embodiments, C is a polypeptide comprising an amino acid sequence having at least 95% sequence identity to SEQ ID NO: 21. In some embodiments, C is a polypeptide comprising an amino acid sequence having at least 9% sequence identity to SEQ ID NO: 21. In some embodiments, C is a polypeptide comprising an amino acid sequence having at least 99% A sequence identity to SEQ ID NO: 21. In some embodiments, C is a polypeptide comprising an amino acid sequence having at least 99.5% sequence identity to SEQ ID NO: 21. In some embodiments. C is a polypeptide comprising an amino acid sequence of SEQ ID NO: 21.

In some embodiments, C is a small organic molecule that binds granzyme B. As used herein, the term "small organic molecule" refers to a low molecular weight (e.g., less than 900 daltons, less than 800 daltons, less than 700 daltons, less than 600 daltons, or less than 500 daltons) organic compound. In some embodiments, C the small organic molecule is a small molecule peptidomimetic. As used herein, the term "peptidomimetic" refers to a compound comprising one or more functional groups (e.g., amine, amide, carboxy, aldehyde, and the like) representative of a natural or synthetic amino acid sequence.

In some embodiments, C is a small organic molecule of the following structure:

[Chemical structure]

or a pharmaceutically acceptable salt thereof.

In some embodiments, C is a small organic molecule of the following structure:

[Chemical structure]

or a pharmaceutically acceptable salt thereof.

In some embodiments, C is a small organic molecule that binds granzyme B which is selected from the group of compounds provided in International Application Nos. WO 2014/153667 and WO 2003/065987, the disclosures of each of which are incorporated herein by reference in their entireties.

In some embodiments, C is a small organic molecule of Formula III:

[Chemical structure III]

or a pharmaceutically acceptable salt thereof, wherein:
n is 0, 1, or 2;
m is 0, 1, or 2;
$R^1$ and $R^2$ are each independently selected from the group consisting of: hydrogen, C$_{1-6}$ alkyl, C$_{1-6}$ alkoxy, C$_{3-6}$cycloalkyl, C$_{6-10}$ aryl, HET, and —N(R$^{10}$)$_2$, wherein each C$_{1-6}$ alkyl, C$_{1-6}$ alkoxy, C$_{3-6}$ cycloalkyl, are optionally substituted with 1, 2, or 3 substituents independently selected from the group consisting of halo and hydroxy, and each C$_{6-10}$ aryl and HET are optionally substituted with 1, 2, or 3 substituents independently selected from the group consisting of oxo, halo, hydroxy, C$_{1-4}$ alkyl, and C$_{1-4}$ haloalkyl;
or $R^1$ and $R^2$ may come together, with the carbon atom to which they are attached, to form a 5-6 membered cycloalkyl or 5-6 heterocycloalkyl group, each of which may be optionally substituted with 1, 2, or 3 $R^{10}$ groups;
each $R^3$ and $R^7$ is independently selected from the group consisting of hydrogen, C$_{1-4}$ alkyl, and C$_{1-4}$ haloalkyl;
each $R^4$, $R^5$, $R^6$ and $R^8$ is independently selected from the group consisting of hydrogen, halo, hydroxy, C$_{1-4}$ alkyl, and C$_{1-4}$ haloalkyl;
$R^9$ is HET, which may be optionally substituted with 1, 2, or 3 substituents independently selected from the group consisting of oxo, halo, hydroxy, Cia alkyl, and C$_{1-4}$ haloalkyl;
$R^{10}$ is selected from the group consisting of hydrogen, C$_{1-4}$ alkyl, and —C(O)C$_{1-4}$ alkyl, wherein the —C(O)C$_{1-4}$ alkyl is optionally substituted with —N(R$^{11}$)$_2$, HET, and C$_{6-10}$ aryl, wherein the C$_{6-10}$ aryl may be optionally substituted with 1, 2, or 3 halo groups;
each HET is an independently selected mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 oxo groups; and
$R^{11}$ is selected from hydrogen, C$_{1-4}$ alkyl, and C$_{1-4}$ haloalkyl.

In some embodiments, when m is 0, then n is 0. In some embodiments, when n is 0, then m is 0. In some embodiments, when m is 0, then n is 0 and when n is 0, then m is 0.

In some embodiments, m is 0. In some embodiments, m is 1. In some embodiments, m is 2. In some embodiments, n is 0. In some embodiments, n is 1. In some embodiments, n is 2. In some embodiments, m and n are each 0.

In some embodiments, $R^1$ and $R^2$ are each independently selected from the group consisting of hydrogen, C$_{1-6}$ alkyl, $C_{1-6}$ alkoxy, $C_{3-6}$ cycloalkyl, phenyl, HET, and —$N(R^{10})_2$, wherein each $C_{1-6}$ alkyl, $C_{1-6}$ alkoxy, $C_{3-6}$ cycloalkyl are optionally substituted with 1, 2, or 3 substituents independently selected from the group consisting of halo and hydroxy, and each phenyl and HET are optionally substituted with 1, 2, or 3 substituents independently selected from the group consisting of oxo, halo, hydroxy, $C_{1-4}$ alkyl, and $C_{1-4}$ haloalkyl.

In some embodiments, $R^1$ and $R^2$ are each independently selected from the group consisting of $C_{1-6}$ alkyl, $C_{1-6}$ alkoxy, $C_{3-6}$ cycloalkyl, phenyl, HET, and —$N(R^{10})_2$, wherein each $C_{1-6}$ alkyl, $C_{1-6}$ alkoxy, $C_{3-6}$ cycloalkyl are optionally substituted with 1, 2, or 3 substituents independently selected from the group consisting of halo and hydroxy, and each phenyl and HET are optionally substituted with 1, 2, or 3 substituents independently selected from the group consisting of oxo, halo, hydroxy, $C_{1-4}$ alkyl, and $C_{1-4}$ haloalkyl.

In some embodiments, $R^1$ and $R^2$ are each independently selected from the group consisting of $C_{1-6}$ alkyl, $C_{3-6}$ cycloalkyl, phenyl, pyridyl, 2-oxopyrrolidine and —$N(R^{10})_2$, wherein the $C_{1-6}$ alkyl and $C_{3-6}$ cycloalkyl are each optionally substituted with 1, 2, or 3 groups independently selected from the group consisting of halo and hydroxy and the phenyl, pyridyl and 2-oxopyrrolidine optionally substituted with 1, 2, or 3 groups independently selected from the group consisting of halo, hydroxy, and $C_{1-4}$ alkyl, optionally substituted with 1, 2, 3 halo groups.

In some embodiments, $R^1$ and $R^2$ are each independently selected from the group consisting of $C_{1-6}$ alkyl, $C_{3-6}$ cycloalkyl, phenyl, pyridyl, 2-oxopyrrolidine and —$N(R^{10})_2$, wherein the $C_{1-6}$ alkyl and $C_{3-6}$ cycloalkyl are each optionally substituted with 1, 2, or 3 groups independently selected from the group consisting of halo and hydroxy and the phenyl, pyridyl and 2-oxopyrrolidine optionally substituted with 1, 2, or 3 groups independently selected from the group consisting of halo, hydroxy, and $C_{1-4}$ alkyl, optionally substituted with 1, 2, 3 halo groups; and and $R^{10}$ is selected from the group consisting of hydrogen, $C_{1-4}$ alkyl, and —$C(O)C_{1-4}$ alkyl, the —$C(O)C_{1-4}$ alkyl optionally substituted with $N(R^{11})_2$, pyrrolidinyl, piperidinyl, morpholinyl, benzothiopheneyl, and phenyl, the phenyl optionally substituted with 1, 2, or 3 halo groups.

In some embodiments, $R^3$ is selected from the group consisting of H and $C_{1-4}$ alkyl. In some embodiments, $R^3$ is H.

In some embodiments, each $R^4$ is selected from the group consisting of H, halo, $C_{1-6}$ alkyl, and $C_{1-6}$ haloalkyl. In some embodiments, each $R^4$ is independently H or $C_{1-6}$ alkyl. In some embodiments, each $R^3$ is H.

In some embodiments, each $R^4$ is selected from the group consisting of H, halo, $C_{1-6}$ alkyl, and $C_{1-6}$ haloalkyl. In some embodiments, each $R^4$ is independently H or $C_{1-6}$ alkyl. In some embodiments, each $R^4$ is H.

In some embodiments, each $R^5$ is selected from the group consisting of H, halo, $C_{1-6}$ alkyl, and $C_{1-6}$ haloalkyl. In some embodiments, each $R^5$ is independently H or $C_{1-6}$ alkyl. In some embodiments, each $R^5$ is H.

In some embodiments, $R^6$ is selected from the group consisting of H and $C_{1-4}$ alkyl. In some embodiments, $R^6$ is H.

In some embodiments, each $R^7$ is selected from the group consisting of H, halo, $C_{1-6}$ alkyl, and $C_{1-6}$ haloalkyl. In some embodiments, each $R^6$ is independently H or $C_{1-6}$ alkyl. In some embodiments, each $R^8$ is H.

In some embodiments, each $R^3$, $R^4$, $R^5$, $R^6$, $R^7$ and $R^8$ is H.

In some embodiments, each HET is an independently selected monocyclic 5-6 membered heteroaryl, 8-10 membered bicyclic heteroaryl, a monocyclic 4-6 membered heterocycloalkyl, or a bicyclic 8-10 membered heterocycloalkyl group, each comprising 1, 2, 3, or 4 heteroatoms selected from O, S and N, and optionally substituted with 1 or 2 oxo groups.

In some embodiments, $R^9$ is an unsubstituted HET group. In some embodiments, $R^9$ is a HET group substituted with 1 or 2 groups independently selected from oxo, halo, hydroxy, $C_{1-4}$ alkyl, and $C_{1-4}$ haloalkyl. In some embodiments, $R^9$ is selected from the group consisting of is selected from the group consisting of pyridyl, pyrimidyl, pyrazinyl, pyridazinyl, imidazolyl, pyrazolyl, thiazolyl, oxazolyl, oxadiazolyl, isoxazolyl, 1,2,4-triazolyl, 1,2,3-triazolyl, and tetrazolyl. In some embodiments, $R^9$ is selected from the group consisting of pyridyl, pyrimidyl, pyrazinyl, pyridazinyl, imidazolyl, pyrazolyl, thiazolyl, oxazolyl, oxadiazolyl, isoxazolyl, 1,2,4-triazolyl, 1,2,3-triazolyl, and tetrazolyl, each optionally substituted with 1, 2, or 3 substituents independently selected from the group consisting of halo, hydroxy, $C_{1-4}$ alkyl, and $C_{1-4}$ haloalkyl.

In some embodiments, each HET is independently selected from the group consisting of benzimidazolyl, benzofuranyl, benzopyrazolyl, benzotriazolyl, benzothiophenyl, benzoxazolyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, tetrazolyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, tetrahydrofuranyl, and tetrahydrothienyl, each optionally substituted with 1 or 2 substituents independently selected from the group consisting of halo, oxo, hydroxy, $C_{1-4}$ alkyl, and $C_{1-4}$ haloalkyl.

In some embodiments, the compound of Formula III, or a pharmaceutically acceptable salt thereof, is a compound of Formula III-a:

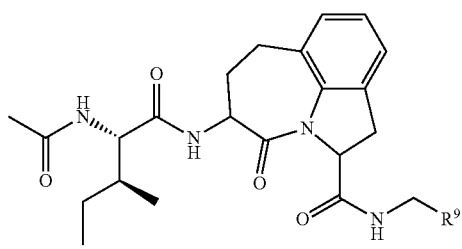

III-a or a pharmaceutically acceptable salt thereof, wherein $R^9$ is as defined above for compounds of Formula III.

In some embodiments, the compound of Formula III is selected from the group of compounds provided in Table 1, or a pharmaceutically acceptable salt thereof.

TABLE 1
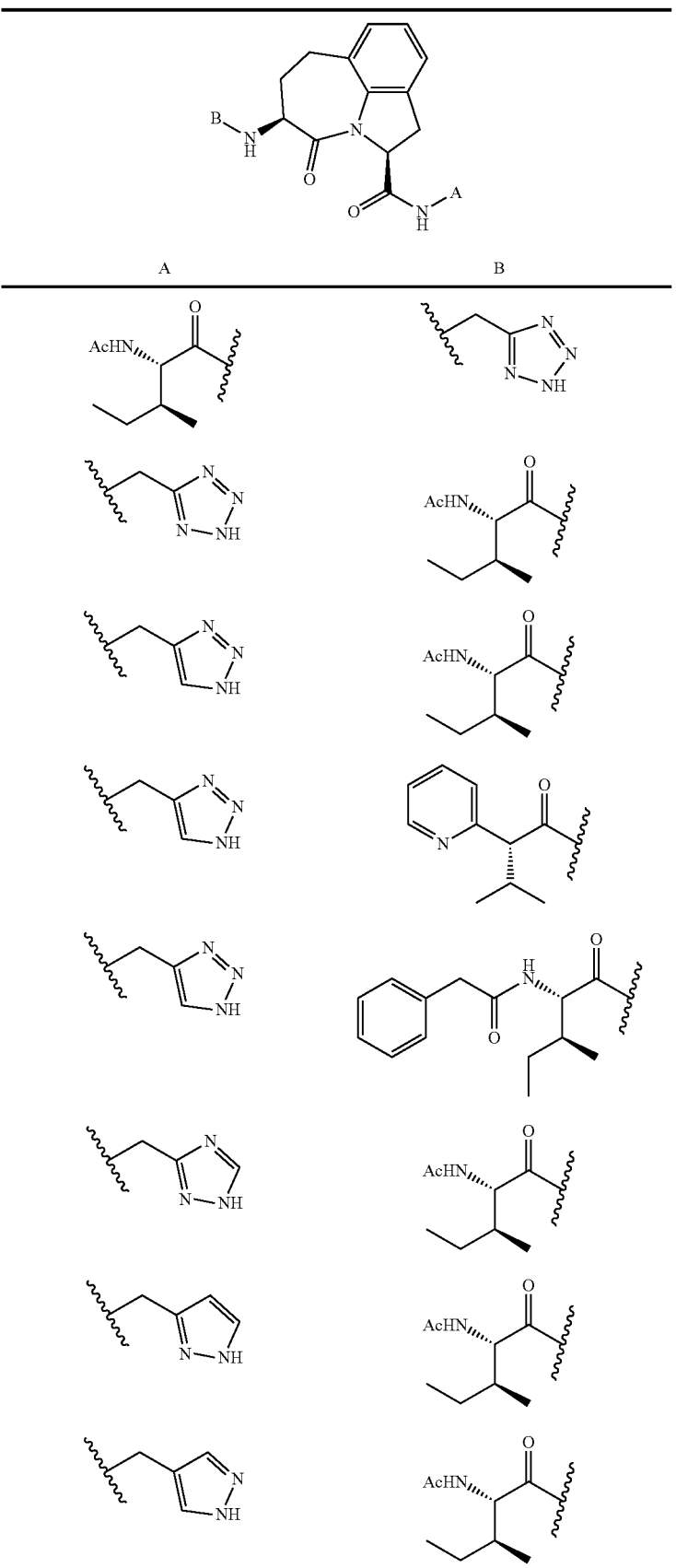

TABLE 1-continued
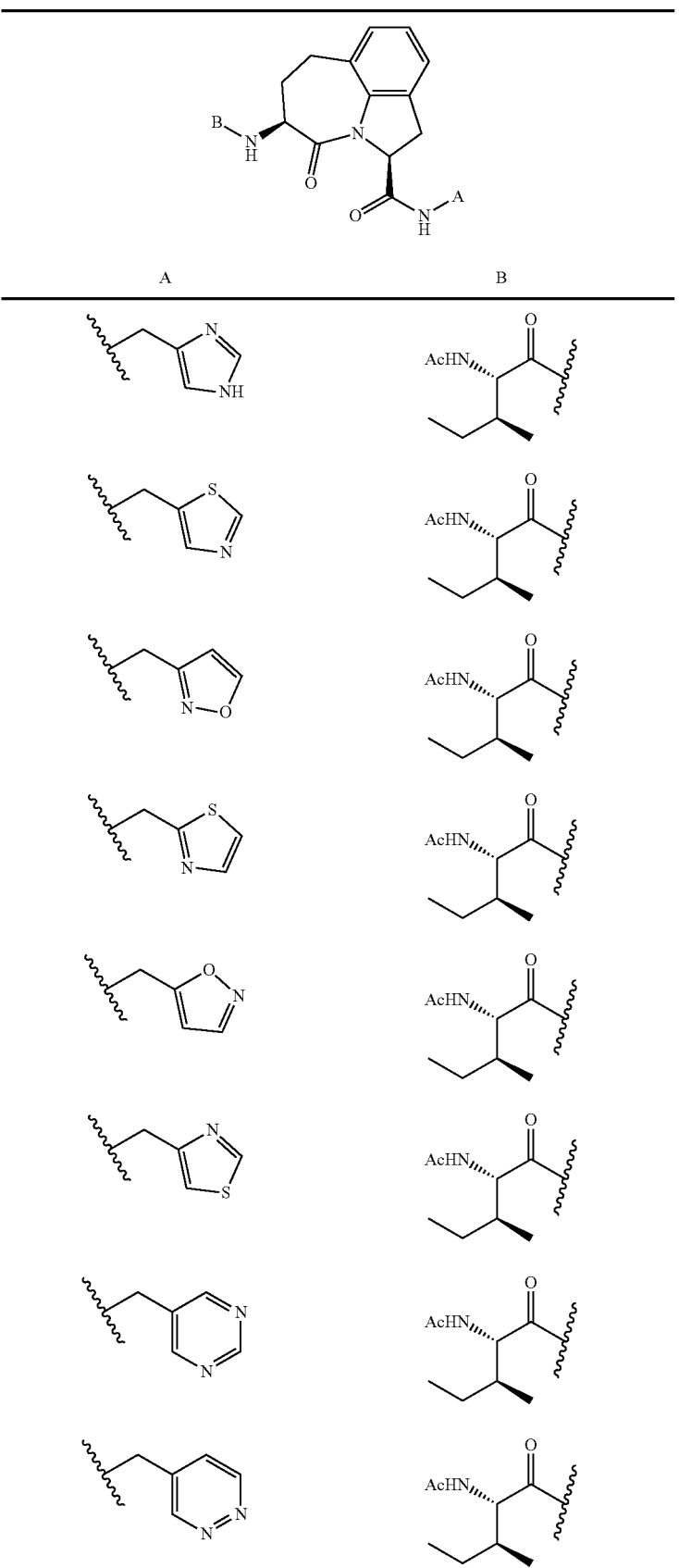

TABLE 1-continued
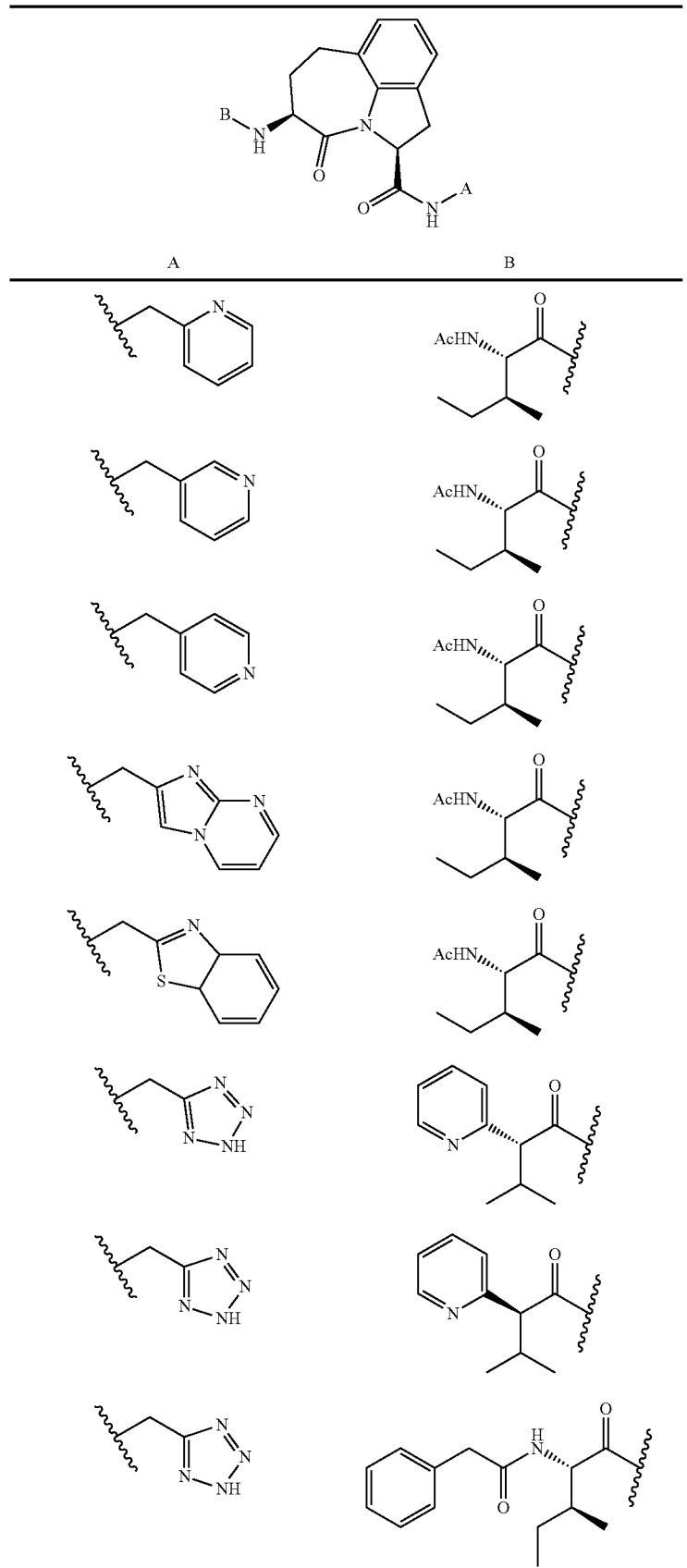

TABLE 1-continued
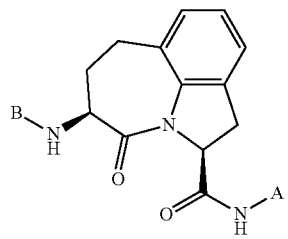
| A | B |
|---|---|
| 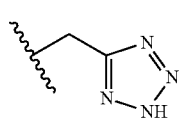 [SMILES: *Cc1nn[nH]n1] | 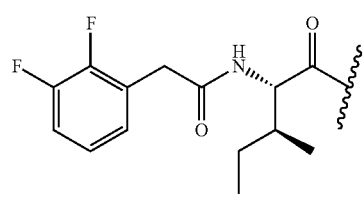 [SMILES: *C(=O)[C@@H](NC(=O)Cc1cccc(F)c1F)[C@@H](C)CC] |
| 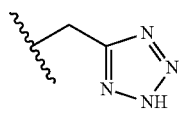 | 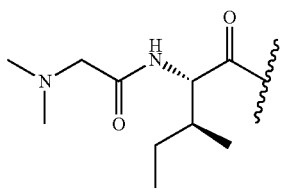 [SMILES: *C(=O)[C@@H](NC(=O)CN(C)C)[C@@H](C)CC] |
| 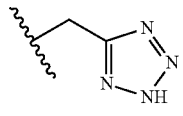 [SMILES: *Cc1nn[nH]n1] | 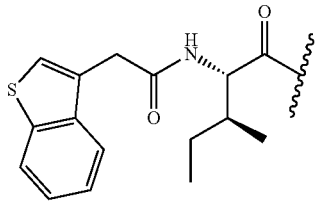 [SMILES: *C(=O)[C@@H](NC(=O)Cc1csc2ccccc12)[C@@H](C)CC] |
| 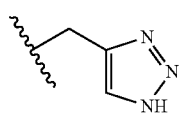 [SMILES: *Cc1c[nH]nn1] | 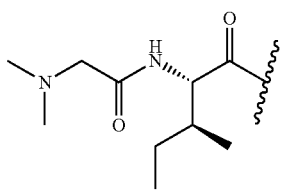 [SMILES: *C(=O)[C@@H](NC(=O)CN(C)C)[C@@H](C)CC] |
| 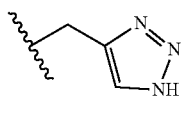 [SMILES: *Cc1c[nH]nn1] | 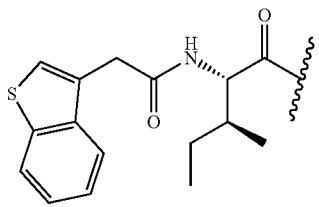 [SMILES: *C(=O)[C@@H](NC(=O)Cc1csc2ccccc12)[C@@H](C)CC] |
| 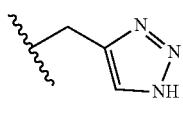 [SMILES: *Cc1c[nH]nn1] | 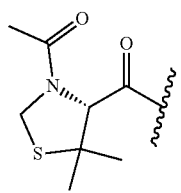 [SMILES: *C(=O)[C@H]1N(C(C)=O)CSC1(C)C] |

TABLE 1-continued
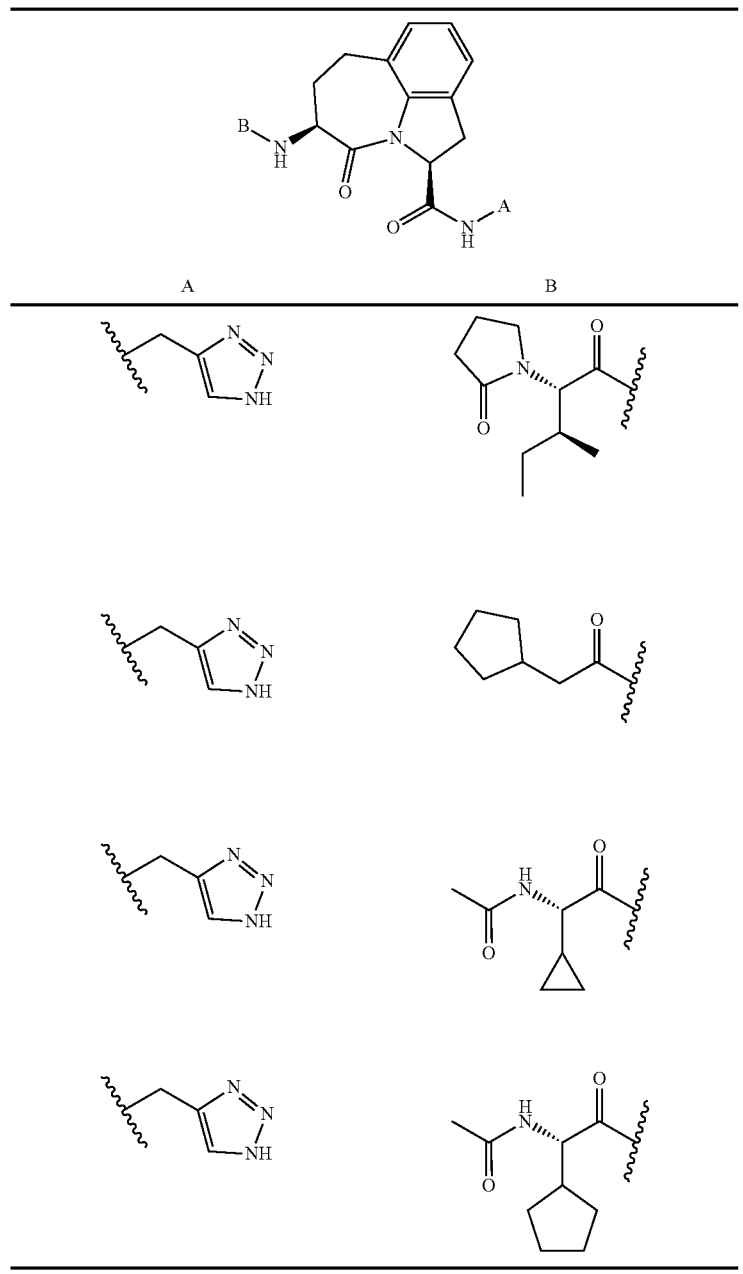
In some embodiments, the compound of Formula III is selected from the group of compounds provided in Table 2, or a pharmaceutically acceptable salt thereof:
TABLE 2
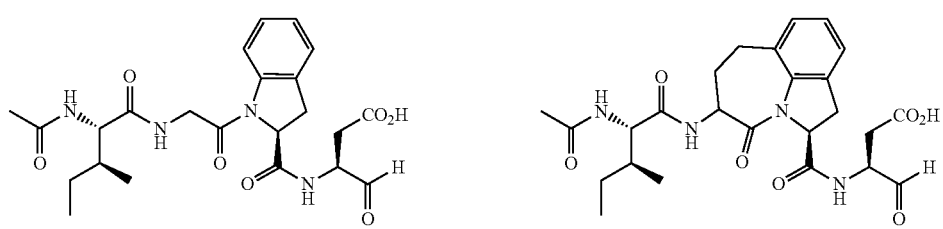

TABLE 2-continued
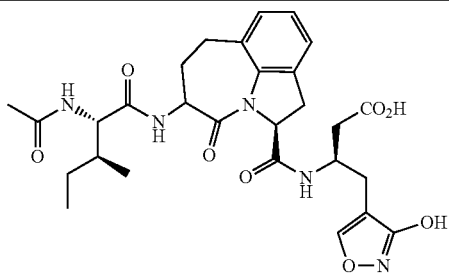 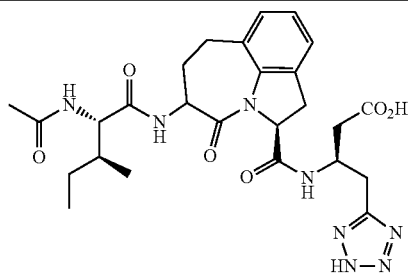
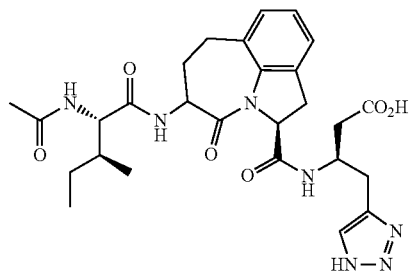 [SMILES: CC[C@H](C)[C@H](NC(C)=O)C(=O)NC1CCc2cccc3c2N(C1=O)[C@H](C(=O)N[C@@H](CC(=O)O)Cc1c[nH]nn1)C3] 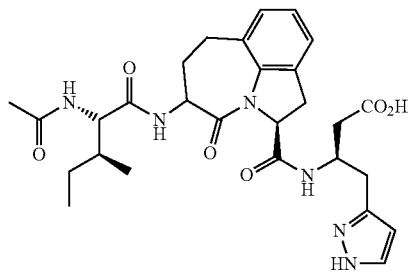
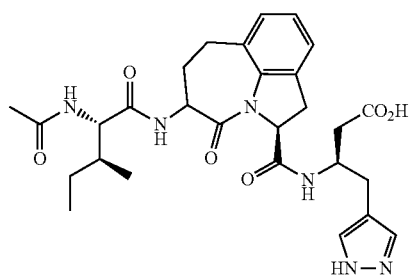 [SMILES: CC[C@H](C)[C@H](NC(C)=O)C(=O)NC1CCc2cccc3c2N(C1=O)[C@H](C(=O)N[C@@H](CC(=O)O)Cc1cn[nH]c1)C3] 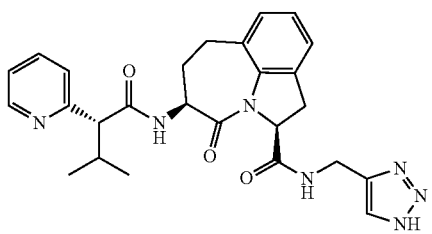 [SMILES: CC(C)[C@@H](C(=O)N[C@H]1CCc2cccc3c2N(C1=O)[C@H](C(=O)NCc1c[nH]nn1)C3)c1ccccn1]
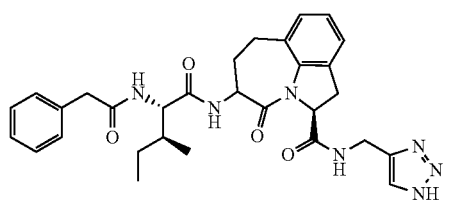 [SMILES: CC[C@H](C)[C@H](NC(=O)Cc1ccccc1)C(=O)NC1CCc2cccc3c2N(C1=O)[C@H](C(=O)NCc1c[nH]nn1)C3] 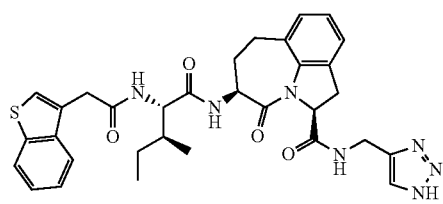 [SMILES: CC[C@H](C)[C@H](NC(=O)Cc1csc2ccccc12)C(=O)N[C@H]1CCc2cccc3c2N(C1=O)[C@H](C(=O)NCc1c[nH]nn1)C3]
In some embodiments, the compound of Formula III is selected from the group of compounds provided in Table 3, or a pharmaceutically acceptable salt thereof:
TABLE 3
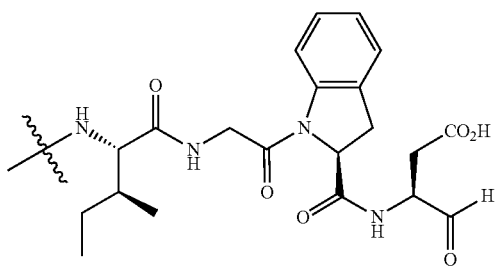 [SMILES: *N[C@H](C(=O)NCC(=O)N1c2ccccc2C[C@H]1C(=O)N[C@H](C=O)CC(=O)O)[C@@H](C)CC] 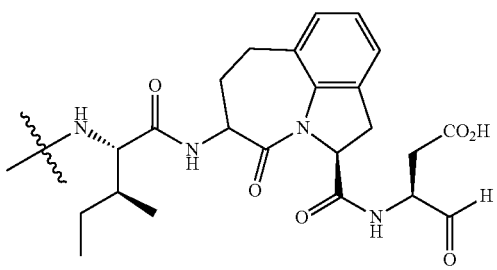 [SMILES: *N[C@H](C(=O)NC1CCc2cccc3c2N(C1=O)[C@H](C(=O)N[C@H](C=O)CC(=O)O)C3)[C@@H](C)CC]

TABLE 3-continued

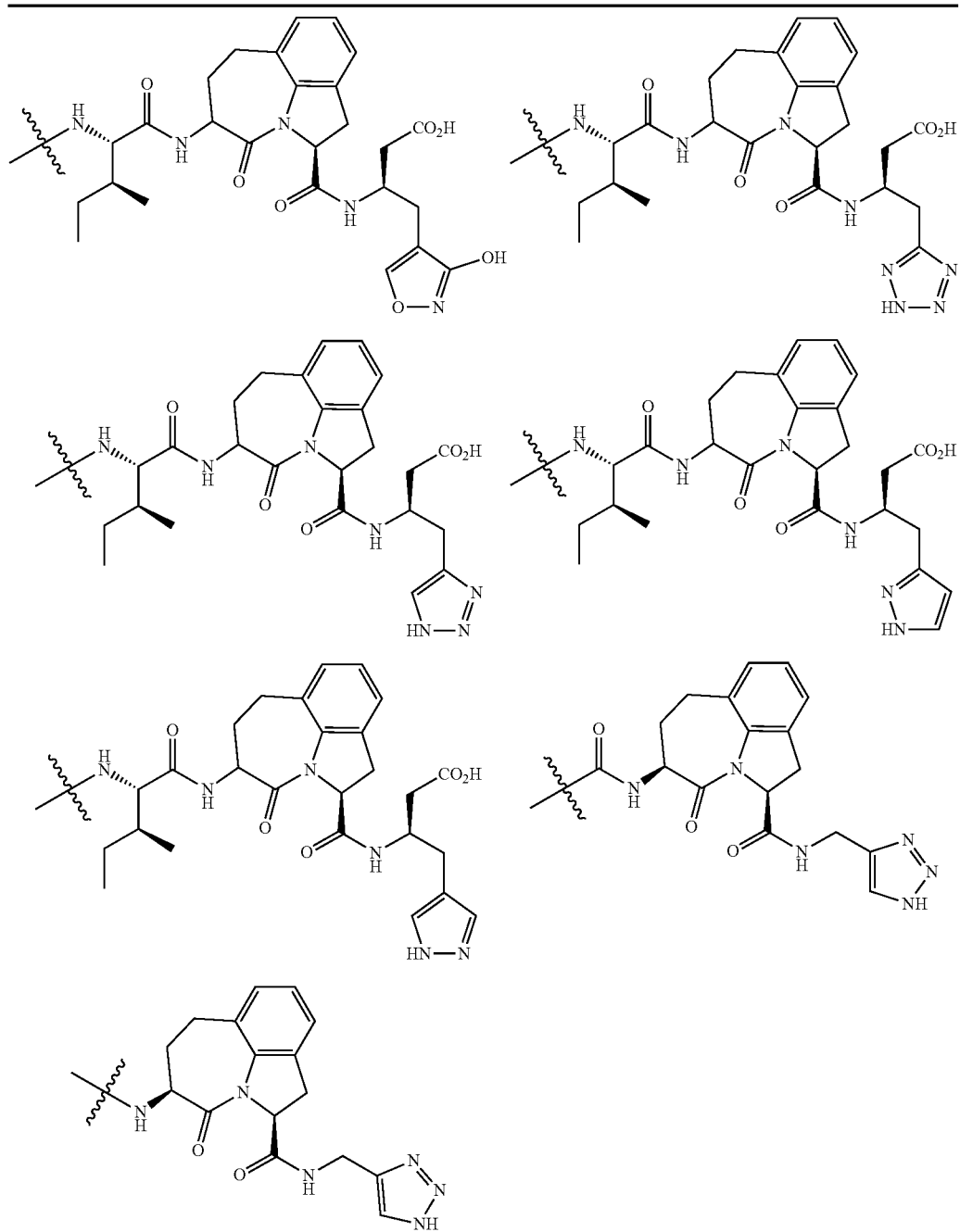

wherein ∿∿∿ indicates the bond connecting group C to the optional linker B or group A of Formula I.

In some embodiments:
- A is an imaging agent comprising one or more of a paramagnetic ion, an x-ray imaging agent, a fluorophore, and a radioisotope;
- B is an optional linking group comprising one or more alkylene groups, one or more amine groups, one or more amide groups, one or more alkyleneoxy groups, one or more thiol groups, or any combination thereof; and
- C is selected from the group consisting of a polypeptide that binds granzyme B, an antibody that binds granzyme B, an antibody fragment that binds granzyme B, and a small organic molecule that binds granzyme B.

In some embodiments:
- A comprises a radioisotope;
- B is an optional linking group comprising one or more $C_{1-30}$ alkylene groups, one or more amine groups, one or more amide groups, one or more $C_{1-30}$ alkyleneoxy groups, one or more $C_{1-30}$ thiol groups, or any combination thereof; and
- C is selected from the group consisting of a polypeptide that binds granzyme B and a small organic molecule that binds granzyme B.

In some embodiments:
A comprises a radioisotope selected from the group consisting of $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{225}Bi$, and 225Ac;

B is an optional linking group comprising one or more $C_{1-30}$ alkylene groups, one or more amide groups, one or more $C_{1-30}$ alkyleneoxy groups, or any combination thereof; and C is selected from the group consisting of a polypeptide that binds granzyme B and a small organic molecule that binds granzyme B.

In some embodiments:
A comprises a radioisotope selected from the group consisting of $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{225}Bi$, and 225Ac;

B is an optional linking group comprising one or more 4-OCH$_2$CH$_2$)— groups; and C is selected from the group consisting of a polypeptide that binds granzyme B and a small organic molecule that binds granzyme B.

In some embodiments:

A is an imaging agent comprising one or more of a paramagnetic ion, an x-ray imaging agent, a fluorophore, and a radioisotope;

B is an optional linking group comprising about 1 to about 100 amino acid residues; and C is selected from the group consisting of a polypeptide that binds granzyme B, an antibody that binds granzyme B, an antibody fragment that binds granzyme B, and a small organic molecule that binds granzyme B.

In some embodiments:

A comprises a radioisotope;

B is an optional linking group comprising about 1 to about 100 amino acid residues; and C is selected from the group consisting of a polypeptide that binds granzyme B and a small organic molecule that binds granzyme B.

In some embodiments:

A comprises a radioisotope selected from the group consisting of $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{225}Bi$, and 225Ac;

B is an optional linking group comprising about 1 to about 100 amino acid residues; and C is selected from the group consisting of a polypeptide that binds granzyme B and a small organic molecule that binds granzyme B.

In some embodiments:

A comprises a radioisotope selected from the group consisting of $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{225}Bi$, and 225Ac;

B is an optional linking group comprising about 1 to about 100 amino acid residues; and C is selected from the group consisting of a polypeptide that binds granzyme B and a small organic molecule that binds granzyme B.

In some embodiments, the compound of Formula I, or a pharmaceutically acceptable salt thereof, is a compound of Formula I-b, I-c, I-d, I-e, I-f, I-g, I-h, I-i, I-j, I-k, I-l, I-m, I-n, or I-o:

```
I-b
                                    (SEQ ID NO: 28)
A-B-beta A-G-G-I-E-F-D I-c
                                    (SEQ ID NO: 29)
A-B-G-G-G-I-E-F-D I-d
                                    (SEQ ID NO: 30)
A-B-beta A-G-G-I-E-P-D I-e
                                    (SEQ ID NO: 31)
A-B-I-E-F-D I-f
                                    (SEQ ID NO: 32)
A-B-I-E-P-D I-g
                                    (SEQ ID NO: 33)
A-beta A-G-G-I-E-F-D I-h
                                    (SEQ ID NO: 34)
A-G-G-G-I-E-F-D I-i
                                    (SEQ ID NO: 35)
A-beta A-G-G-I-E-P-D I-j
                                    (SEQ ID NO: 36)
A-I-E-F-D I-k
                                    (SEQ ID NO: 37)
A-I-E-P-D
```

I-l (SEQ ID NO: 38)

A-B-$X^1$-$X^2$-$X^3$-I-E-F-D

I-m (SEQ ID NO: 39)

A-B-$X^1$-$X^2$-$X^3$-I-E-P-D

I-n (SEQ ID NO: 40)

A-$X^1$-$X^2$-$X^3$-I-E-F-D

I-o (SEQ ID NO: 41)

A-$X^1$-$X^2$-$X^3$-I-E-P-D or a pharmaceutically acceptable salt thereof.

In some embodiments, the compound of Formula I, or a pharmaceutically acceptable salt thereof, is a compound of Formula I-p or I-q:

```
I-p
                                    (SEQ ID NO: 42)
A-B-beta A-G-G-G-T-E-A-A-A-A-S-S-C-F-I-E-F-D I-q
                                    (SEQ ID NO: 43)
A-beta A-G-G-G-T-E-A-A-A-A-S-S-C-F-I-E-F-D.
``` in some embodiments, the compound Formula is a compound selected from the group consisting of:

(Compound 1; SEQ ID NO: 9)
    $^{68}$Ga-NOTA-beta A-G-G-I-E-F-D (Compound 2; SEQ ID NO: 10)
    $^{68}$Ga-NOTA-(OCH$_2$CH$_2$)$_{27}$-G-G-G-I-E-F-D
    and (Compound 3; SEQ ID NO: 11)
    $^{68}$Ga-NOTA-beta A-G-G-I-E-P-D.

In some embodiments, the compound of Formula I is a compound selected from the group consisting of:

(Compound 1; SEQ ID NO: 9)
    $^{68}$Ga-NOTA-beta A-G-G-I-E-F-D;

(Compound 2; SEQ ID NO: 10)
    $^{68}$Ga-NOTA-(OCH$_2$CH$_2$)$_{27}$-G-G-G-I-E-F-D;

(Compound 3; SEQ ID NO: 11)
    $^{68}$Ga-NOTA-beta A-G-G-I-E-P-D;
    and (Compound 4, SEQ ID NO: 24
    $^{68}$Ga-NOTA-beta A-G-G-G-T-E-A-A-A-A-S-S-C-F-I-
    E-F-D.

In some embodiments, the compound of Formula I is $^{68}$Ga-NOTA-beta A-G-G-I-E-P-D (Compound 3; SEQ ID NO: 11).

Synthesis

As will be appreciated, the compounds provided herein, including salts thereof, can be prepared using known organic synthesis techniques and can be synthesized according to any of numerous possible synthetic routes. For example, the compounds of Formula III provided herein can be prepared according to the procedures described in U.S. patent application Ser. No. 10/503,155, the disclosure of which is incorporated herein by reference in its entirety. Once prepared, the compounds of Formula III can be covalently bonded to cep A, or optionally group B, using standard techniques in the art.

Peptide Synthesis

The compounds of Formula I provided herein comprising one or more polypeptides can be prepared, for example, using standard techniques for the preparation of peptide bonds (e.g., solid-phase synthetic techniques as described in Merrifield et al, *Journal of the American Chemical Society* 85.14 (1963): 2149-2154). Peptide synthetic techniques are well known to those of skill in the art and are described, for example, in Bodanszky et al, *Gastroenterology* 71 (1976): 965-970; Houghten, Proceedings of the National Academy of Sciences 82.15 (1985): 5131-5135; Stewart et al, Solid phase peptide synthesis. Pierce Chemical Company, 1984. Appropriate protective groups for use in such syntheses will be found in the above texts, as well as in McOmie, *Protective Groups in Organic Chemistry*, (1973):98. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

In some embodiments, polypeptides of the present application may be prepared using solid phase synthetic techniques. For example, the amino acid is attached to an inert solid support through its unprotected carboxyl or amino group. The protecting group of the amino or carboxyl group is then selectively removed and the next amino acid in the sequence having the complementary (e.g., amino or carboxyl) group suitably protected is admixed and reacted with the residue already attached to the solid support. The protecting group of the amino or carboxyl group is then removed from the newly added amino acid residue, and a further amino acid (e.g. an appropriately protected amino acid) is then added. This procedure may be repeated until the desired polypeptide length has been prepared. After the desired amino acids have been linked in the proper sequence, any remaining terminal and side group protecting groups (and solid support) can be removed sequentially or concurrently to provide the final peptide. In some embodiments, the polypeptide compounds of Formula I provided herein do not comprise a benzylated or methylbenzylated amino acid residue. Additional reactions may be necessary, as described elsewhere, to form intramolecular linkages to restrain conformation.

Linking Groups

Bifunctional cross-linking reagents have been extensively used the preparation of affinity matrices, modification and stabilization of diverse structures, identification of ligand and receptor binding sites, and structural studies. Homobifunctional reagents having two identical functional groups have been shown to be highly efficient in cross-linking identical and different polypeptides or residues of a polypeptide, and the linking of polypeptide ligands to their specific binding sites. Heterobifunctional reagents contain two different functional groups. By taking advantage of differential reactivity of the different functional groups, cross-linking can be controlled both selectively and sequentially. For example, bifunctional cross-linking reagents can be divided according to the specificity of their functional groups, including, but not limited to, amino, sulfhydryl, guanidino, indole, carboxyl specific groups. Many heterobifunctional cross-linking reagents contain a primary amine-reactive group and a thiol-reactive group.

Additional examples of heterobifunctional cross-linking reagents and methods of using the cross-linking reagents are described in U.S. Pat. No. 5,889,155, the disclosure of which is incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. Table 4 details certain hetero-bifunctional cross-linkers considered useful for preparing compounds of Formula I comprising a linking group B.

TABLE 4

| Linker | Reactive Toward | Advantages and Applications | Spacer Arm Length/ after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

Hetero-Bifunctional Crosslinkers

For compounds where a particular peptide does not contain a residue amenable for a particular cross-lining reagent in its native sequence, conservative genetic or synthetic amino acid changes in the primary sequence can be utilized.

Many appropriate imaging agents are known in the art, as are methods for their attachment to antibodies (see, for e.g., U.S. Pat. Nos. 53,021,236; 4,938,948; and 4,472,509, the disclosure of each of which is incorporated herein by reference in its entirety). Radioactively labeled compounds of Formula I provided herein may be prepared according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. In a further example, compounds of Formula I provided herein may be labeled with $^{68}$Ga by radiometalation of a bifunctional chelator provided herein (e.g., NOTA. DOTA, or NODAGA) or a similar derivative thereof.

Synthetic methods for incorporating radioisotopes into organic compounds are well known in the art, and one of ordinary skill in the art will readily recognize other methods applicable for the compounds provided herein.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II*(Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 19%); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvents boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R$^{11}$)$_n$— includes both —NR(CR'R$^{11}$)$_n$— and —(CR'R$^{11}$)$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), ter-butoxy, and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "halo" refers to F, Cl, Br, or I. In some embodiments, a halo is F, $C_1$, or Br.

As used herein, the term "$C_{n-m}$haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

As used herein, the term "hydroxy" refers to a group of formula —OH.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone— enol pairs, amide—imidic acid pairs, lactam—lactim pairs, enamine—imine pairs, and annular forms where a proton can occupy two or more positions of a heterocyclic system, for example, 1H- and 3H-imidazole, 1H—, 2H— and 4H-1,2,4-triazole, 1H— and 2H—isoindole, and 1H- and 2H-pyrazole. Tautomeric forms can be in equilibrium or sterically locked into one form by appropriate substitution.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, out Use*, Wiley-VCH 2002.

Methods of Use

The present application further provides methods of imaging granzyme B. In some embodiments, the method of imaging is performed in a cell, a tissue, a cell sample, a tissue sample, or a subject. As used herein, the term "subject," refers to any animal, including mammals and invertebrates. For example, mice, rats, other rodents, rabbits, dogs, cats, swine, cattle, sheep, horses, primates, fish, and humans. In some embodiments, the subject is a human. In some embodiments, the subject is a mouse. In some embodiments, the subject is a fish (e.g., a zebra fish). In some embodiments, the method comprises administering to the subject an effective amount of a compound provided herein (e.g., a compound of Formula I), or a pharmaceutically acceptable salt thereof. In some embodiments, the method is an in vitro method. In some embodiments, the method is an in vivo method.

The present application further provides a method of imaging granzyme B in a cell or tissue, comprising:
i) contacting the cell or tissue with a compound of Formula I:

A-B—C  I or a pharmaceutically acceptable salt thereof, and
ii) imaging the cell or tissue with a suitable imaging technique, thereby imaging granzyme B in the cell or tissue, wherein:
A comprises one or more imaging agents;
B is an optional linking group; and
C is a group that binds granzyme B.

The present application further provides a method of imaging granzyme B in a cell sample or tissue sample, comprising:
i) contacting the cell sample or tissue sample with a compound of Formula I:

A-B—C  I or a pharmaceutically acceptable salt thereof, and
ii) imaging the cell sample or tissue sample with a suitable imaging technique, thereby imaging granzyme B in the cell sample or tissue sample, wherein:
A comprises one or more imaging agents;
B is an optional linking group; and
C is a group that binds granzyme B.

The present application further provides a method of imaging granzyme B in a subject, comprising:

i) administering to the subject a compound of Formula I:

A-B—C  I or a pharmaceutically acceptable salt thereof, and
ii) imaging the subject with a suitable imaging technique, thereby imaging granzyme B in the subject, wherein:
A comprises one or more imaging agents;
B is an optional linking group; and
C is a group that binds granzyme B.

The present application further provides a method of imaging an immune response in a cell or tissue sample, comprising:
i) contacting the cell or tissue sample with a compound of Formula I:

A-B—C  I or a pharmaceutically acceptable salt thereof, and
ii) imaging the cell or tissue sample with a suitable imaging technique, thereby imaging the immune response in the cell or tissue sample, wherein:
A comprises one or more imaging agents;
B is an optional linking group; and
C is a group that binds granzyme B.

The present application further provides a method of imaging an immune response in a subject, comprising:
i) administering to the subject a compound of Formula I:

A-B—C  I or a pharmaceutically acceptable salt thereof, and
ii) imaging the subject with a suitable imaging technique, thereby imaging the immune response in the subject, wherein:
A comprises one or more imaging agents;
B is an optional linking group; and
C is a group that binds granzyme B.

The present application further provides a method of monitoring treatment of a disease in a subject, comprising:
i) administering to the subject a compound of Formula I:

A-B—C  I or a pharmaceutically acceptable salt thereof, and
ii) imaging the subject with a suitable imaging technique, wherein:
A comprises one or more imaging agents;
B is an optional linking group; and
C is a group that binds granzyme B.

The present application further provides a method of monitoring an immune response in the treatment of a disease in a subject, comprising:
i) administering to the subject a compound of Formula I:

A-B—C  I or a pharmaceutically acceptable salt thereof, and
ii) imaging the subject with a suitable imaging technique, wherein:
A comprises one or more imaging agents;
B is an optional linking group; and
C is a group that binds granzyme B.

In some embodiments, the compound of Formula I is a compound of Formula I-a:

A-C  I-a or a pharmaceutically acceptable salt thereof, wherein:
A comprises one or more imaging agents; and
C is a group that binds granzyme B.

In some embodiments, groups A, B, and C of Formula I are defined according to the definitions provided herein for compounds of Formula I. In some embodiments, the compound of Formula I is a compound of Formula I-a, I-b, I-c, I-d, I-e, I-f, I-g, I-h, I-i, I-j, I-k, I-l, I-m, I-n, or I-o, or a pharmaceutically acceptable salt thereof. In some embodiments, the compound of Formula I is a compound of Formula I-p or Formula I-q, or a pharmaceutically acceptable salt thereof.

In some embodiments, the methods provided herein further comprise waiting a time sufficient to allow the compound to accumulate at a cell or tissue site (e.g., a cell or tissue site in a subject) associated with the disease, prior to imaging. In some embodiments, the methods provided herein further comprise waiting a time sufficient to allow the compound to bind granzyme B at a cell or tissue site (e.g., a cell or tissue site in a subject) associated with the disease, prior to imaging. In some embodiments, the time sufficient is from about 30 seconds to about 24 hours, for example, about 30 seconds to about 24 hours, about 30 seconds to about 12 hours, about 30 seconds to about 6 hours, about 30 seconds to about 2 hours, about 30 seconds to about 1 hour, about 30 seconds to about 30 minutes, about 30 seconds to about 10 minutes, about 10 minutes to about 24 hours, about 10 minutes to about 12 hours, about 10 minutes to about 6 hours, about 10 minutes to about 2 hours, about 10 minutes to about 1 hour, about 10 minutes to about 30 minutes, about 30 minutes to about 24 hours, about 30 minutes to about 12 hours, about 30 minutes to about 6 hours, about 30 minutes to about 2 hours, about 30 minutes to about 1 hour, about 1 hour to about 24 hours, about 1 hour to about 12 hours, about 1 hour to about 6 hours, about 1 hour to about 2 hours, about 2 hours to about 24 hours, about 2 hours to about 12 hours, about 2 hours to about 6 hours, about 6 hours to about 24 hours, about 6 hours to about 12 hours, or about 12 hours to about 24 hours.

In some embodiments, the suitable imaging technique is a non-invasive imaging technique. In some embodiments, the suitable imaging technique is a minimally invasive imaging technique. As used herein, the term "minimally invasive imaging technique" comprises imaging techniques employing the use of an internal probe or injection of a compound or radiotracer via syringe. Example imaging techniques include, but are not limited to, fluoroscopic imaging, x-ray imaging, magnetic resonance imaging (MRI), ultrasound imaging, photoacoustic imaging, thermographic imaging, tomographic imaging, echocardiographic imaging, positron emission tomography (PET) imaging, PET with computed tomography (CT) imaging, PET-MRI, single-photon emission computed tomography (SPECT), and ultrasound imaging. In some embodiments, the suitable imaging technique is selected from the group consisting of PET imaging, PET-CT, PET-MRI, and SPECT. In some embodiments, the suitable imaging technique is selected from the group consisting of positron emission tomography (PET) imaging, positron emission tomography (PET) with computed tomography imaging, and positron emission tomography (PET) with magnetic resonance imaging (MRI). In some embodiments, the suitable imaging technique is selected positron emission tomography (PET) imaging.

In some embodiments, a disease as described herein is selected from the group consisting of an autoimmune disorder, an inflammatory disorder, a skin disorder, cancer, and a cardiovascular disorder.

In some embodiments, the disease is a cancer. In some embodiments, the cancer comprises a solid tumor. In some embodiments, the cancer is a hematological cancer (e.g., leukemia, lymphoma, and the like). In some embodiments, the cancer is selected from the group consisting of brain, breast cancer, cervical cancer, colorectal cancer, lung cancer, lymphoma, melanoma, bladder cancer, renal cell carcinoma, multiple myeloma, pancreatic cancer, and prostate cancer. In some embodiments, the cancer is selected from the group consisting of Hairy-cell leukemia, Kaposi's sarcoma, follicular lymphoma, chronic myeloid leukemia, cutaneous T-cell lymphoma, peripheral T-cell lymphoma, T-cell prolymphocytic leukemia, Classical Hodgkin's lymphoma, B-cell non-Hodgkin's lymphoma, chronic lymphocytic leukemia, acute myeloid leukemia, myelodysplastic syndrome, primary myelofibrosis, post-essential thrombocytheia myelofibrosis, post-polycythemia vera myelofibrosis, melanoma, renal cell carcinoma, prostate cancer, non-small cell lung cancer, small cell lung cancer, glioblastoma, hepatocellular carcinoma, urothelial carcinoma, esophageal carcinoma, gastroesophageal carcinoma, gastric cancer, multiple myeloma, colon cancer, rectal cancer, squamous cell carcinoma of the head and neck, epithelial ovarian cancer (EOC), primary peritoneal cancer, fallopian tube carcinoma, HER2+ breast cancer, ER+/PR+/HER2− breast cancer, triple-negative breast cancer, gastric cancer, pancreatic cancer, bladder cancer, Merkel cell cancer, nasopharyngeal cancer, adrenocortical carcinoma, meningioma, neuroblastoma, retinoblastoma, osteosarcoma, rhabdomyosarcoma, Ewing's sarcoma, liposarcoma, fibrosarcoma, leiomyosarcoma, peripheral primitive neuroectodermal tumor, squamous cell carcinoma of the cervix, squamous cell carcinoma of the vagina, and squamous cell carcinoma of the vulva. In some embodiments, the cancer is colon cancer.

In some embodiments, the disease is selected from the group consisting of graft-versus-host disease, rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, rheumatic fever, post-infectious glomerulonephritis, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis. Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegeners granuloma, Sjogren's syndrome, adiposis, eosinophilic fascitis, lesions of gingiva, periodontium, alveolar bone, substantia ossea dentis, glomerulonephritis, male pattern alopecia, alopecia *senilis* by preventing epilation, alopecia *senilis* by providing hair germination and/or promoting hair generation and hair growth, muscular dystrophy, pyoderma, Sezary's syndrome, Addison's disease, ischemia-reperfusion injury of organs, transplantation disease, ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, aging, carcinogenesis, metastasis of carcinoma and hypobaropathy, histamine or leukotriene-C4 release associated diseases, Behcets disease, autoimmune hepatitis, primary biliary cirrhosis, sclerosing cholangitis, partial liver resection, acute liver necrosis, necrosis caused by toxin, viral hepatitis, shock, anoxia, B-virus hepatitis, non-A/non-B hepatitis, cirrhosis, alcoholic cirrhosis, hepatic failure, fulminant hepatic failure, late-onset hepatic failure, acute-on-chronic liver failure, cytomegalovirus infection, HCMV infection, AIDS, senile dementia, trauma, chronic bacterial infection, malignancy of lymphoid origin, acute lymphocytic leukemia. chronic lymphocytic leukemia, acute lymphocytic lymphoma, and chronic lymphocytic lymphoma.

In some embodiments, the disease is selected from the group consisting of systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegene's granulomatosis, ichthyosis, Graves ophthalmopathy, asthma, schleroderma and Sjogren's syndrome.

In some embodiments, the disease is selected from the group consisting of bone marrow rejection, organ transplant rejection, and graft-versus-host disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a subject or individual is about 1 µg to about 2 g, for example, about 1 µg to about 2 g, about 1 µg to about 1000 mg, about 1 µg to about 500 mg, about 1 µg to about 100 mg, about 1 µg to about 50 mg, about 1 µg to about 1 mg, about 1 µg to about 500 pg, about 1 µg to about 100 µg, about 1 µg to about 10 µg, about 10 µg to about 2 g, for example, about 10 µg to about 2 g. about 10 µg to about 1000 mg, about 10 µg to about 500 mg, about 10 µg to about 100 mg, about 10 µg to about 50 mg, about 10 µg to about 1 mg, about 10 µg to about 500 µg, about 10 µg to about 100 µg, about 100 µg to about 2 g, for example, about 100 µg to about 2 g, about 100 µg to about 1000 mg, about 100 µg to about 500 mg, about 100 µg to about 100 mg, about 100 µg to about 50 mg, about 100 µg to about 1 mg, about 100 µg to about 500 µg, about 500 µg to about 2 g, for example, about 500 µg to about 2 g, about 500 µg to about 1000 mg, about 500 µg to about 500 mg, about 500 µg to about 100 mg, about 500 µg to about 50 mg, about 500 µg to about 1 mg, about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

When employed in methods of treating a disease, the compounds provided herein can be administered in combination with one or more of the additional agents provided herein. Example therapeutic agents include, but are not limited to, anti-inflammatory agents, steroids, immunotherapy agents, chemotherapeutic agents, and therapeutic antibodies.

In some embodiments, administration of the therapeutic agent induces an immune response cell or tissue sample or subject. In some embodiments, the therapeutic agent is a compound of Formula I, or a pharmaceutically acceptable salt thereof. In some embodiments, the therapeutic agent is a compound of Formula I, or a pharmaceutically acceptable salt thereof, wherein A is a radioisotope.

In some embodiments, the therapeutic agent is a compound of Formula I, or a pharmaceutically acceptable salt thereof, wherein A comprises a radioisotope (e.g., a therapeutic radioisotope). In some embodiments, the therapeutic agent is a compound of Formula I, or a pharmaceutically acceptable salt, wherein A comprises a toxic radioisotope. Examples of toxic radioisotopes include, but are not limited to, alpha emitters (e.g., $^{211}$At, $^{212}$Pb, $^{212}$Bi, $^{213}$Bi, $^{225}$Ac, $^{227}$Th,) and beta emitters (e.g., $^{90}$Y, $^{113}$I and $^{177}$Lu). In some embodiments, the toxic radioisotope is a beta emitter. In some embodiments, the toxic radioisotope is a beta emitter selected from the group consisting of $^{90}$Y, $^{131}$I and $^{177}$Lu. In some embodiments, the toxic radioisotope is an alpha emitter. In some embodiments, the toxic radioisotope is an alpha emitter selected from the group consisting of $^{211}$At, $^{212}$Pb, $^{212}$Bi, $^{213}$Bi, $^{225}$Ac, $^{227}$Th.

The present application further provides a method of treating a disease in a subject, comprising:

i) administering to the subject a first compound of Formula I:

$$A\text{-}B\text{—}C \qquad\qquad I$$

or a pharmaceutically acceptable salt thereof, wherein A comprises a non-toxic imaging agent (e.g., a non-toxic radioisotope) and B and C are defined according to the definitions provided herein for compounds of Formula I;

ii) imaging the subject with a suitable imaging technique; and iii) administering to the subject a second compound of Formula I:

$$A\text{-}B\text{—}C \qquad\qquad I$$

or a pharmaceutically acceptable salt thereof, wherein A comprises a toxic radioisotope and B and C are defined according to the definitions provided herein for compounds of Formula I, thereby treating the disease in the subject.

The present application further provides a method of treating a disease in a subject, comprising:
  i) administering to the subject a first compound of Formula I:

A-B—C      I or a pharmaceutically acceptable salt thereof wherein A comprises a non-therapeutic imaging agent (e.g., a non-therapeutic radioisotope) and B and C are defined according to the definitions provided herein for compounds of Formula I;
  ii) imaging the subject with a suitable imaging technique; and
  iii) administering to the subject a second compound of Formula I:

A-B—C      I or a pharmaceutically acceptable salt thereof, wherein A comprises a therapeutic radioisotope and B and C are defined according to the definitions provided herein for compounds of Formula I, thereby treating the disease in the subject.

In some embodiments, group A of the first compound of Formula I, or a pharmaceutically acceptable salt thereof, comprises a non-toxic radioisotope selected from the group consisting of $^{3}$H, $^{11}$C, $^{14}$C, $^{18}$F, $^{35}$S, $^{52}$Fe, $^{58}$Co, $^{64}$Cu, $^{68}$Ga, $^{76}$Br, $^{77}$Br, $^{89}$Zr, $^{111}$In, $^{123}$I, $^{124}$I, $^{125}$I, $^{131}$I, $^{186}$Re, $^{188}$Re, $^{201}$Tl.

In some embodiments, group A of the second compound of Formula I, or a pharmaceutically acceptable salt thereof, comprises a toxic radioisotope selected from the group consisting of $^{211}$At, $^{212}$Pb, $^{212}$Bi, $^{213}$Bi, $^{225}$Ac, $^{227}$Th, $^{90}$Y, $^{131}$I and $^{177}$Lu.

In some embodiments, the method further comprises determining if the first compound of Formula I, or a pharmaceutically acceptable salt thereof, binds to a cell or tissue of the subject to be treated prior to the administration of step iii). In some embodiments, the method further comprises determining if the first compound of Formula I, or a pharmaceutically acceptable salt thereof binds to granzyme B, prior to the administration of step iii).

In some embodiments, the subject has been identified and/or diagnosed as having the disease to be treated prior to the administration of step i). In some embodiments, the subject is identified and/or diagnosed as having the disease to be treated after the imaging of step ii). For example, the disease to be treated is selected from the group consisting of: an autoimmune disorder, an inflammatory disorder, a skin disorder, cancer, and a cardiovascular disorder as described herein.

In some embodiments, the subject has been treated with one or more immunotherapeutic agents prior to the administration of step i). In some embodiments, the disease has been determined to be resistant to the one or more immunotherapeutic agents administered prior to the administration of step i).

In some embodiments, the method further comprises:
  iv) administering one or more immunotherapeutic agents after the administration of the second compound of Formula I, or a pharmaceutically acceptable salt thereof. In some embodiments, steps i)-iv) are repeated multiple times.

In some embodiments, the first compound of Formula I, or a pharmaceutically acceptable salt thereof, and the second compound of Formula L or a pharmaceutically acceptable salt thereof, are the same. In some embodiments, the second compound of Formula L or a pharmaceutically acceptable salt thereof, is administered to the subject in a higher concentration compared to the amount of the first compound of Formula I, or a pharmaceutically acceptable salt thereof, administered to the subject. In some embodiments, the second compound of Formula I, or a pharmaceutically acceptable salt thereof, is administered to the subject in a lower concentration compared to the amount of the first compound of Formula I, or a pharmaceutically acceptable salt thereof, administered to the subject. In some embodiments, the second compound of Formula I, or a pharmaceutically acceptable salt thereof, is administered to the subject in about the same concentration compared to the amount of the first compound of Formula I, or a pharmaceutically acceptable salt thereof, administered to the subject.

In some embodiments, the first compound of Formula I, or a pharmaceutically acceptable salt thereof, and the second compound of Formula I, or a pharmaceutically acceptable salt thereof, are different.

In some embodiments, group A of the first compound of Formula I, or a pharmaceutically acceptable salt thereof, is the same as group A of the second compound of Formula I, or a pharmaceutically acceptable salt thereof. In some embodiments, group B of the first compound of Formula I, or a pharmaceutically acceptable salt thereof, is the same as group B of the second compound of Formula I, or a pharmaceutically acceptable salt thereof. In some embodiments, group C of the first compound of Formula L or a pharmaceutically acceptable salt thereof, is the same as group C of the second compound of Formula I, or a pharmaceutically acceptable salt thereof. In some embodiments, groups B and C of the first compound of Formula I, or a pharmaceutically acceptable salt thereof, are the same as groups B and C of the second compound of Formula I, or a pharmaceutically acceptable salt thereof. In some embodiments, groups A and B of the first compound of Formula I, or a pharmaceutically acceptable salt thereof, are the same as groups A and B of the second compound of Formula L or a pharmaceutically acceptable salt thereof. In some embodiments, groups A and C of the first compound of Formula I, or a pharmaceutically acceptable salt thereof, are the same as groups A and C of the second compound of Formula I, or a pharmaceutically acceptable salt thereof.

In some embodiments, group A of the first compound of Formula I, or a pharmaceutically acceptable salt thereof, is different than group A of the second compound of Formula I, or a pharmaceutically acceptable salt thereof. In some embodiments, group B of the first compound of Formula I, or a pharmaceutically acceptable salt thereof, is different than group B of the second compound of Formula I, or a pharmaceutically acceptable salt thereof. In some embodiments, group C of the first compound of Formula I, or a pharmaceutically acceptable salt thereof, is different than group C of the second compound of Formula I, or a pharmaceutically acceptable salt thereof. In some embodiments, groups B and C of the first compound of Formula L or a pharmaceutically acceptable salt thereof, are different than groups B and C of the second compound of Formula I, or a pharmaceutically acceptable salt thereof. In some embodiments, groups A and B of the first compound of Formula I, or a pharmaceutically acceptable salt thereof, are different than groups A and B of the second compound of Formula I, or a pharmaceutically acceptable salt thereof. In some embodiments, groups A and C of the first compound of Formula I, or a pharmaceutically acceptable salt thereof, are different than groups A and C of the second compound of Formula I, or a pharmaceutically acceptable salt thereof.

The present application further provides a method determining the likelihood that a subject having a disease will have a positive response to treatment with a therapeutic agent (e.g., a second compound of Formula I, or a pharmaceutically acceptable salt thereof), the method comprising:
i) administering to the subject a first compound of Formula I:

A-B—C                        I or a pharmaceutically acceptable salt thereof, wherein A comprises a non-therapeutic imaging agent (e.g., a non-therapeutic radioisotope) and B and C are defined according to the definitions provided herein for compounds of Formula I;
ii) imaging the subject with a suitable imaging technique; and
iii) determining if the first compound of Formula I, or a pharmaceutically acceptable salt thereof binds to a cell or tissue to be treated.

The present application further provides a method of predicting the efficacy of treatment of a therapeutic agent (e.g., a second compound of Formula L or a pharmaceutically acceptable salt thereof), the method comprising:
i) administering to the subject a first compound of Formula I:

A-B—C                        I or a pharmaceutically acceptable salt thereof, wherein A comprises a non-therapeutic imaging agent (e.g., a non-therapeutic radioisotope) and B and C are defined according to the definitions provided herein for compounds of Formula I;
ii) imaging the subject with a suitable imaging technique; and
iii) determining if the first compound of Formula I, or a pharmaceutically acceptable salt thereof binds to a cell or tissue to be treated.

In some embodiments, the method further comprises, if the first compound of Formula I, or a pharmaceutically acceptable salt thereof is determined to bind to the cell or tissue to be treated:
iv) administering to the subject a therapeutic agent, thereby treating the disease in the subject.

In some embodiments, the method further comprises, if the first compound of Formula I, or a pharmaceutically acceptable salt thereof is determined to bind to the cell or tissue to be treated:
iv) administering to the subject a second compound of Formula I:

A-B—C                        I or a pharmaceutically acceptable salt thereof, wherein A comprises a therapeutic radioisotope and B and C are defined according to the definitions provided herein for compounds of Formula I, thereby treating the disease in the subject.

In some embodiments, the disease to be treated is selected from the group consisting of an autoimmune disorder, an inflammatory disorder, a skin disorder, cancer, and a cardiovascular disorder as described herein. In some embodiments, the disease is a cancer described herein.

In some embodiments, the second compound of Formula I, or a pharmaceutically acceptable salt thereof, is administered to the subject in a therapeutically effective amount.

In some embodiments, the methods provided herein further comprise administering a therapeutic agent prior to the administration of step i). In some embodiments, the methods provided herein further comprise administering a therapeutic agent after the imaging of step ii). In some embodiments, the methods provided herein further comprise the steps of:
iii) administering a therapeutically effective amount of a therapeutic agent after the imaging of step ii); and
iv) repeating steps i) and ii) of the methods provided herein. In some embodiments, the therapeutic agent is a compound other than a compound of Formula I, or a pharmaceutically acceptable salt thereof, provided herein.

In some embodiments, steps i)-iv) are repeated multiple times.

In some embodiments, the compounds provided herein and the one or more additional therapeutic agents are administered according to a dosing regimen over a period of time. Exemplary dosing regimens include, but are not limited to, the following combinations:

A/B/A B/A/B B/B/A A/A/B
A/B/B B/A/A A/B/B/B B/A/B/B
B/B/B/A B/B/A/B A/A/B/B A/B/B/A
A/B/B/A B/B/A/A B/A/B/A B/A/A/B
A/A/A/B B/A/A/A A/B/A/A A/A/B/A wherein "A" represents administration of the compound provided herein (e.g., a compound of Formula I, or a pharmaceutically acceptable salt thereof) and "B" represents administration of the additional therapeutic agent (e.g., a compound of Formula I, or a pharmaceutically acceptable salt thereof, wherein group A comprises a toxic radioisotope and/or therapeutic radioisotope, or a therapeutic agent provided herein other than a compound of Formula I, or a pharmaceutically acceptable salt thereof). In some embodiments, the cell, cell sample, tissue, tissue sample, or subject are imaged with an appropriate imaging technique after administration of the compound provided herein.

In some embodiments, the cell, cell sample, tissue, tissue sample, or subject are imaged with an appropriate imaging technique after administration of the additional therapeutic agent.

In some embodiments, the present application provides a method of treating a disease in a subject, comprising:
i) administering to the subject a compound of Formula I:

A-B—C                        I or a pharmaceutically acceptable salt thereof, wherein A comprises a non-toxic imaging agent (e.g., a non-toxic radioisotope) and B and C are defined according to the definitions provided herein for compounds of Formula I;
ii) imaging the subject with a suitable imaging technique;
iii) administering to the subject a therapeutic agent, thereby treating the disease in the subject.

In some embodiments, the present application provides a method of treating a disease in a subject, comprising:
i) administering to the subject a compound of Formula I:

A-B—C                        I or a pharmaceutically acceptable salt thereof, wherein A comprises a non-therapeutic imaging agent (e.g., a non-therapeutic radioisotope) and B and C are defined according to the definitions provided herein for compounds of Formula I;
ii) imaging the subject with a suitable imaging technique;
iii) administering to the subject a therapeutic agent, thereby treating the disease in the subject.

In some embodiments, the method further comprises determining if the first compound of Formula I, or a pharmaceutically acceptable salt thereof, binds to a cell or tissue of the subject to be treated prior to the administration of step iii). In some embodiments, the method further comprises determining if the first compound of Formula I, or a pharmaceutically acceptable salt thereof, binds to granzyme B, prior to the administration of step iii).

In some embodiments, the subject has been identified and/or diagnosed as having the disease to be treated prior to the administration of step i). In some embodiments, the subject is identified and/or diagnosed as having the disease to be treated after the imaging of step ii).

In some embodiments, the subject has been treated with one or more immunotherapeutic agents prior to the administration of step i). In some embodiments, the disease has been determined to be resistant to the one or more immunotherapeutic agents administered prior to the administration of step i).

In some embodiments, the method further comprises:
  iv) administering one or more immunotherapeutic agents after the administration of the therapeutic agent of step iii). In some embodiments, steps i)-iv) are repeated multiple times.

In some embodiments, the additional therapeutic agent is administered to the subject in a therapeutically effective amount.

In some embodiments, the therapeutic agent is an antibody. Example antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20), antibodies directed to c-MET, and antibody inhibitors of granzyme B (e.g., Clone GB11, Clone GrB-7, and NCL-L-Gran-B), ipilimumab (anti-CTLA-4), nivolumab (anti-PD-1), pembrolizumab (anti-PD-1), atezolizumab (anti-PD-1), elotuzumab (anti-SLAM7), and daratumumab (anti-CD38).

In some embodiments, the therapeutic agent is a steroid. Example steroids include corticosteroids such as cortisone, dexamethasone, hydrocortisone, methylprednisolone, prednisolone, and prednisone. In some embodiments, the additional agent is a corticosteroid.

In some embodiments, the therapeutic agent is an anti-inflammatory compound. Example anti-inflammatory compounds include aspirin, choline salicylates, celecoxib, didofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

In some embodiments, the therapeutic agent is chemotherapeutic agent. Example chemotherapeutic agents include, but are not limited to, a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxouridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Sml1, triapine, didox, trimidox, amidox, 3-AP, MDL-101,731, bendamustine, ofatumumab, and GS-1101 (also known as CAL-101).

In some embodiments, the chemotherapeutic agent is selected from the group consisting of an alkylating agent (e.g., busulfan, chlorambucil, cisplatin, cyclophosphamide (cytoxan), dacarbazine, ifosfamide, mechlorethamine (mustargen), and melphalan), a nitrosourea (e.g., carmustine, lomustine, semustine, and strptozocin), a triazine (e.g., dacarbazine) an anti-metabolite (e.g., 5-fluorouracil (5-FU), cytarabine (Ara-C), fludarabine, gemcitabine, and methotrexate), a purine analog (e.g., 6-mercaptopurine, 6-thioguanine, and pentostatin (2-deoxycoformycin)), a mitotic inhibitor (e.g., docetaxel, etoposide (VP16), teniposide, paclitaxel, taxol, vinblastine, vincristine, and vinorelbine), an anti-tumor antibiotic (e.g., bleomycin, dactinomycin, daunorubicin, doxorubicin, mitomycin, plicamycin, and idarubicin), a platinum chemotherapeutic agent (e.g., cisplatin and carboplatin), an anthracenedione (e.g., mitoxantrone), a toxin (e.g., ricin A-chain (Burbage, *Leukemia research,* 21.7 (1997): 681-690), diphtheria toxin A (Massuda et al., *Proceedings of the National Academy of Sciences,* 94.26 (1997): 14701-14706; Lidor, *American journal of obstetrics and gynecology,* 177.3 (1997): 579-585), pertussis toxin A subunit, E. colienterotoxin toxin A subunit, cholera toxin A subunit and *Pseudomonas* toxin c-terminal), and a gene therapy vector (e.g., a signal transducing protein (e.g., Src, Abl, and Ras), Jun, Fos, and Myc).

In some embodiments, the therapeutic agent is an immunotherapeutic agent. An immunotherapeutic agent generally triggers immune effector cells and molecules to target and destroy cells (e.g., cancer cells). The immune effector may be, for example, an antibody specific for a marker on the surface of a cell (e.g. a tumor cell). The antibody alone may serve as an effector of therapy or it may recruit other cells to effect cell killing. Various effector cells include, but are not limited to, cytotoxic T cells and NK cells.

Example immunotherapeutic agents include, but are not limited to, azathioprine, chlorambucil, cyclophosphamide, cyclosporine, daclizumab, infliximab, methotrexate, tacrolimus, immune stimulators (e.g., IL-2, IL4, IL-12, GM-CSF, tumor necrosis factor; interferons alpha, beta, and gamma; F42K and other cytokine analogs; a chemokine such as MIP-1, MIP-10, MCP-1, RANTES, IL-8; or a growth factor such FLT3 ligand), an antigenic peptide, polypeptide or protein, or an autologous or allogenic tumor cell composition (see e.g., Ravindranath & Morton, *International reviews of immunology,* 7.4 (1991): 303-329), hormonal therapy, adrenocorticosteroids, progestins (e.g., hydroxyprogesterone caproate, medroxyprogesterone acetate, and megestrol acetate), estrogens (e.g., diethylstitbestrol and ethinyl estradiol), anti-estrogens (e.g., testosterone propionate and fluoxymesterone), anti-androgens (e.g., flutamide), and gonadotropin-releasing hormone analogs (e.g., leuprolide).

Additional immunotherapeutic agents are known in the art, and can be found, for example, in Rosenberg et al, *New England Journal of Medicine,* 319.25 (1988): 1676-1680; and Rosenberg et al, *Annals of surgery,* 210.4 (1989): 474).

The therapeutic agents provided herein can be effective over a wide dosage range and are generally administered in an effective amount. It will be understood, however, that the amount of the therapeutic agent actually administered will usually be determined by a physician, according to the relevant circumstances, including the condition to be imaged, the chosen route of administration, the actual compound administered, the age, weight, and response of the individual subject, the severity of the subject's symptoms, and the like.

Pharmaceutical Compositions

When employed as pharmaceuticals, the compounds and therapeutic agents provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds provided herein (e.g., compounds of Formula I) are suitable for parenteral administration. In some embodiments, the compounds provided herein (e.g., the compounds of Formula I) are suitable for intravenous administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the compositions provided herein are suitable for intravenous administration.

Also provided are pharmaceutical compositions which contain, as the active ingredient, a compound provided herein, or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

Kits

The present application further provides a kit comprising a compound of Formula I, or a pharmaceutically acceptable salt thereof. In some embodiments, the kit further comprises one or more additional therapeutic agents provided herein.

In some embodiments, the kit comprises one or more components of the compounds provided herein (e.g., one or more imaging agents, one or more chelating agents, one or more linking groups, and one or more peptides or small organic molecules that bind granzyme B). In some embodiments, each component of the kit (is stored within the kit in a separate container (e.g., a separate vials). In some embodiments, the components of the kits may be packaged either in aqueous media or in lyophilized form.

In some embodiments, the kit further comprises instructions, for example, as inserts or as labels, indicating quantities of the composition to be administered, guidelines for administration, and/or guidelines for mixing components of the kit to prepare a compound of Formula I, or a pharmaceutically acceptable salt thereof. In some embodiments, the instructions further comprise instructions for performing one or more of the methods provided herein.

The kits provided herein can further include, if desired, one or more conventional pharmaceutical kit components, such as, for example, containers with one or more pharmaceutically acceptable carriers, additional containers, etc., as will be readily apparent to those skilled in the art.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Cell Lines and Reagents

CT-26 cells were acquired from ATCC (Manassas, VA) and cultured in Roswell Park Memorial Institute (RPMI) medium. BRAF V600E mutant melanoma cells were developed from previously described Tyr-CreER;BrafCA;Ptenlox/lox mouse (see e.g., Dankort et al, *Nature Genetics,* 41.5, (2009):544-552) and were kindly provided by Dr. David Fisher, and cultured in DMEM with 10% FBS. Anti-mouse PD1 (clone RMP1-14) and anti-mouse CTLA4 (clone 9D9) were obtained from Bio X Cell (West Lebanon, NH). Dabrafenib was purchased from LC Laboratories (Woburn, MA). For Western blot analyses, anti-CD8 (Ab108292, Abcam, Cambridge, MA), anti-CD3 (sc-20047, Santa Cruz Biotechnology, Dallas, TX ant-CD4 (sc-19643, Santa Cruz), anti-FoxP3 (12653s, Cell Signaling Technologies, Danvers, MA), anti-βSTAT (700349, ThermoFisher, Waltham, MA), anti-Granzyme B (4275s, Cell Signaling Technologies) and beta-actin (Cell Signaling Technologies 4970S)1:1000 were purchased.

Granzyme B was purchased from R&D systems (Minneapolis, MN) and activated using Cathepsin B (R&D systems) following manufacturer protocol. Enzyme activity was assessed by cleavage of BOC-Ala-Ala-Asp-SBZL (SBZL—thiobenzyl ester)(Sigma) and reaction with 5,5'-

Dithio-Bis (2-Nitrobenzoic Acid)(Sigma) with absorbance measurements at 405 nm (NanoDrop 2000 Spectrophotometer, Thermo Scientific). Serial dilutions of nonradioactive gallium-labeled NOTA-GZP were used to inhibit granzyme B by incubation at 37° C. for 30 minutes prior to addition of substrate. Additionally, $^{68}$Ga-NOTA-GZP (Example 1) was incubated with the activated forms of granzyme B, granzyme A (R&D Systems), granzyme H (R&D Systems), granzyme K (Enzo Life Sciences), and pro-granzyme B to assess the specificity of the peptide. After a 30-minute incubation at 37° C., enzymes were purified by size exclusion chromatography and bound radioactivity assessed by gamma counter (Wizard 2480, Perkin Elmer)

Mouse Treatment Protocols

Mice were housed and maintained by the Center for Comparative Medicine at Massachusetts General Hospital following animal protocols approved by the Massachusetts General Hospital Institutional Animal Care and Use Committee. 1×10' CT-26 cells were diluted 1:1 with Matrigel and injected in the right shoulder of female BALB/C mice.

For imaging studies, mice were treated with intraperitoneal injection of either vehicle, 200 μg anti-PD-1 murine therapeutic antibody (αPD1), or both 200 μg αPD1 and 100 μg anti-CTLA-4 murine therapeutic antibody (CTLA-4) on days 3, 6, and 9 following CT-26 tumor inoculation. 1×10$^6$ BP cells were diluted 1:1 with Matrigel and injected in the right shoulder of female C57BL/6 mice. Once tumors had reached 3-5 mm in diameter, mice were treated with daily oral gavage of vehicle or dabrafenib prepared in aqueous suspension with 0.5% hydroxypropylmethyl cellulose (HPMC) and 0.2% Tween. One day following initiation of BRAF inhibition, mice were additionally randomized to intraperitoneal injection with 200 μg αPD1 as specified. Mice were sacrificed on specified day either for Western blot and immunohistochemistry alone, or following imaging for correlative analysis.

For imaging studies with correlative growth curve analysis, BALB/C mice injected with CT-26 as above were treated with either 200 μg αPD1 and 100 μg αCTLA-4 or αPD1 alone every three days following inoculation until day 30. Mice were imaged on day 14 and tumor sizes were measured three times weekly.

For the imaging studies described in Examples 9-12, anti-mouse PD-1 (clone RPM1-14), anti-mouse CTLA-4 (clone 9H10), and anti-mouse TIM-3 (clone RPM3-23) therapies were obtained from Bio X Cell (West Lebanon. NH).

Biochemical Analysis of Tumors

For the studies described in Examples 9-12, tumors were excised from sacrificed mice for ex vivo analysis on day 12 post-tumor inoculation and lysed in 1% SDS solution prior analysis by Western blotting. Anti-Granzyme B (4275S, Cell Signaling Technologies, Danvers, MA), anti-CTLA-4 (ab134090, Abcam, Cambridge, MA), anti-PD-1 (12A7D7, ThermoFisher, Waltham, MA), anti-TIM-3 (ab185703, Abcam Cambridge, MA), and anti-β-actin (4970S, Cell Signaling Technologies, Danvers, MA) antibodies were used and subsequently detected by horseradish peroxidase-conjugated goat anti-rabbit polyclonal antibody (ab6721, Abcam, Cambridge, MA) as per manufacturers' recommendations. Bands were detected using SignalFire™ ECL Reagent (Cell Signaling Technologies, Danvers, MA) and imaged on Kodak In-Vivo Multispectral Imaging System using CarestreamMI software (Carestresam Health Inc., Woodbridge CT) with 1-minute exposure. Images were quantitatively analyzed by ratio of net relative optical intensity of the target of interest to that of β-actin for each sample.

PET Imaging

Mice were imaged on a GE Triumph PET/CT. Following CT acquisition, PET images were obtained for 15 min in 2 bed positions. Images were constructed using 3D-OSEM (4 iterations, 16 subsets) and corrected for scatter and randoms. The mean standard uptake value (SUVmean) for each tumor was calculated in a 3D region of interest auto-drawn around the tumor using a 30% is contour threshold. Region of interests were also calculated for left ventricle, liver lung, muscle, and kidney. Images were post-processed using VivoQuant (InviCRO, Boston, MA).

For the imaging studies described in Examples 9-12, mice were intravenously injected with $^{68}$Ga-NOTA-GP on day 12 post-inoculation and subsequently imaged after one hour. Imaging was performed using a rodent Triumph PET/CT (GE Healthcare, Wilmington, MA). PET images were acquired for 15 min and followed by CT acquisition. Reconstruction was achieved using 3D-MLEM (4 iterations, 20 subsets) and corrected for scatter and randoms. VivoQuant software (InviCRO, Boston, MA) was used for image processing and analysis. Individual tumors were identified manually by drawing a 3D region of interest using CT-anatomic correlation. Background blood pool radioactivity was measured by identifying the left ventricle of the heart as a region of interest. Specific Ga NOTA-GP uptake was quantified by dividing total tumor uptake by background blood pool to derive a tumor to blood ratio (TBR).

Bio-Distribution Studies

Following injection with ~1 mCi of $^{68}$Ga-NOTA-GP (see Example 1) via tail-vein mice were sacrificed at either one-hour or two-hour time-points. Mouse urine, blood, tumor, and vital organs were sampled, and radioactivity assessed on a gamma-counter.

Statistical Analysis

Statistical analysis was performed using the Graphpad Prism Version 4 software. PA non-linear regression was used for competitive binding analysis. Pearson's correlation test was performed to correlate total tumoral granzyme B expression determined by Western blot to tumoral to blood ratio (TBR). TBR for treated and untreated tumor compared by paired t test.

Statistical analysis and graphing described in Examples 9-12 was performed using GraphPad Prism Version 6 software (GraphPad Software, Inc., La Jolla, CA). Unpaired t tests with Welch's correction were used for all comparisons between immunotherapy-treated and vehicle-treated tumors. A first-order regression weighted by group size was used to correlate percent response with average tumor to blood ratio TBR for each treatment arm. Statistical inference based on Pearson's correlation coefficient was used to define 95% confidence bands of the best-fit line.

Example 1. Synthesis of Granzyme B Imaging Agent ($^{68}$Ga-NOTA-GP)

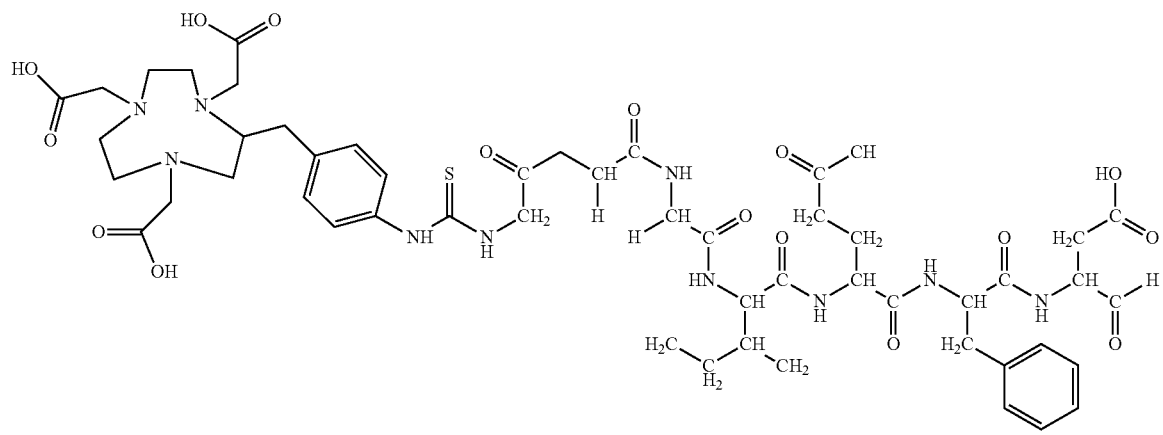 [SMILES: CCC(C)C(NC(=O)CNC(=O)CCC(=O)CNC(=S)Nc1ccc(CC2CN(CC(=O)O)CCN(CC(=O)O)CCN2CC(=O)O)cc1)C(=O)NC(CCC(C)=O)C(=O)NC(Cc1ccccc1)C(=O)NC(C=O)CC(=O)O]

NOTA-β-Ala-Gly-Gly-Ile-Glu-Phe-Asp-CHO (i.e., NOTA-GP; NOTA-GZP) was synthesized using standard FMOC chemistry. Chemical purity was analyzed with HPLC and mass spectroscopy. Calculated m/z: 1176.949. Furthermore HPLC analysis of the peptide illustrated a greater than 90% purity, which was sufficient for all experiments.

$^{68}$Ga was obtained from a $^{68}$Ge/$^{68}$Ga generator (iThemba Labs, South Africa) eluted with 0.6N HCl. The eluant was added to a buffer system of 2M HEPES at pH 3.5-4.0 with ~100 μg of NOTA-GP. The labeling reaction proceeded at room temperature for 10 minutes. The reaction product was loaded on a reverse-phase C18 Sep-Pak mini cartridge and eluted with 200 μL of 70% ethanol. The final formulation was adjusted to 10% ethanol in saline. The chemical and radiochemical purity of $^{68}$Ga-NOTA-GP (i.e., $^{68}$Ga-NOTA-GZP) was measured through radio thin-layer chromatography (TLC). The radiolabeling occurred a yield of 67±11%, radiochemical purity of >95%, and an average specific activity of 5190±1100 MBq/mg.

Example 1A. Synthesis of Biotinylated Human Granzyme B Peptide

Biotin-β-Ala-Gly-Gly-Gly-Ile-Glu-Pro-Asp-CHO (hGZP; SEQ ID NO: 25) was synthesized according to the procedures described above in Example 1. Calculated m/z=907.010.

Example 2. Differential Expression of Granzyme B in Response to Immune Therapy

To quantify the difference in granzyme B expression over the course of immunotherapy treatment, CT26 colon cancer bearing mice (BALB/C) were treated with 200 ng anti-PD-1 and 100 ng anti-CTLA-4 antibodies on days 3, 6 and 9 following tumor inoculation. On day 10, a subset of mice (4 treated and 4 untreated) were sacrificed and their tumors were excised and prepared for SDS-PAGE. Western blot analysis of the tumors was performed. Expression of granzyme B was quantified and standardized to beta-actin expression as a loading control. The results demonstrated that granzyme B was expressed at a low level in both treated and untreated mice and that there was no statistical difference between the two groups. On day 14 post-inoculation mice were sacrificed and analyzed by Western blot in the same manner as those on day 10. The treated mice on day 14 had over 100 times higher expression of granzyme B. and there was a significant (4×) difference between treated and untreated mice, as shown in FIG. 1.

Figure 2A:
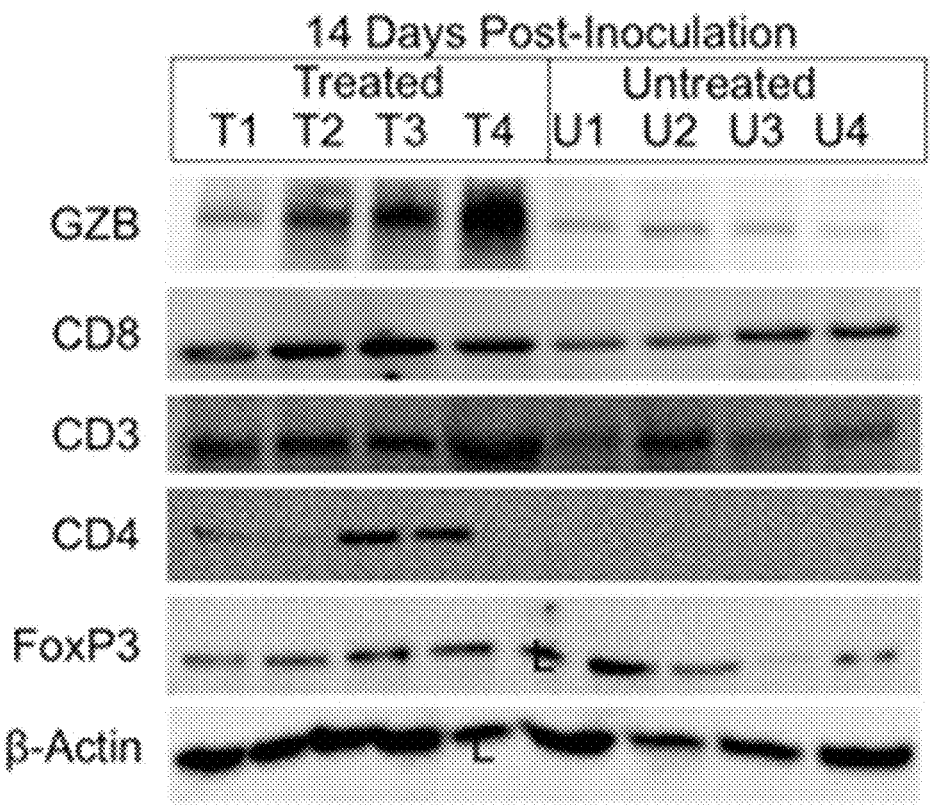
FIG. 2A shows a Western blot analysis of treated vs. untreated tumors and demonstrates increased markers associated with a cytotoxic T-cell response, with increase in granzyme B expression the most pronounced.
Figure 2B:
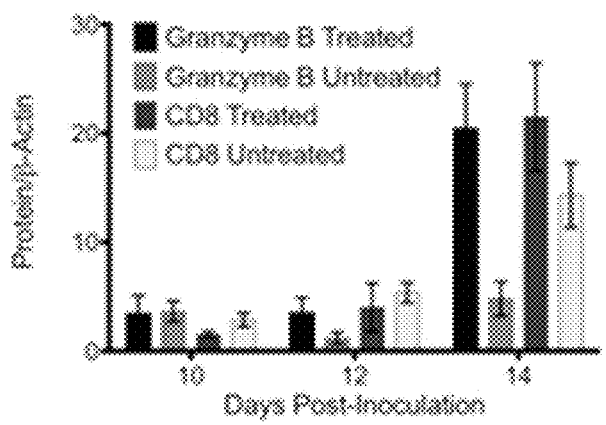
FIG. 2B shows an analysis of granzyme B and CD8 expression normalized to beta-actin, which demonstrates a significant difference between granzyme B in treated and untreated tumors (20.4±4.1 vs. 4.7±1.6), whereas no significant difference was observed in CD8 (21.5±5.0 vs. 14.3±3.0).
Figure 3A:
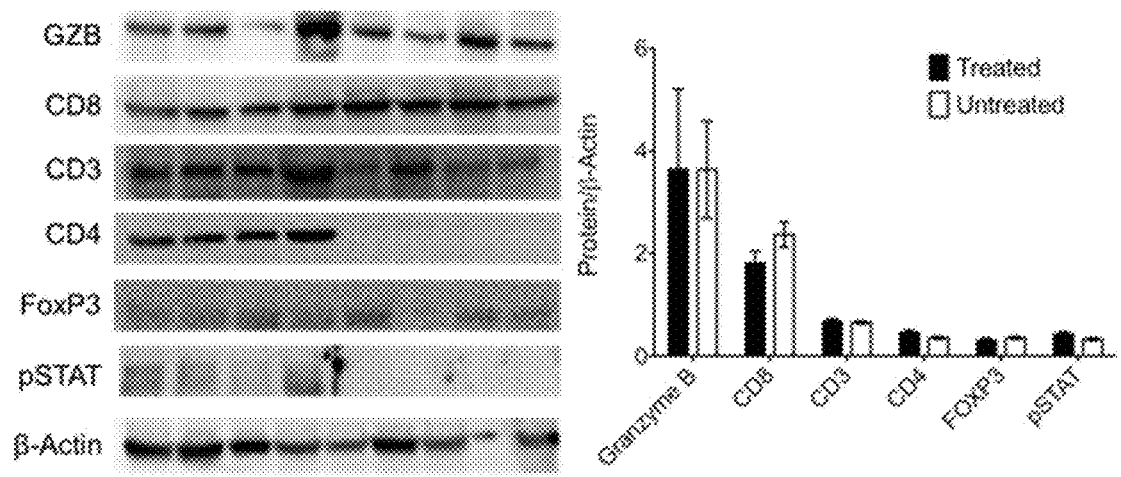
FIG. 3A shows a Western blot analysis of dual treated (left four tumors) and control (right four) tumors excised on day 10 after inoculation.
Figure 3B:
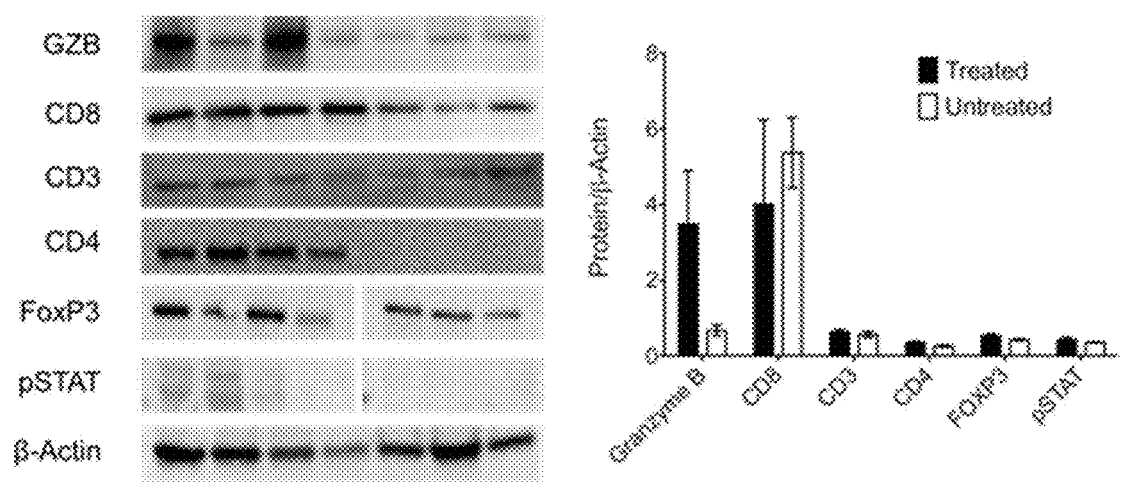
FIG. 3B shows a Western blot analysis of dual treated (left four tumors) and control (right four) tumors excised on day 12 after inoculation.

Initial analysis of day 14 tumor immune cell infiltration and activation was performed by Western blotting in CT26 tumors treated with a dual-agent immunotherapy regimen (αPD1, αCTLA4) or vehicle only as a control. Neither CD8 nor CD3 expression levels differed significantly between treated and untreated mice, as shown in FIG. 2A. CD4 expression was present at low levels in treated mice and undetectable in untreated mice. Further exploration into mechanistic markers including granzyme B revealed a divergence between treated and untreated mice in granzyme B (i.e., GZB) expression. Quantification of the western blot data standardized to β-actin expression revealed a significantly higher level of GZB in treated tumors (GZB:β-actin=20.4±4.1) in comparison to untreated tumors (4.7±1.6), as shown in FIG. 2B. By comparison CD8:β-actin was 21.5±5.0 in treated mice and 14.3±3.0 in untreated mice. Both GZB and CD8 expression levels increased in comparison to days 10 and days 12. A dynamic range of GZB expression was seen across treated tumors, with 1 of 4 treated tumors demonstrating a low GZB expression at levels similar to untreated mice. Without being bound by theory, the heterogeneity of GZB expression suggests that levels of the secreted protease may serve as a biomarker for immune response. To further examine the temporal expression of GZB, treated and untreated mice were sacrificed at days 10 and 12 post-inoculation and subjected to Western blotting in the manner described above, and are shown in FIGS. 3A-3B.

Example 3. Binding of $^{68}$Ga-NOTA-GP to Purified Granzyme B

Figure 4:
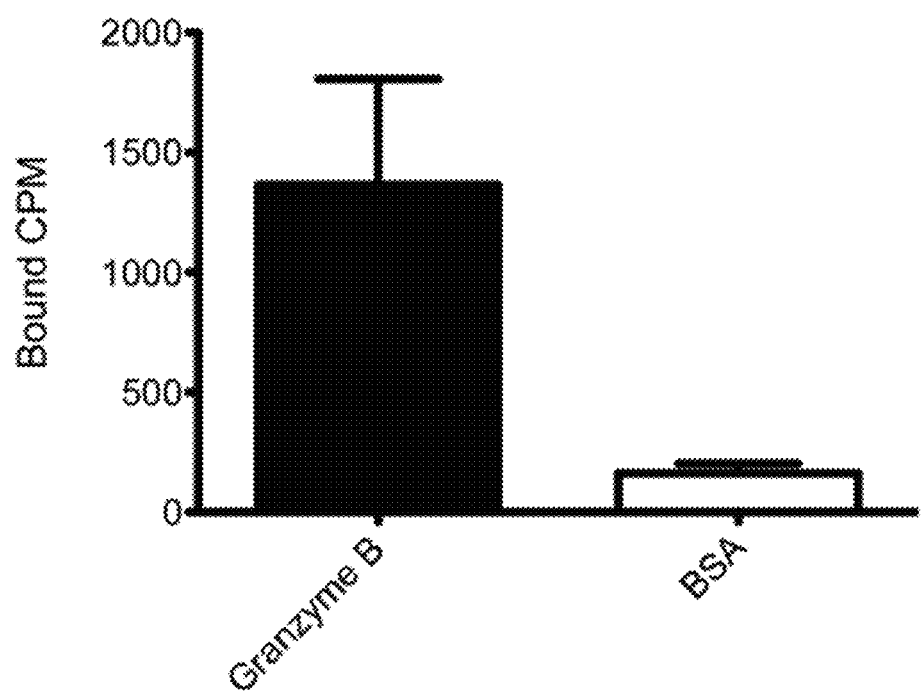
FIG. 4 shows data representative of the binding of $^{68}$Ga-NOTA-GP to purified granzyme B compared to $^{68}$Ga-NOTA-GP binding to BSA. The bars represent the mean of 6 replicates ±SD.
Figure 5:
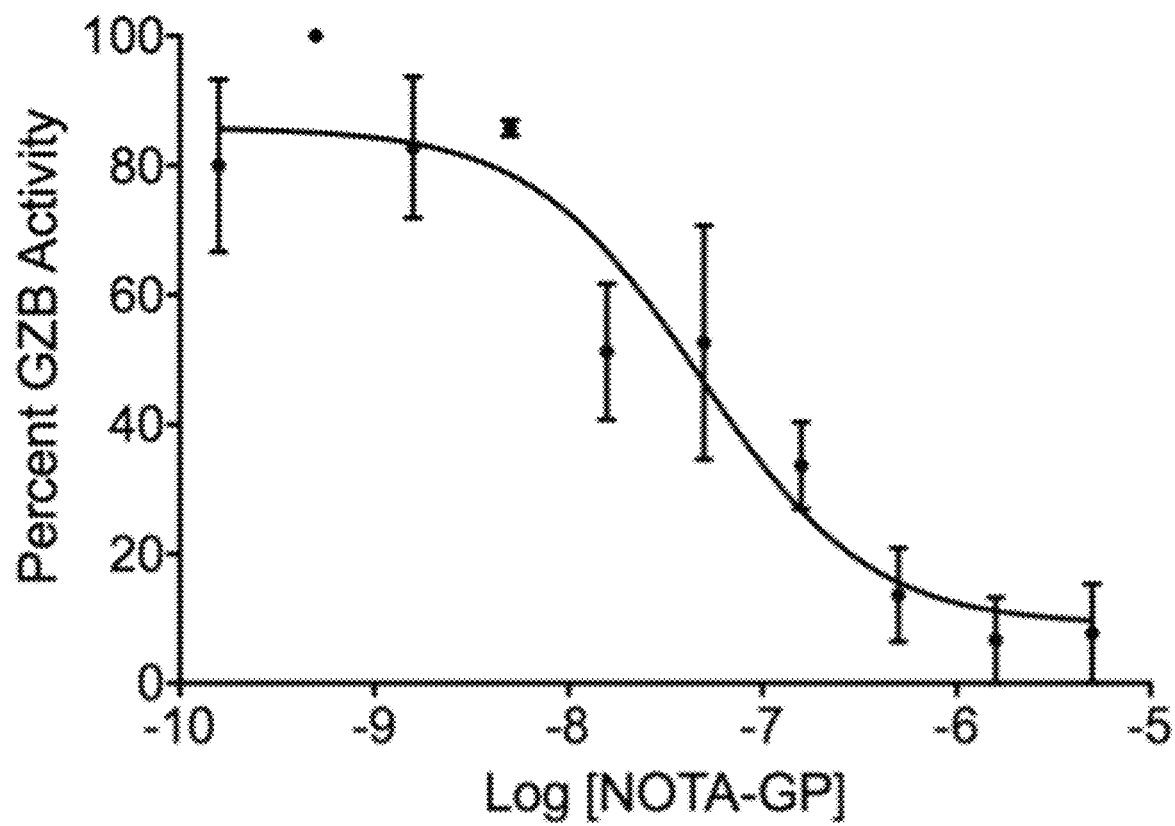
FIG. 5 shows data representative of the inhibition of granzyme B with $^{68}$Ga-NOTA-GP.

Granzyme B was adsorbed to plates and the plates were blocked with non-fat milk. The $^{68}$Ga-NOTA-GP was permitted to bind for 1 h, the wells washed, and bound $^{68}$Ga-NOTA-GP recovered by incubation with 2N NaOH and counted by gamma counter. The peptide exhibited significantly (P<0.05) higher binding to granzyme B than to the control protein (BSA), as shown in FIG. 4. The bars in FIG. 4 represent the mean of 6 replicates±SD. In vitro activity studies show that NOTA-GP inhibits granzyme B activity with a Ki of 47±54 nM, as shown in FIG. 5.

Example 4. Binding of $^{68}$Ga-NOTA-GP to Cells

Figure 6:
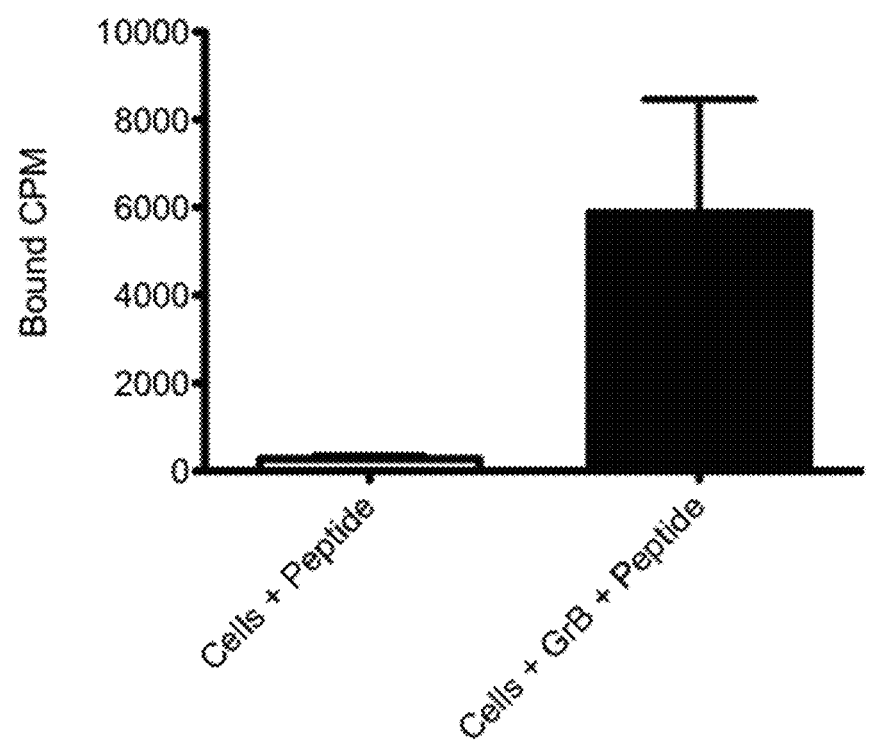
FIG. 6 shows data representative of $^{68}$Ga-NOTA-GP binding to granzyme B in CT26 cells compared to CT26 cells that were not inoculated with granzyme B (I.e., GZB).

CT26 cells were plated in 96 well plates and grown to 70% confluency. $^{68}$Ga-NOTA-GP was diluted to 100 µCi/mL in 1% BSA plus RPMI buffer and either pre-incubated with granzyme B (60 nM) or vehicle prior to addition to wells. The peptide was incubated with cells for 30 min prior to washing and elution with 2M NaOH. Wells were counted in a gamma counter and the mean of 6 wells was plotted ±SD, as shown in FIG. 6, which demonstrates that $^{68}$Ga-NOTA-GP binds granzyme B and is taken up specifically by cancer cells.

Example 5. Ex Vivo Tumor Specificity

Figure 7A:
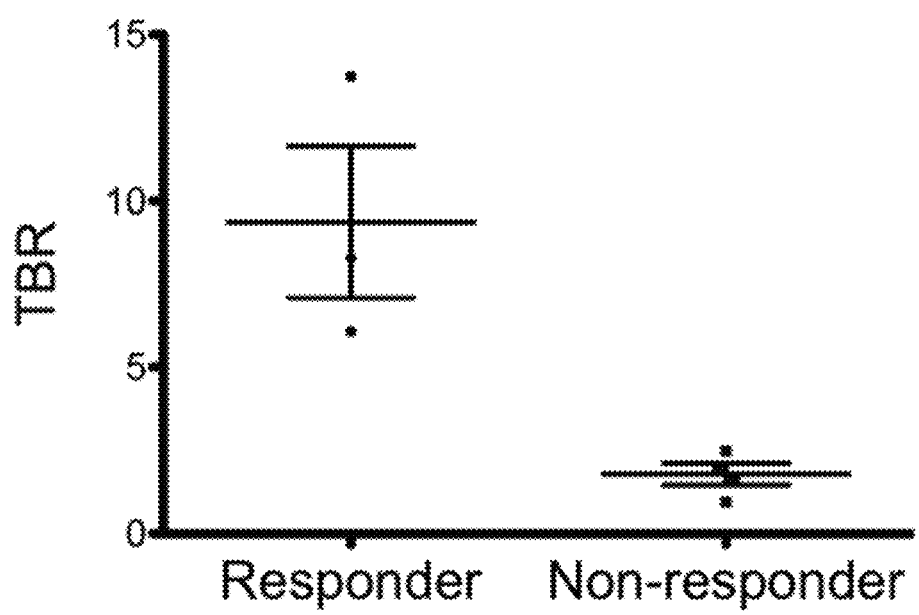
FIG. 7A shows the tumor to blood ratio of mice treated with combination therapy (anti-PD-1 and CTLA-4) and untreated mice.

After confirming the $^{68}$Ga-NOTA-GP bound to purified granzyme B and specifically accumulated in target cells, the in vivo tumor accumulation was investigated in CT26 tumor bearing mice using the same model used to generate the Western blot data from Example 2 (see FIG. 1). On day 14 post-inoculation, mice were injected with 370 MBq of 0Ga-NOTA-GP and mice were sacrificed at 1 h following injection. Tumors and blood were collected from 7 mice that were treated with combination therapy (ant-PD-1 and CTLA-4). The tumors were grouped based on size as either responders (mass <0.8 mg) or non-responders (mass ≥0.8 mg) The amount of radioactive $^{68}$Ga-NOTA-GP in both the tumor and blood were quantified using a gamma counter and the adjusted based on mass and the ratio of injected dose per gram of tumor to blood (TBR) was plotted for tumors in each group. Each mouse that was a responder had a higher uptake (range 6.06-13.74) than the non-responders (range −0.95-2.48), as shown in FIG. 7 which indicated that $^{68}$Ga-NOTA-GP was specific for tumors which were responding to immune therapy.

Figure 7B:
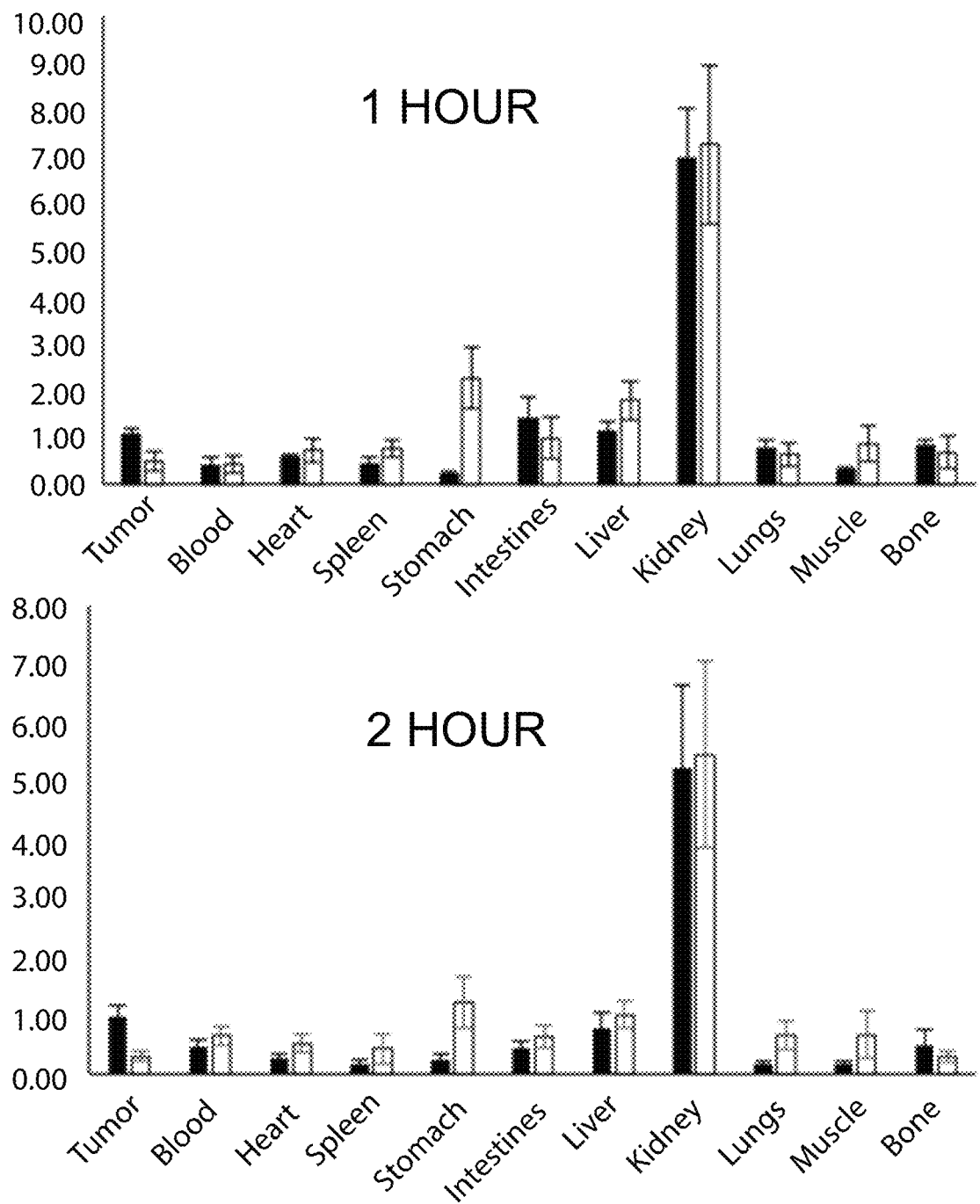
FIG. 7B shows 1 hour and 2 hour ex-vivo biodistribution studies confirm findings of PET imaging. Kidney uptake is consistent with renal excretion.

Following imaging, mice were sacrificed and tumoral GZB expression quantified by Western blot. TBR to GZB expression comparison revealed a significant correlation between uptake and GZB expression (P<0.001), indicating that tumoral uptake of $^{68}$Ga-NOTA-GP was dependent on GZB expression. Additional ex-vivo bio-distribution studies at 1 h and 2 h post-injection confirmed differential tumor uptake and rapid renal clearance. Tumoral uptake of treated tumors was measured at 1.15% ID/g at 1 h and 1.02% ID/g at 2 h in comparison to 0.70 and 0.55% ID/g in untreated control tumors, as shown in FIG. 7B.

Example 6. In Vivo PET Imaging of Granzyme B Expression

Figure 8:
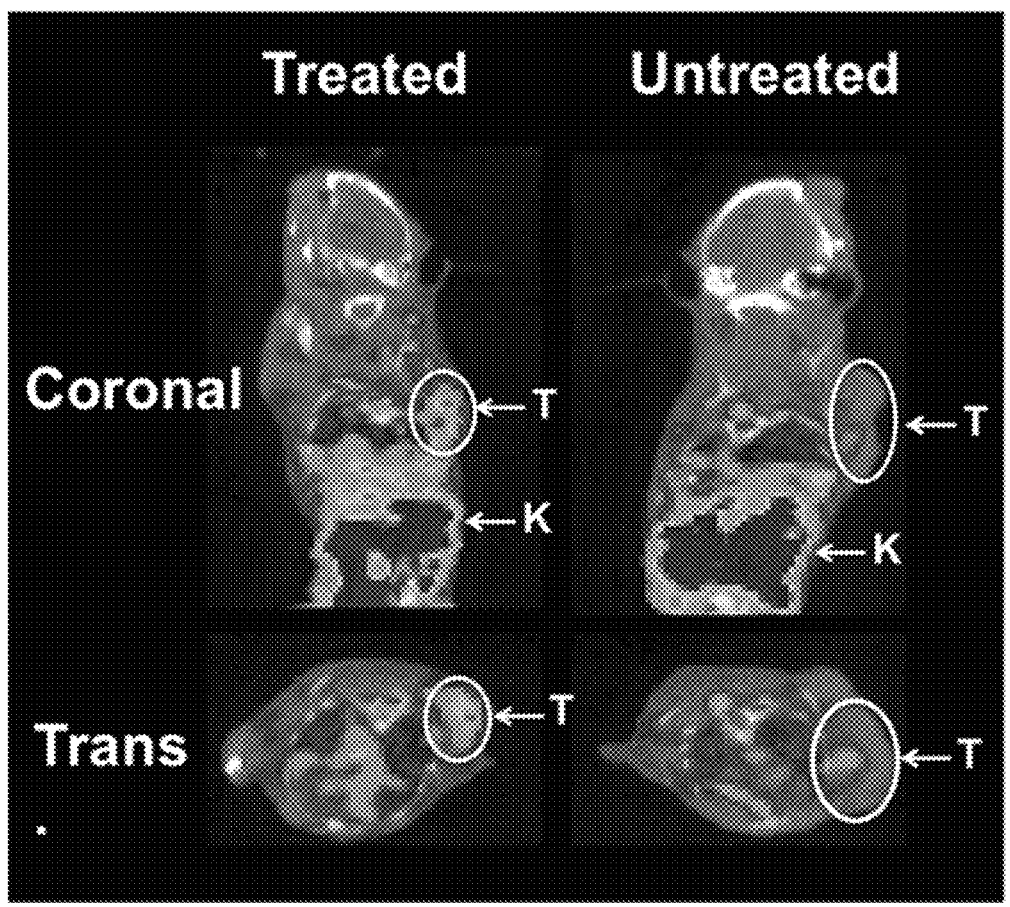
FIGS. 8-10 shows in vivo PET images of granzyme B expression in mice using $^{68}$Ga-NOTA-GP.

To assess the ability of $^{68}$Ga-NOTA-GP to detect granzyme B expression in a non-invasive imaging technique, the $^{68}$Ga-NOTA-GP was injected in the same manner as Example 5. At 1 h post-injection, the mouse was subjected to PET imaging. PET imaging was performed for 30 minutes followed by 2 minute CT acquisition. Images were reconstructed using 3D-OSEM (4 iterations, 16 subsets) and corrected for randoms and scatter, and are shown in FIG. 8. The images showed distinct differences between tumor uptake (T) in treated and untreated mice. Kidney uptake in both groups of mice was also observed, which was consistent with peptide clearance. This imaging analysis demonstrated the value of $^{68}$Ga-NOTA-GP for detecting expression in vivo using PET imaging.

Figure 9:
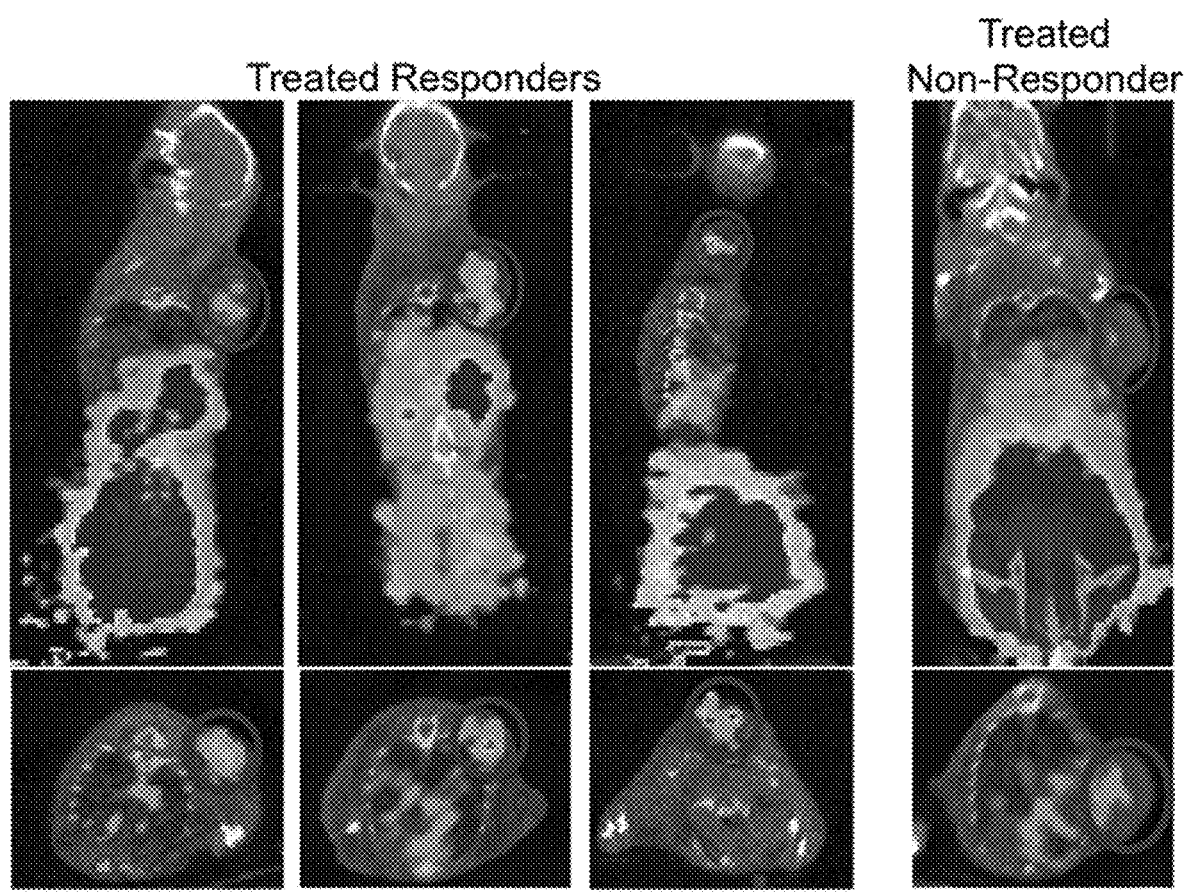
Figure 10:
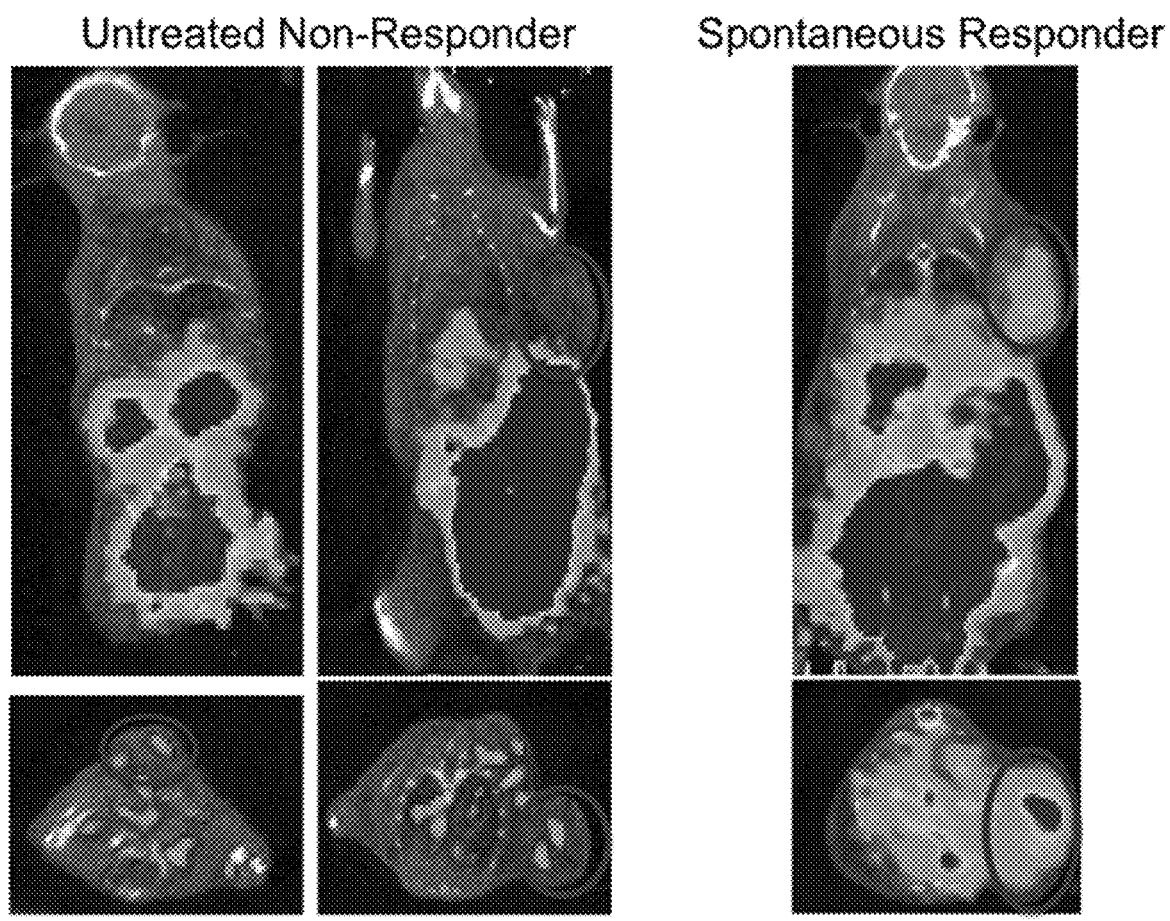

Example 7. In Vivo PET Imaging of Granzyme B Response to Immune Therapy in Tumor Bearing Mice To further evaluate the predictive nature of granzyme B expression in tumor-bearing mice treated with combination checkpoint inhibitor therapy, imaging was performed in the same manner as described previously in four treated and three vehicle only mice. Tumor uptake was clearly differentiated in both groups of mice. In the treated mice, high uptake was observed in 3 out of 4 mice, which were presumed to be responsive to checkpoint therapy, whereas one mouse had low uptake, which would predict unresponsiveness to therapy, as shown in FIG. 9. Untreated mice, showing 2 mice with low uptake of the tracer, which was expected given the lack of therapy, as shown in FIG. 10. One untreated mouse demonstrated high levels of probe uptake, which could be representative of a spontaneous immune response unrelated to therapy.

Figure 11:
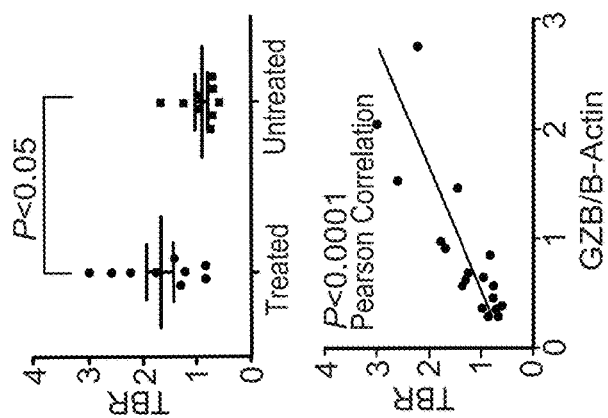
FIG. 11 shows PET images using $^{68}$Ga-NOTA-GP. The images show that PET imaging distinguishes between dual-treated and control CT-26 tumors. Analysis of tumor to left ventricle ratio (TBR) of treated vs. control tumors shows TBR of 1.69±0.26 for treated, whereas the mean TBR of untreated tumors was 0.93±0.11, an increase of 83% (P<0.05).

On day 14 post-inoculation, mice were injected with ~37 MBq of purified $^{68}$Ga-NOTA-GP intravenously and imaged at 1 h post-injection. PET imaging revealed uptake in treated tumors, kidneys and bladder, the latter of the two consistent with renal clearance characteristic of small peptides. $^{68}$Ga-NOTA-GP PET imaging uptake was standardized by dividing tumor uptake by left ventricle uptake to derive a tumor to blood ratio (TBR). The mean TBR of treated mice was calculated at 1.69±0.26, whereas the mean TBR of untreated mice was 0.93±0.11, a significant increase (83%, P<0.05) from untreated to treated mice, as shown in FIG. 11. $^{68}$Ga-NOTA-GP uptake was observed across both treated and untreated tumors. The correlation with GZB expression as assesed by ex-vivo western blot demonstrates that this correlation is due to variability in GZB expression across tumors as opposed to variable probe distribution.

Example 8. Immunofluorescent Staining to Assess Granzyme B Expression in Tumors Following Immunotherapy Prior to CTL activation, GZB is contained within cytotoxic granules, and following activation is released at an immune synapse between the CTL and its target cell. However, location (e.g., intracellular vs. extracellular) in the context of cancer immunotherapy as well as the fate of GZB after release is not well understood. To gain a better understanding of GZB location within the tumor microenvironment, tumors were analyzed by immunohistochemistry and immunofluorescence.

Figure 12:
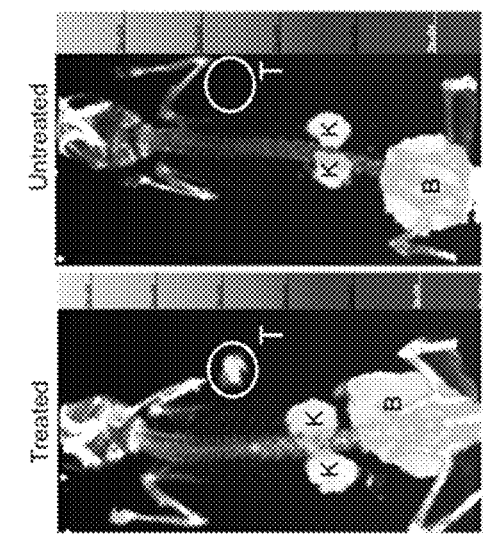
FIG. 12 shows immunofluorescent analysis of granzyme B location relative to CD3+ T cells and nuclei. The immunofluorescent images show increased granzyme B in treated tumors that does not co-localize with CD3.
Figure 12:
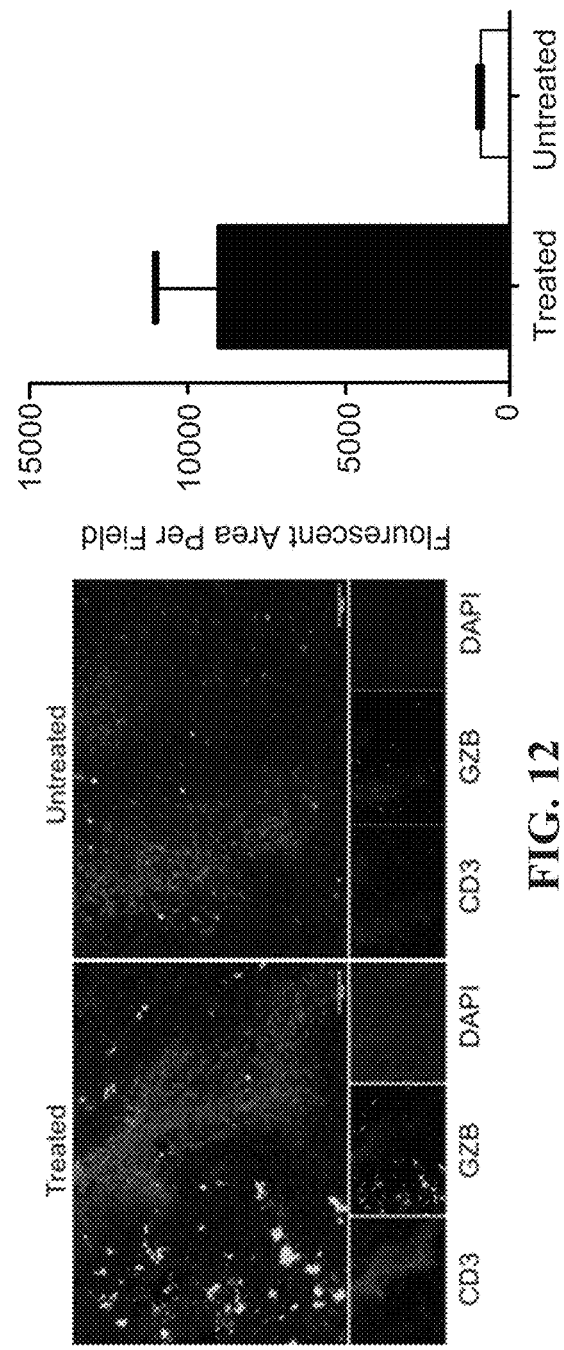
Figure 13:
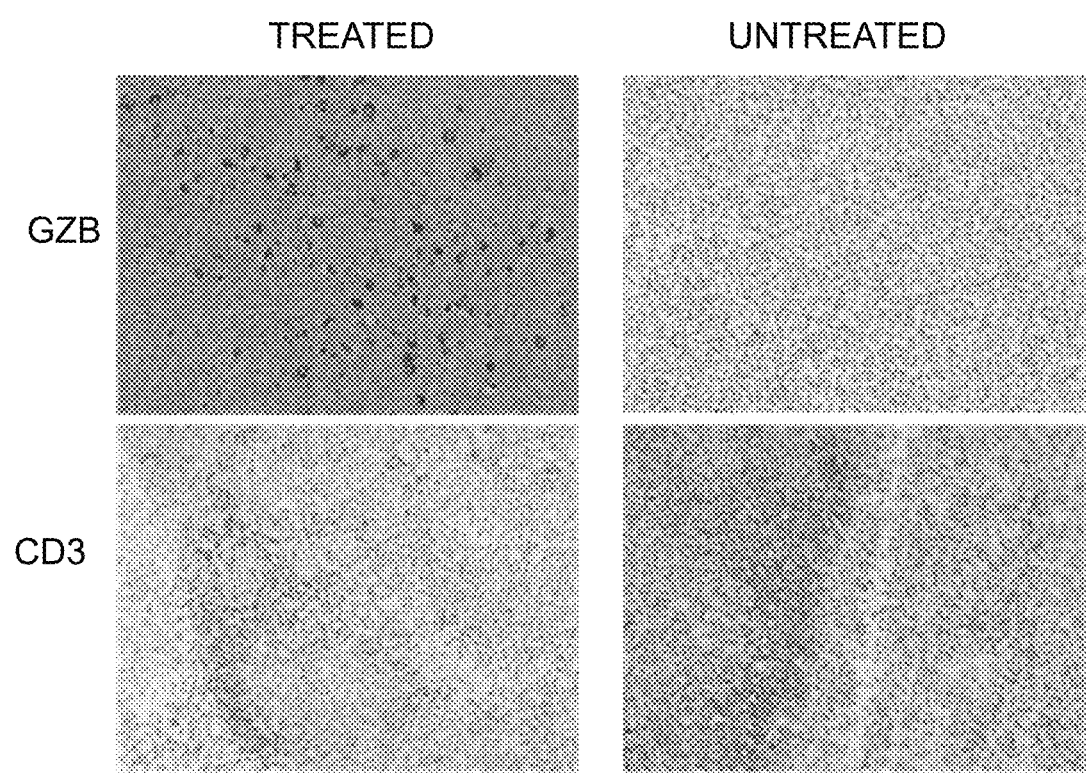
FIG. 13 shows representative results of an immunohistochemistry assay of granzyme B and CD3 in immunotherapy treated mice and untreated mice. Illustrating that immune cell infiltrate in both treated and untreated tumors, but only treated tumors actively express granzyme B.

Treated and untreated tumor slices were stained for GZB, in addition to CD3, to assess whether the GZB was sequestered within T cells or secreted. CD3 staining showed a low level of T-cell infiltrate within untreated tumors that was increased within treated tumors. Granzyme B staining showed further differences between untreated and treated tumors and showed two distinct patterns of GZB location. The first observed pattern was one of low intensity and small surface area that co-localizes with CD3 staining, as shown in FIG. 12, seen within both treated and untreated tumors, that is believed to represent GZB contained within CTL cytotoxic granules. A second pattern of GZB staining resulted in larger and more intense areas of staining that generally did not co-localize with CD3. Fluorescent threshold analysis of GZB IF samples showed that there was more high-intensity staining in treated vs. untreated tumors (P<0.01). Without being bound by theory, it is proposed that the areas of high-intensity GZB staining correspond to areas of prior exocytosis of GZB and this represents GZB that has either already participated in the killing of tumor cells, or GZB leaked from the immune-synapse that remains within the extracellular space. These results provided further evidence that higher GZB expression in treated tumors was due to active CTLs that were secreting the protease in response to immunotherapy and thus represented a potential biomarker for monitoring tumoral response to immunotherapy. IHC findings confirm findings of immunofluorescence, as shown in FIG. 13.

Example 9. Western Blot Analysis of Checkpoint Inhibitor Targets PD-1, PD-L1, CTLA-4 and TIM-3

CT26 and MC38 were diluted 1:1 (v:v) in Matrigel (Corning, Tewksbury, MA) and injected into the upper right flank of balb/c or C57BL/6 mice, respectively. The mice were treated on days 3, 6, and 9 following tumor inoculation by intraperitoneal injection with saline (i.e., vehicle), 200 µg anti-PD1 (i.e., monotherapy), 200 µg anti-PD1 and 100 µg anti-CTLA4 (i.e., P+C combination therapy), or 200 µg anti-PD1 and 250 µg anti-TIM-3 (I.e., P+T combination therapy). Mice were either imaged or sacrificed for ex vivo Western blot analysis on day 12. For survival imaging experiments, tumors dimensions were measured with calipers every 2-3 days beginning on day 5 for MC38 and day 10 for CT26. Mice were sacrificed once tumors exceeded a volume of 500 mm³ or developed ulceration.

Figures 14A, 14B, 14C:
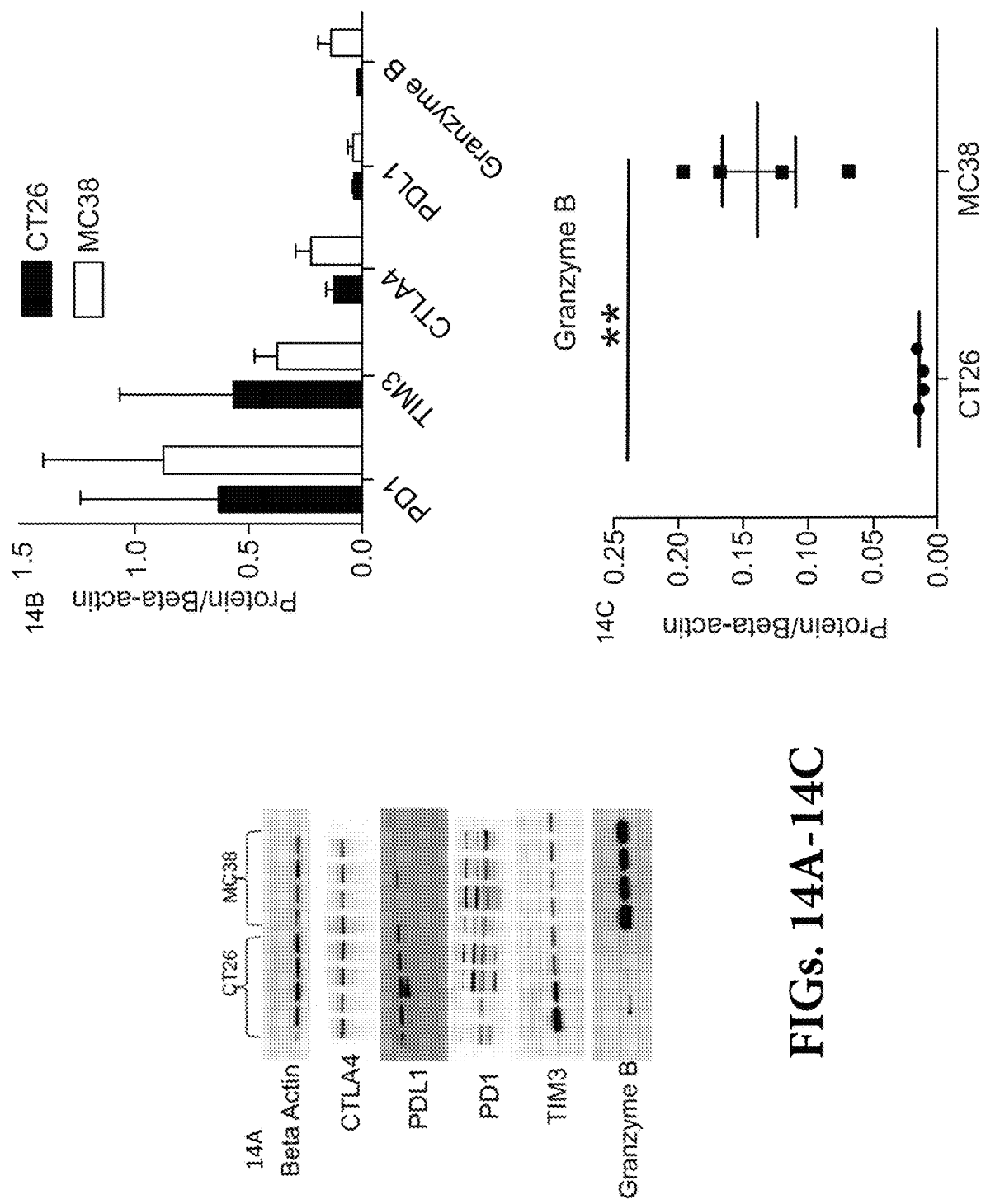
FIGS. 14A-14C show results of an ex vivo immunoblot analysis of CT26 and MC38 tumors as described in Example 9.
Figures 15A, 15B, 15C, 15D:
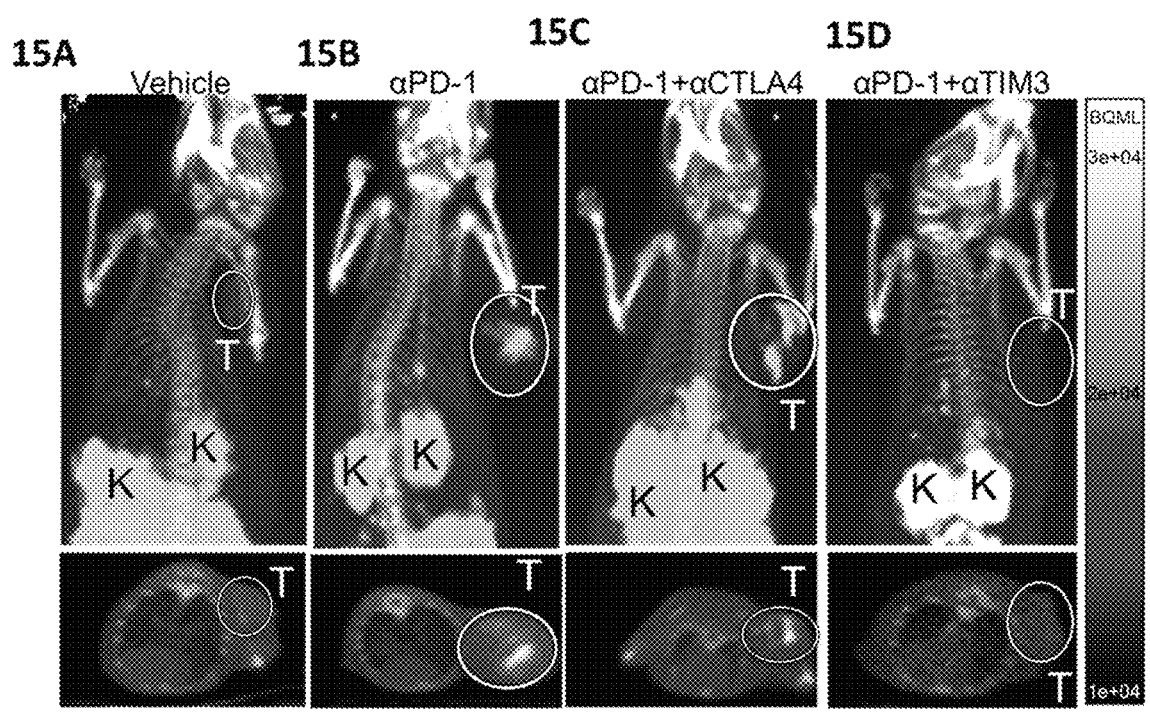
FIGS. 15A-15D show representative PET-CT images of CT26-bearing mice treated with saline (FIG. 15A), monotherapy (FIG. 15B), P+C combination therapy (FIG. 15C), and P+T combination therapy (FIG. 15D). Top images are coronal maximal intensity projections of whole-body intake, and bottom images are representative axial slices of the same data. Tumors are circled and marked with T and kidneys are marked with K.
Figures 16A, 16B, 16C, 16D:
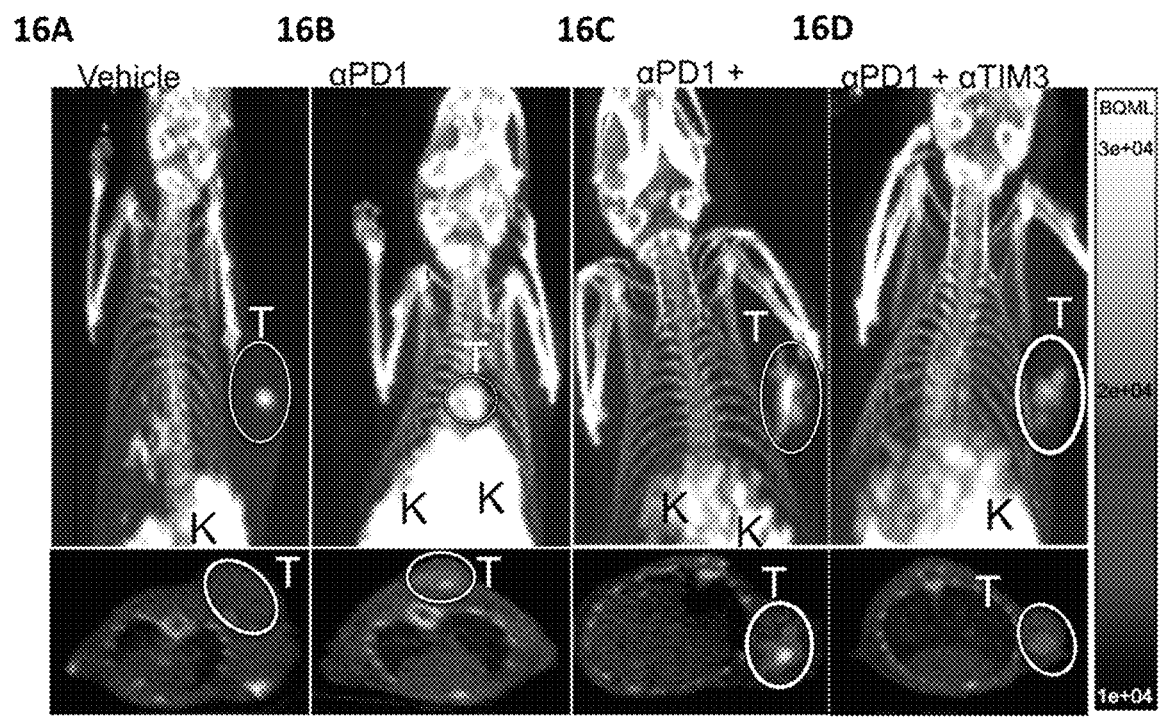
FIGS. 16A-16D shows representative maximal intensity projections and example axial single-slice PET-CT images of MC38-bearing mice treated with saline (FIG. 16A), monotherapy (FIG. 16B), P+C combination therapy (FIG. 16C), and P+T combination therapy (FIG. 16D). Images were taken day 12, 1 hour post-injection with $^{68}$Ga-GP. Tumors are circled and marked with T and kidneys are marked with K.

MC38 and CT26 syngeneic tumors were excised and evaluated by immunoblot on day 12 to determine baseline levels of the checkpoint inhibitor target molecules, PD-1, PD-L1, CTLA-4 and TIM-3, as shown in FIGS. 14A-14C. Levels of CTLA-4 were two-fold higher in MC38 tumors than in CT26 tumors (CTLA-4:1-actin=0.225 versus 0.121, p=0.043). PD-1, PD-L1, and TIM-3 expression levels were not significantly different between each tumor type. To assess the feasibility of imaging granzyme B in MC38 tumors, granzyme B levels were also evaluated, and granzyme B expression was found to be significantly higher in MC38 tumors (granzyme B:β-actin=0.138) than in CT26 tumors (0.013, p=0.014).

Example 10. Granzyme B PET Imaging of CT26 and MC38 Tumor-Bearing Mice

CT26 and MC38 tumor-bearing mice treated with anti-PD1 monotherapy, P+C combination therapy, P+T combination therapy, or saline (see Example 9), were imaged using $^{68}$Ga-NOTA-GP on day 12 to non-invasively assess granzyme B levels. PET imaging showed common non-tumor organ uptake patterns in all mice analyzed, including kidney and bladder accumulation consistent with renal clearance characteristic of small peptides. Degree of tumor uptake, however, varied based on tumor model and therapy regimen as shown in FIGS. 15A-17D.

Figures 17A, 17B, 17C, 17D:
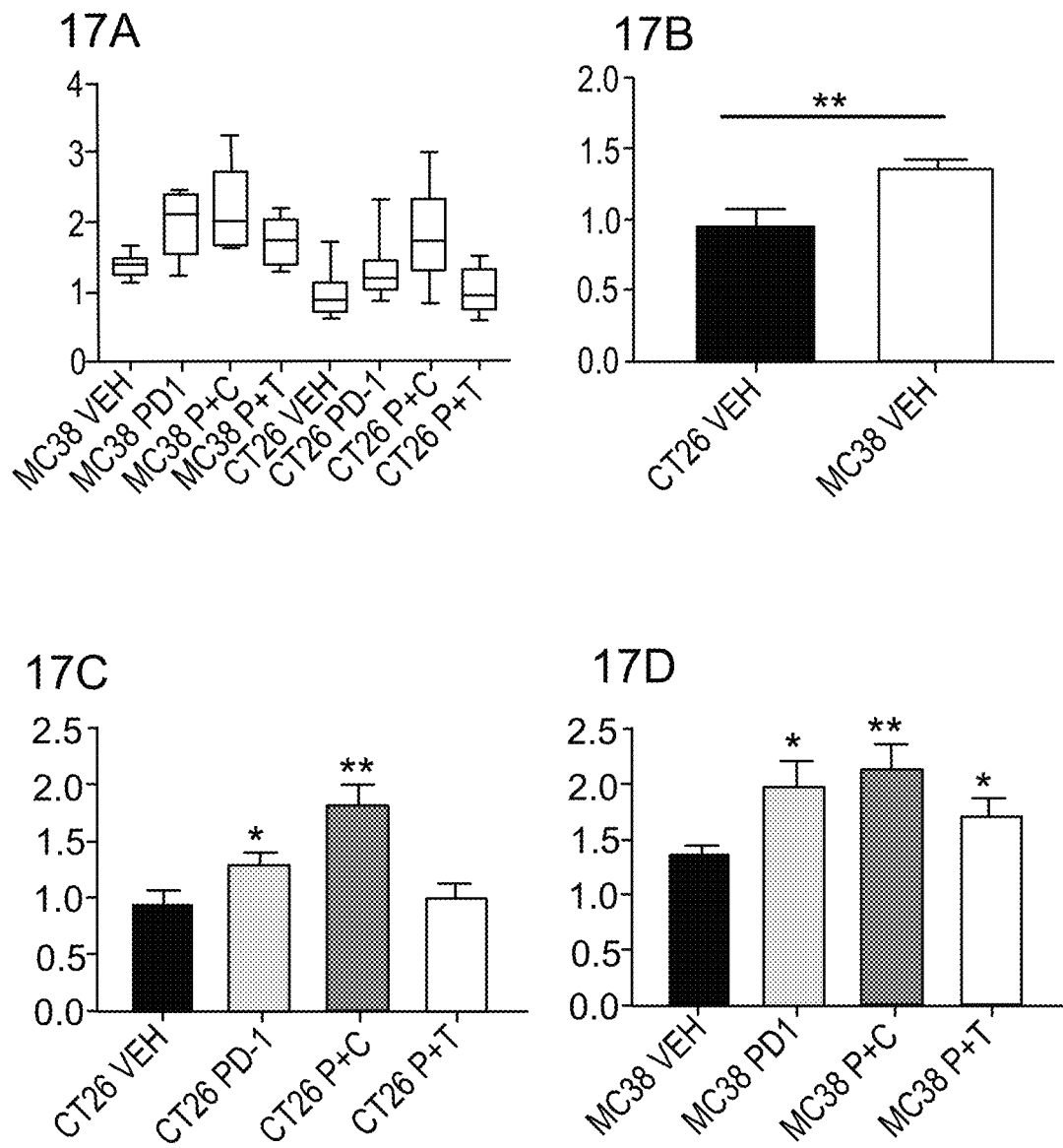
FIGS. 17A-17D show a comparison of granzyme B uptake by quantification of GZP PET imaging.

For example, in the CT26 model, vehicle-treated mice had no difference in tracer accumulation in the tumor and in the left ventricle, reflected by an average TBR of 0.97 t 0.07. In comparison, CT26 tumor-bearing mice receiving PD-1 monotherapy and P+C combination therapy had higher tumor uptake with mean TBRs of 1.32±0.15 (p<0.05) and 1.48±0.19 (p<0.005) respectively. Conversely, mice with CT26 tumors treated with P+T combination therapy demonstrated no elevated tumor trace accumulation in comparison to the vehicle-treated mice (TBR=0.99±0.14), as shown in FIG. 17C). In order to experimentally define a TBR threshold to predict response across the three therapy regimens, the highest TBR for vehicle-treated CT26 tumors, 1.27, was defined as the value above which tumors would be classified as high-uptake, and below which they would be classified as low-uptake. Using this cutoff for the CT26 model, 4 of 12 monotherapy, 6 of 12 P+C combination therapy, and 0 of 6 P+T combination therapy-treated mice were classified as high-uptake.

MC38 tumor-bearing mice also demonstrated differential tumor uptake based on therapy regimen. MC38 tumor-bearing saline-treated mice had an average TBR of 1.37 t 0.016, significantly higher than that of the saline-treated CT26 tumor-bearing mice (p<0.005) and indicative of a comparatively higher baseline granzyme B level in MC38 tumors, as shown in FIG. 17B consistent with western blot results. As in the CT26 model, MC38 tumor-bearing mice treated with both monotherapy and P+C combination therapy yielded significantly higher TBRs of 1.99±0.22 (p<0.05) and 2.17±0.21 (p<0.005), respectively, compared to the relevant control mice. However, unlike in the CT26 model, MC38 tumors treated with P+T combination therapy also yielded higher uptake than control tumors (TBR=1.74±0.12, p<0.05), although this group still had the lowest mean TBR among the three treatments, as shown in FIG. 17D). The threshold for high- and low-uptake for MC38 tumors was defined as 1.45 using the same rationale as described above for CT26 tumors, with an exception made for a single vehicle-treated tumor with high-uptake that demonstrated delayed growth in comparison to all other vehicle-treated tumors. The number of high-uptake MC38 tumors included 4 of 5 monotherapy, 8 of 8 P+C combination therapy, and 5 of 7 P+T combination therapy-treated mice.

Example 11. Growth Curve Analysis

Figures 18A, 18B, 18C, 18D, 18E, 18F:
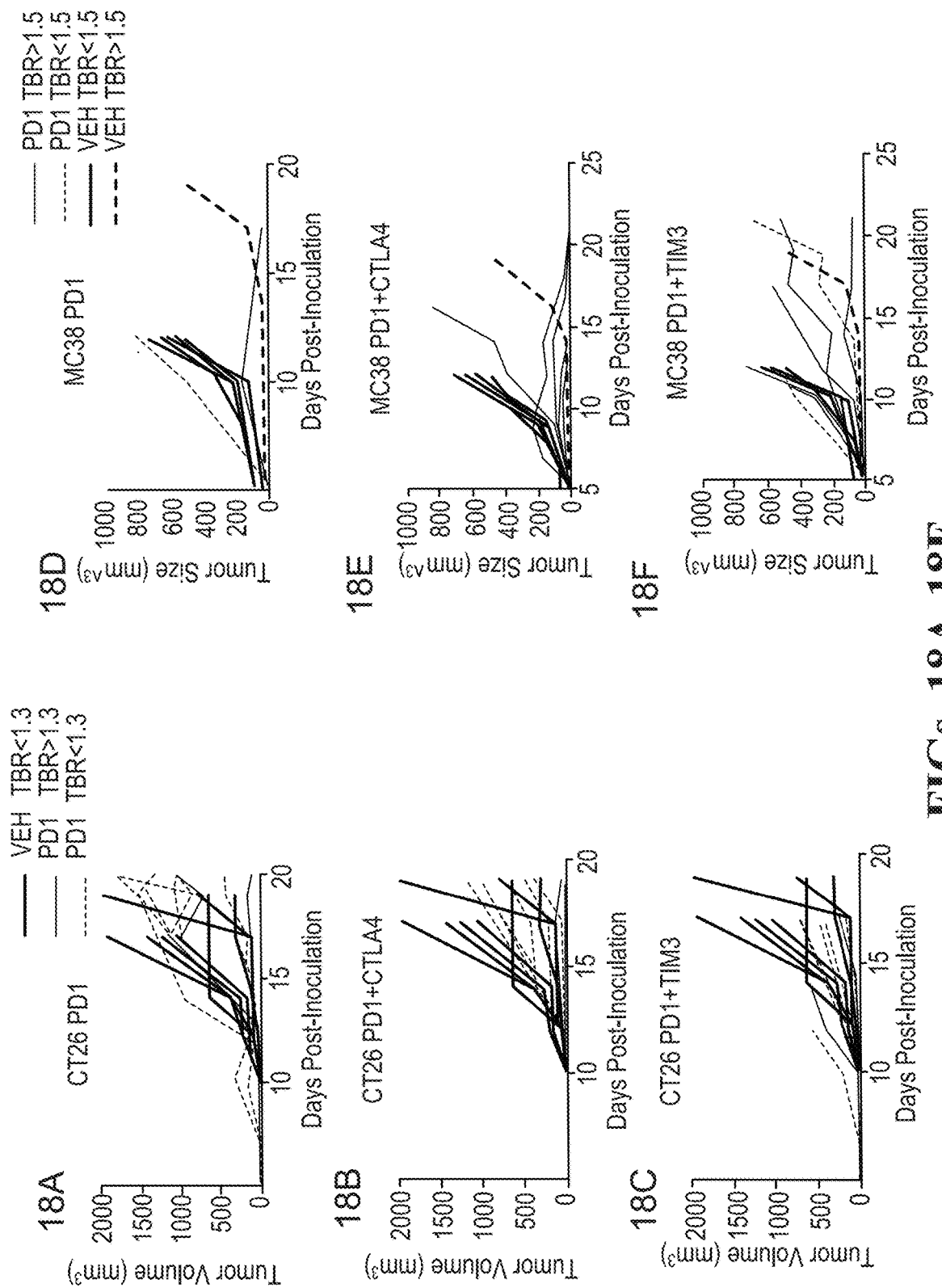
FIGS. 18A-18F show tumor growth following quantification of granzyme B expression. CT26 growth curves for monotherapy (FIG. 18A), P+C combination therapy (FIG. 18B), and P+T combination therapy (FIG. 18C) growth curves in comparison to saline-treated CT26 bearing mice are shown by a black solid line. High-granzyme tumors, as determined by PET imaging, are shown in a gray solid line and low-granzyme tumors are shown in a gray dotted line. Growth curves for MC38 tumors treated with monotherapy (FIG. 18D), P+C combination therapy (FIG. 18E), and P+T combination therapy (FIG. 18F) are differentiated by granzyme uptake, with high-granzyme treated mice shown in gray solid line, low-granzyme treated mice shown in a gray dotted line, high-granzyme vehicle-treated mice shown in a black dotted line, and low-granzyme vehicle-treated mice in a black solid line.

CT26 tumor growth described in Examples 9-10 was dichotomous, as tumors either regressed completely by day 20, or continued to grow until the end of the study, reaching a predefined maximum volume, or developing ulcerations. Based on these growth patterns, mice were categorized as responders if the tumor volume decreased to 0 mm³ or non-responders if tumor volume continued to increase. FIGS. 18A-18C illustrate the temporal changes in tumor volume for each therapy regimen, with vehicle-treated tumors represented in black. None of the vehicle-treated CT26 mice regressed in size, but 3 of 12 anti-PD-1 monotherapy, 7 of 12 P+C combination therapy, and 0 of 6 P+T combination therapy treated mice responded to therapy.

In the MC38 tumor model described in Examples 9-10, three groups were identified based on response patterns; complete responders, non-responders, and a third group classified as partial responders. Responding tumors regressed in size by day 20, non-responding tumors grew to 500 mm³ in size on or before day 14, and partially responding tumors reached 500 mm³ at a delayed time point later than day 14. FIGS. 18D-18F highlight these temporal patterns of tumor volume changes in MC38 based on therapy regimen with vehicle-treated tumor growth curves in black. Of the vehicle-treated MC38 tumors, 1 of the 7 showed significantly delayed tumor growth compared to the other vehicle-treated tumors and was thereby classified as a partial responder. This tumor had a TBR greater than 1.45 and as such is shown in dotted black line in FIGS. 18D-18F. A higher percentage of MC38 tumors responded to therapy compared to CT26 tumors, with 4 of 5 monotherapy treated tumors and 7 of 8 P+C combination therapy treated tumors completely regressing in size. Unlike CT26, MC38 tumors responded to P+T combination therapy, with 1 of 7 tumors responding completely, and an additional 4 of 7 demonstrating delayed growth in response to therapy characteristic of partial response.

Example 12. Response Prediction using Granzyme B PET Imaging

As a measure of the accuracy of granzyme B PET (i.e., GZP PET) imaging-based response prediction across multiple tumor models and therapies described in Examples 9-11, classifications of uptake using TBR thresholds of 1.27 for CT26 tumors and 1.45 for MC38 tumors were utilized. Using this classification system, 25 of 27 responding mice were categorized as high-uptake by GZP PET imaging, whereas 34 of the 38 mice that did not respond to treatment were classified as low-uptake. This reflects an overall sensitivity and specificity of 93% and 89% respectively for the ability of $^{68}$Ga-GZP PET to predict immunotherapy response. The sensitivity and specificity of the probe for each therapy type is shown in Table 5.

TABLE 5

| Tumor Model | Therapy Type | Average TBR | Responders (Partial or Full) | Percent Response | Sensitivity | Specificity |
|---|---|---|---|---|---|---|
| CT26 | Vehicle | 0.95 ± 0.07 | 0/8 | 0% | n/a | 8/8 |
| CT26 | Mono | 1.32 ± 0.15* | 3/12 | 25% | 3/3 | 8/9 |
| CT26 | PD1 + CTLA4 | 1.48 ± 0.19** | 7/12 | 58% | 6/7 | 5/5 |
| CT26 | PD1 + TIM3 | 0.99 ± 0.14 | 0/6 | 0% | n/a | 5/6 |
| MC38 | Vehicle | 1.37 ± 0.06 | 1/7 | 14% | 1/1 | 6/6 |
| MC38 | PD1 Mono | 1.99 ± 0.22* | 4/5 | 80% | 4/4 | 1/1 |
| MC38 | PD1 + CTLA4 | 2.17 ± 0.21** | 7/8 | 88% | 7/7 | 0/1 |
| MC38 | PD1 + TIM3 | 1.74 ± 0.12* | 5/7 | 71% | 4/5 | 1/2 |
| | | | TOTAL | | 93% (25/27) | 89% (34/38) |

Figure 19A:
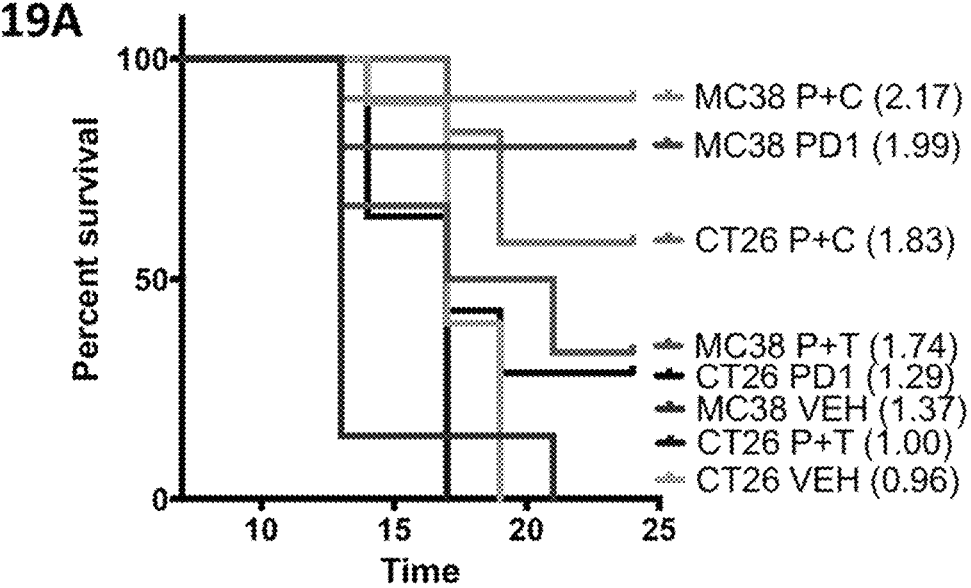
FIGS. 19A-19B show a correlation of response to GZP PET imaging score.
Figure 19B:
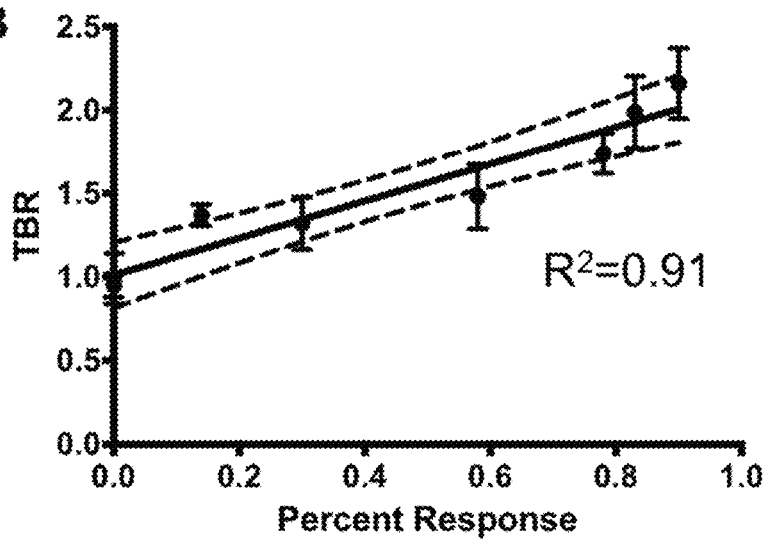

To compare whether the accuracy of granzyme B PET imaging for image response on an individual basis would permit group-based prediction of efficacy, the average TBR for each therapy was correlated with overall survival. Treatments with the best survival outcomes also had the highest average TBR based on a Kaplan Meier plot of survival for each therapy, as shown in FIG. 19A. To determine whether the relationship between percent response and average tumor uptake was correlated, percent response was plotted against TBR, as shown in FIG. 19B. The resulting curve showed a linear relationship with $R^2=0.84$ and a significantly non-zero slope ($p<0.0005$). suggesting that average TBR for a treatment group correlates linearly with percent survival.

Example 13. Synthesis of Additional Granzyme B Peptides

NOTA-beta A-PEG$_{27}$-G-G-G-I-E-F-D (GZPPEG; SEQ ID NO: 26; PEG=—(OCH$_2$CH$_2$)—) and NOTA-beta A-G-G-G-T-E-A-A-A-A-S—S—C—F—I-E-F-D-CHO (GZPSERP; SEQ ID NO: 27) were each prepared according to standard FMOC chemistry as described in Example 1. GZPSERP calculated m/z $[M+2H]^{2+}=1973.31$.

Figure 20:
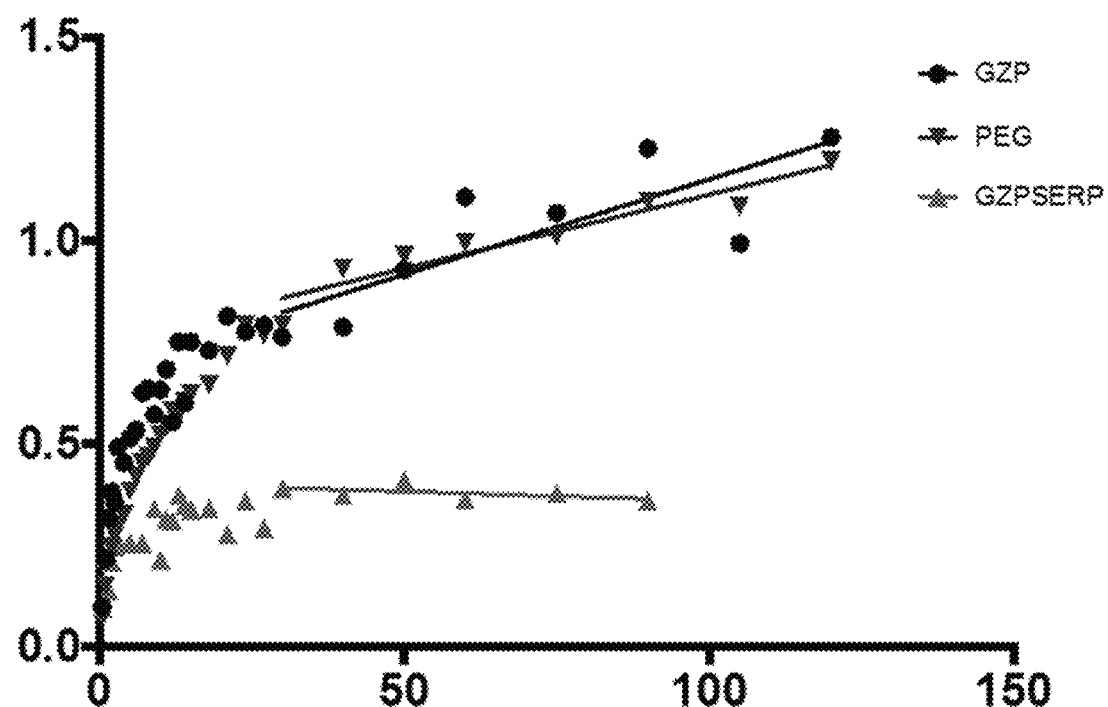
FIG. 20 shows a time course of PET signal in the tumor (heart) measured for NOTA-GP, GZPPEG, and GZPSERP.

Both peptides were designed to test the effects of additional groups on the pharmacokinetics and tumor to background ratios in mice. Dynamic PET analysis was performed using NOTA-GP (Example 1), GZPPEG, and GZPSERP. Surprisingly, GZPPEG displayed almost identical tumor uptake kinetics to NOTA-GP. GZPSERP, which is a hybrid blend between the SerpinP9-granzyme B binding sequence and the granzyme B peptide, resulted in much lower tumor to background ratios. Without being bound by any theory, it is believe that these effects were due to the strongly hydrophobic nature of the peptide, which resulted in significant aggregation and high liver uptake. A time course of PET signal in the tumor/heart for NOTA-GP, GZPPEG, and GZPSERP is shown in FIG. 20.

Example 14. Immunohistochemical Analyses of Human Melanoma Specimens

Immunohistochemistry was performed on formalin-fixed paraffin-embedded sections following standard antigen retrieval in citrate buffer. Granzyme B expression was detected with either an anti-Granzyme B antibody (ab5049, Abcam) or a biotinylated and humanized version of GZP (hGZP, see Example 1A). Bound antibody was detected with either HRP-conjugated goat anti-rabbit antibody and reacted with DAB substrate for IHC staining or AlexaFluor 488 goat anti-rabbit or AlexaFluor 594 goat anti-rabbit antibodies (Life Technologies) for immunofluorescent visualization. Bound peptide was detected with either HRP-conjugated streptavidin (Abcam) followed by reaction with DAB substrate or Oregon green conjugated neutravidin (Life Technologies). Patient samples were grouped as either immunotherapy treated or nontreated, and treated specimens were further distinguished as responders or nonresponders using modified RECIST criteria. Fluorescence quantification was performed using ImageJ software (National Institutes of Health, Bethesda, MD).

A cohort of 9 human melanoma biopsy samples obtained from patients treated with anti-PD-1 checkpoint inhibitors (n=6 nivolumab and n=3 pembrolizumab), which were retrospectively correlated with response based on modified RECIST criteria. Using an antihuman granzyme B antibody, on-treatment biopsy samples demonstrated distinct differences in the amount and intensity of granzyme B staining between treated responders and nonresponders by IHC, as show in FIG. 21A. To quantify the degree and magnitude of difference between treated responders and nonresponders, quantitative fluorescent microscopy was performed. Fluorescent microscopy analysis showed treated-responder specimen granzyme B expression up to ~1,000× greater than treated nonresponders and suggested continual increase in treated granzyme B expression over time, as shown in FIG.

21B). Finally, treated responder samples were analyzed by both immunohistochemistry and immunofluorescence to compare the ability of hGZP (Example 1A) to specifically detect granzyme B in human tissue and compare it to anti-granzyme B antibody. A strong correlation was observed by both techniques, indicating highly specific binding of hGZP to human granzyme B, as shown in FIGS. 21C-21D. These results suggest that there are significant differences in tumoral granzyme B expression between human responders and nonresponders and that these differences are recognized by the human granzyme B-specific probe.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

```
                          SEQUENCE LISTING

Sequence total quantity: 44
SEQ ID NO: 1            moltype =    length =
SEQUENCE: 1
000

SEQ ID NO: 2            moltype = AA   length = 7
FEATURE                 Location/Qualifiers
MOD_RES                 1
                        note = beta Ala
source                  1..7
                        mol_type = protein
                        organism = synthetic construct
SEQUENCE: 2
XGGIEFD                                                                  7

SEQ ID NO: 3            moltype = AA   length = 7
FEATURE                 Location/Qualifiers
source                  1..7
                        mol_type = protein
                        organism = synthetic construct
SEQUENCE: 3
GGGIEFD                                                                  7

SEQ ID NO: 4            moltype = AA   length = 7
FEATURE                 Location/Qualifiers
MOD_RES                 1
                        note = beta Ala
source                  1..7
                        mol_type = protein
                        organism = synthetic construct
SEQUENCE: 4
XGGIEPD                                                                  7

SEQ ID NO: 5            moltype =    length =
SEQUENCE: 5
000

SEQ ID NO: 6            moltype = AA   length = 4
FEATURE                 Location/Qualifiers
source                  1..4
                        mol_type = protein
                        organism = synthetic construct
SEQUENCE: 6
IEFD                                                                     4

SEQ ID NO: 7            moltype = AA   length = 4
FEATURE                 Location/Qualifiers
source                  1..4
                        mol_type = protein
                        organism = synthetic construct
SEQUENCE: 7
IEPD                                                                     4

SEQ ID NO: 8            moltype =    length =
SEQUENCE: 8
000

SEQ ID NO: 9            moltype = AA   length = 7
FEATURE                 Location/Qualifiers
MOD_RES                 1
                        note = beta Ala
source                  1..7
```

```
                        mol_type = protein
                        organism = synthetic construct
SEQUENCE: 9
XGGIEFD                                                                    7

SEQ ID NO: 10           moltype = AA   length = 7
FEATURE                 Location/Qualifiers
source                  1..7
                        mol_type = protein
                        organism = synthetic construct
SEQUENCE: 10
GGGIEFD                                                                    7

SEQ ID NO: 11           moltype = AA   length = 7
FEATURE                 Location/Qualifiers
MOD_RES                 1
                        note = beta Ala
source                  1..7
                        mol_type = protein
                        organism = synthetic construct
SEQUENCE: 11
XGGIEPD                                                                    7

SEQ ID NO: 12           moltype =     length =
SEQUENCE: 12
000

SEQ ID NO: 13           moltype = AA   length = 15
FEATURE                 Location/Qualifiers
source                  1..15
                        mol_type = protein
                        organism = synthetic construct
SEQUENCE: 13
GTEAAAASSC FVVAE                                                          15

SEQ ID NO: 14           moltype = AA   length = 15
FEATURE                 Location/Qualifiers
source                  1..15
                        mol_type = protein
                        organism = synthetic construct
SEQUENCE: 14
GTEAAAASAC FVVAE                                                          15

SEQ ID NO: 15           moltype = AA   length = 15
FEATURE                 Location/Qualifiers
source                  1..15
                        mol_type = protein
                        organism = synthetic construct
SEQUENCE: 15
GTEAAAASSA FVVAE                                                          15

SEQ ID NO: 16           moltype = AA   length = 15
FEATURE                 Location/Qualifiers
source                  1..15
                        mol_type = protein
                        organism = synthetic construct
SEQUENCE: 16
GTEAAAASSC AVVAE                                                          15

SEQ ID NO: 17           moltype = AA   length = 15
FEATURE                 Location/Qualifiers
source                  1..15
                        mol_type = protein
                        organism = synthetic construct
SEQUENCE: 17
GTEAAAASSC FAVAE                                                          15

SEQ ID NO: 18           moltype = AA   length = 15
FEATURE                 Location/Qualifiers
source                  1..15
                        mol_type = protein
                        organism = synthetic construct
SEQUENCE: 18
GTEAAAASSC FVAAE                                                          15

SEQ ID NO: 19           moltype = AA   length = 15
FEATURE                 Location/Qualifiers
source                  1..15
                        mol_type = protein
```

```
                                organism = synthetic construct
SEQUENCE: 19
GTEAAAASSC FVVGE                                                               15

SEQ ID NO: 20           moltype = AA   length = 15
FEATURE                 Location/Qualifiers
source                  1..15
                        mol_type = protein
                        organism = synthetic construct
SEQUENCE: 20
GTEAAAASSC FVVAD                                                               15

SEQ ID NO: 21           moltype =   length =
SEQUENCE: 21
000

SEQ ID NO: 22           moltype = AA   length = 8
FEATURE                 Location/Qualifiers
MOD_RES                 1
                        note = beta Ala
source                  1..8
                        mol_type = protein
                        organism = synthetic construct
SEQUENCE: 22
XGGGIEPD                                                                       8

SEQ ID NO: 23           moltype = AA   length = 18
FEATURE                 Location/Qualifiers
MOD_RES                 1
                        note = beta Ala
source                  1..18
                        mol_type = protein
                        organism = synthetic construct
SEQUENCE: 23
XGGGTEAAAA SSCFIEFD                                                            18

SEQ ID NO: 24           moltype = AA   length = 18
FEATURE                 Location/Qualifiers
MOD_RES                 1
                        note = beta Ala
source                  1..18
                        mol_type = protein
                        organism = synthetic construct
SEQUENCE: 24
XGGGTEAAAA SSCFIEFD                                                            18

SEQ ID NO: 25           moltype = AA   length = 8
FEATURE                 Location/Qualifiers
MOD_RES                 1
                        note = beta Ala
source                  1..8
                        mol_type = protein
                        organism = synthetic construct
SEQUENCE: 25
XGGGIEPD                                                                       8

SEQ ID NO: 26           moltype = AA   length = 7
FEATURE                 Location/Qualifiers
source                  1..7
                        mol_type = protein
                        organism = synthetic construct
SEQUENCE: 26
GGGIEFD                                                                        7

SEQ ID NO: 27           moltype = AA   length = 18
FEATURE                 Location/Qualifiers
MOD_RES                 1
                        note = beta Ala
source                  1..18
                        mol_type = protein
                        organism = synthetic construct
SEQUENCE: 27
XGGGTEAAAA SSCFIEFD                                                            18

SEQ ID NO: 28           moltype = AA   length = 107
FEATURE                 Location/Qualifiers
MOD_RES                 101
                        note = beta Ala
source                  1..107
```

```
                        mol_type = protein
                        organism = synthetic construct
SEQUENCE: 28
XXXXXXXXX XXXXXXXXX XXXXXXXXX XXXXXXXXX XXXXXXXXX XXXXXXXXX     60
XXXXXXXXX XXXXXXXXX XXXXXXXXX XXXXXXXXX XGGIEFD                 107

SEQ ID NO: 29           moltype = AA  length = 107
FEATURE                 Location/Qualifiers
source                  1..107
                        mol_type = protein
                        organism = synthetic construct
SEQUENCE: 29
XXXXXXXXX XXXXXXXXX XXXXXXXXX XXXXXXXXX XXXXXXXXX XXXXXXXXX     60
XXXXXXXXX XXXXXXXXX XXXXXXXXX XXXXXXXXX GGGIEFD                 107

SEQ ID NO: 30           moltype = AA  length = 107
FEATURE                 Location/Qualifiers
MOD_RES                 101
                        note = beta Ala
source                  1..107
                        mol_type = protein
                        organism = synthetic construct
SEQUENCE: 30
XXXXXXXXX XXXXXXXXX XXXXXXXXX XXXXXXXXX XXXXXXXXX XXXXXXXXX     60
XXXXXXXXX XXXXXXXXX XXXXXXXXX XXXXXXXXX XGGIEPD                 107

SEQ ID NO: 31           moltype = AA  length = 104
FEATURE                 Location/Qualifiers
source                  1..104
                        mol_type = protein
                        organism = synthetic construct
SEQUENCE: 31
XXXXXXXXX XXXXXXXXX XXXXXXXXX XXXXXXXXX XXXXXXXXX XXXXXXXXX     60
XXXXXXXXX XXXXXXXXX XXXXXXXXX XXXXXXXXX IEFD                    104

SEQ ID NO: 32           moltype = AA  length = 104
FEATURE                 Location/Qualifiers
source                  1..104
                        mol_type = protein
                        organism = synthetic construct
SEQUENCE: 32
XXXXXXXXX XXXXXXXXX XXXXXXXXX XXXXXXXXX XXXXXXXXX XXXXXXXXX     60
XXXXXXXXX XXXXXXXXX XXXXXXXXX XXXXXXXXX IEPD                    104

SEQ ID NO: 33           moltype = AA  length = 7
FEATURE                 Location/Qualifiers
MOD_RES                 1
                        note = beta Ala
source                  1..7
                        mol_type = protein
                        organism = synthetic construct
SEQUENCE: 33
XGGIEFD                                                         7

SEQ ID NO: 34           moltype = AA  length = 7
FEATURE                 Location/Qualifiers
source                  1..7
                        mol_type = protein
                        organism = synthetic construct
SEQUENCE: 34
GGGIEFD                                                         7

SEQ ID NO: 35           moltype = AA  length = 7
FEATURE                 Location/Qualifiers
MOD_RES                 1
                        note = beta Ala
source                  1..7
                        mol_type = protein
                        organism = synthetic construct
SEQUENCE: 35
XGGIEPD                                                         7

SEQ ID NO: 36           moltype = AA  length = 4
FEATURE                 Location/Qualifiers
source                  1..4
                        mol_type = protein
                        organism = synthetic construct
SEQUENCE: 36
IEFD                                                            4
```

```
SEQ ID NO: 37          moltype = AA  length = 4
FEATURE                Location/Qualifiers
source                 1..4
                       mol_type = protein
                       organism = synthetic construct
SEQUENCE: 37
IEPD                                                                      4

SEQ ID NO: 38          moltype = AA  length = 107
FEATURE                Location/Qualifiers
source                 1..107
                       mol_type = protein
                       organism = synthetic construct
SEQUENCE: 38
XXXXXXXXXX XXXXXXXXXX XXXXXXXXXX XXXXXXXXXX XXXXXXXXXX XXXXXXXXXX         60
XXXXXXXXXX XXXXXXXXXX XXXXXXXXXX XXXXXXXXXX XXXIEFD                      107

SEQ ID NO: 39          moltype = AA  length = 107
FEATURE                Location/Qualifiers
source                 1..107
                       mol_type = protein
                       organism = synthetic construct
SEQUENCE: 39
XXXXXXXXXX XXXXXXXXXX XXXXXXXXXX XXXXXXXXXX XXXXXXXXXX XXXXXXXXXX         60
XXXXXXXXXX XXXXXXXXXX XXXXXXXXXX XXXXXXXXXX XXXIEPD                      107

SEQ ID NO: 40          moltype = AA  length = 7
FEATURE                Location/Qualifiers
source                 1..7
                       mol_type = protein
                       organism = synthetic construct
SEQUENCE: 40
XXXIEFD                                                                   7

SEQ ID NO: 41          moltype = AA  length = 7
FEATURE                Location/Qualifiers
source                 1..7
                       mol_type = protein
                       organism = synthetic construct
SEQUENCE: 41
XXXIEPD                                                                   7

SEQ ID NO: 42          moltype = AA  length = 118
FEATURE                Location/Qualifiers
MOD_RES                101
                       note = beta Ala
source                 1..118
                       mol_type = protein
                       organism = synthetic construct
SEQUENCE: 42
XXXXXXXXXX XXXXXXXXXX XXXXXXXXXX XXXXXXXXXX XXXXXXXXXX XXXXXXXXXX         60
XXXXXXXXXX XXXXXXXXXX XXXXXXXXXX XXXXXXXXXX XGGGTEAAAA SSCFIEFD          118

SEQ ID NO: 43          moltype = AA  length = 18
FEATURE                Location/Qualifiers
MOD_RES                1
                       note = beta Ala
source                 1..18
                       mol_type = protein
                       organism = synthetic construct
SEQUENCE: 43
XGGGTEAAAA SSCFIEFD                                                       18

SEQ ID NO: 44          moltype = AA  length = 7
FEATURE                Location/Qualifiers
MOD_RES                1
                       note = beta Ala
source                 1..7
                       mol_type = protein
                       organism = synthetic construct
SEQUENCE: 44
XGGIEFD                                                                   7
```

What is claimed is:

1. A compound of Formula I:

A—B—C(I), or a pharmaceutically acceptable salt thereof, wherein:

A comprises a chelating agent;

B is an optional linking group; and

C is a peptide that binds granzyme B, wherein the peptide comprises the amino acid sequence of beta-AGGGIEPD (SEQ ID NO: 22).

2. The compound of claim 1, wherein the chelating agent is 1,4,7-triazacyclononanetriacetic acid (NOTA) or 1,4,7,10-tetraazacyclododecane-1,4, 7, 10-tetraacetic acid (DOTA).

3. The compound of claim 1, wherein the peptide of C is attached to an electrophilic group at its C-terminus.

4. The compound of claim 3, wherein the electrophilic group is —C(O)H.

5. The compound of claim 1, wherein A further comprises an imaging agent, which is conjugated with the chelating agent.

6. The compound of claim 5, wherein the imaging agent is a radioisotope.

7. The compound of claim 6, wherein the radioisotope is $^{68}$Ga or $^{18}$F.

8. The compound of claim 6, wherein the radioisotope is $^{68}$Ga and the chelating agent is NOTA.

9. The compound of claim 1, wherein B is absent.

10. The compound of claim 9, wherein the chelating agent is 1,4,7-triazacyclononanetriacetic acid (NOTA) or 1,4,7,10-tetraazacyclododecane-1,4, 7, 10-tetraacetic acid (DOTA).

11. The compound of claim 9, wherein the peptide of C is attached to an electrophilic group at its C-terminus; and wherein the electrophilic group is —C(O)H.

12. The compound of claim 4, wherein A further comprises an imaging agent, which is conjugated with the chelating agent; and wherein the imaging agent is a radioisotope.

13. The compound of claim 12, wherein the radioisotope is $^{68}$Ga and the chelating agent is NOTA.

14. The compound of claim 1, wherein in Formula (I), A comprises a chelating agent of NOTA conjugated to a radioisotope of $^{68}$Ga, B is absent, and C is the peptide of beta-AGGGIEPD (SEQ ID NO: 22), the C-terminus of which is attached to an electrophilic group; and wherein the electrophilic group is —C(O)H.

15. A method for imaging Granzyme B, the method comprising:

(a) contacting cells or tissues with the compound of Formula (I) set forth in claim 1, wherein A further comprises an imaging agent, and (b) imaging Granzyme B in the cells or tissues based on signals released from the imaging agent.

16. The method of claim 15, wherein the contacting step is performed by administering the compound to a subject in need thereof.

17. The method of claim 16, wherein the subject is a human cancer patient.

18. The method of claim 17, wherein the human cancer patient is administered an immunotherapeutic agent prior to administration of the compound.

19. The method of claim 17, wherein the method further comprises assessing treatment efficacy of the immunotherapeutic agent based on results from step (b).

20. The method of claim 17, wherein in Formula (I), A comprises a chelating agent of NOTA conjugated to a radioisotope of $^{68}$Ga, B is absent, and C is the peptide of beta-AGGGIEPD (SEQ ID NO: 22), the C-terminus of which is attached to an electrophilic group; and wherein the electrophilic group is —C(O)H.

* * * * *